US012128403B2

(12) United States Patent
Kim et al.

(10) Patent No.: US 12,128,403 B2
(45) Date of Patent: Oct. 29, 2024

(54) FLUID DELIVERY METHODS

(71) Applicant: 10x Genomics, Inc., Pleasanton, CA (US)

(72) Inventors: Hanyoup Kim, Foster City, CA (US); Augusto Manuel Tentori, Dublin, CA (US); Siyuan Xing, Newark, CA (US); Rajiv Bharadwaj, Pleasanton, CA (US); Bill Kengli Lin, Pleasanton, CA (US); Felice Alessio Bava, Pleasanton, CA (US); Pratomo Putra Alimsijah, Pleasanton, CA (US); Nabil Mikhaiel, Dublin, CA (US)

(73) Assignee: 10x Genomics, Inc., Pleasanton, CA (US)

(*) Notice: Subject to any disclaimer, the term of this patent is extended or adjusted under 35 U.S.C. 154(b) by 25 days.

(21) Appl. No.: 17/873,586

(22) Filed: Jul. 26, 2022

(65) Prior Publication Data
US 2023/0017773 A1 Jan. 19, 2023

Related U.S. Application Data

(63) Continuation of application No. PCT/US2021/036788, filed on Jun. 10, 2021.
(Continued)

(51) Int. Cl.
*B01L 3/00* (2006.01)
*C12Q 1/6837* (2018.01)
(Continued)

(52) U.S. Cl.
CPC ............ *B01L 3/502715* (2013.01); *B01L 3/502723* (2013.01); *C12Q 1/6837* (2013.01);
(Continued)

(58) Field of Classification Search
None
See application file for complete search history.

(56) References Cited

U.S. PATENT DOCUMENTS 4,514,388 A 4/1985 Psaledakis
4,683,195 A 7/1987 Mullis et al.
(Continued)

FOREIGN PATENT DOCUMENTS

EP 0961110 A2 12/1999
EP 0901631 B1 8/2004
(Continued)

OTHER PUBLICATIONS

U.S. Appl. No. 61/839,313, filed Jun. 25, 2013, Chee et al.
(Continued)

*Primary Examiner* — Robert T. Crow
(74) *Attorney, Agent, or Firm* — Mintz Levin Cohn Ferris Glovsky and Popeo, P.C.

(57) ABSTRACT

Provided herein is a fluid delivery method for permeabilizing a biological sample. The method includes delivering the fluid to a first substrate and/or a second substrate. At least one of the first substrate and the second substrate includes a spacer. The method further includes assembling, subsequent to the delivering, a chamber comprising the first substrate, the second substrate, the biological sample, and the spacer. The spacer may be disposed between the first substrate and second substrate. The spacer may be configured to maintain the fluid within the chamber and maintain a separation distance between the first substrate and the second substrate. The spacer may be positioned to at least partially surround an area on the first substrate on which the biological sample is disposed and/or at least partially surround the array disposed on the second substrate.

20 Claims, 48 Drawing Sheets

Related U.S. Application Data

(60) Provisional application No. 63/037,417, filed on Jun. 10, 2020, provisional application No. 63/106,779, filed on Oct. 28, 2020, provisional application No. 63/080,514, filed on Sep. 18, 2020.

(51) Int. Cl.
*C12Q 1/6841* (2018.01)
*G01N 1/31* (2006.01)

(52) U.S. Cl.
CPC ............ *C12Q 1/6841* (2013.01); *G01N 1/312* (2013.01); *B01L 2200/027* (2013.01); *B01L 2300/0822* (2013.01); *B01L 2400/0421* (2013.01)

(56) References Cited

U.S. PATENT DOCUMENTS

| | | | |
|---|---|---|---|
| 4,731,335 A * | 3/1988 | Brigati | G01N 1/31 118/421 |
| 5,503,980 A | 4/1996 | Cantor | |
| 5,559,032 A | 9/1996 | Pomeroy et al. | |
| 5,641,658 A | 6/1997 | Adams et al. | |
| 5,658,751 A | 8/1997 | Yue et al. | |
| 5,716,825 A | 2/1998 | Hancock et al. | |
| 5,750,341 A | 5/1998 | Macevicz | |
| 5,763,175 A | 6/1998 | Brenner | |
| 6,013,440 A | 1/2000 | Lipshutz et al. | |
| 6,083,761 A | 7/2000 | Kedar et al. | |
| 6,143,496 A | 11/2000 | Brown et al. | |
| 6,210,894 B1 | 4/2001 | Brennan | |
| 6,214,587 B1 | 4/2001 | Dattagupta et al. | |
| 6,266,459 B1 | 7/2001 | Walt et al. | |
| 6,274,320 B1 | 8/2001 | Rothberg et al. | |
| 6,309,824 B1 | 10/2001 | Drmanac | |
| 6,344,316 B1 | 2/2002 | Lockhart et al. | |
| 6,355,431 B1 | 3/2002 | Chee et al. | |
| 6,401,267 B1 | 6/2002 | Drmanac | |
| 6,404,907 B1 | 6/2002 | Gilchrist et al. | |
| 6,432,360 B1 | 8/2002 | Church | |
| 6,544,732 B1 | 4/2003 | Chee et al. | |
| 6,544,790 B1 | 4/2003 | Sabatini | |
| 6,620,584 B1 | 9/2003 | Chee et al. | |
| 6,632,641 B1 | 10/2003 | Brennan et al. | |
| 6,673,620 B1 | 1/2004 | Loeffler et al. | |
| 6,770,441 B2 | 8/2004 | Dickinson et al. | |
| 6,787,308 B2 | 9/2004 | Balasubramanian et al. | |
| 6,812,005 B2 | 11/2004 | Fan et al. | |
| 7,098,041 B2 | 8/2006 | Kaylor et al. | |
| 7,166,431 B2 | 1/2007 | Chee et al. | |
| 7,255,994 B2 | 8/2007 | Lao | |
| 7,393,665 B2 | 7/2008 | Brenner | |
| 7,709,198 B2 | 5/2010 | Luo et al. | |
| 8,206,917 B2 | 6/2012 | Chee et al. | |
| 8,460,865 B2 | 6/2013 | Chee et al. | |
| 8,604,182 B2 | 12/2013 | Luo et al. | |
| 8,951,726 B2 | 2/2015 | Luo et al. | |
| 8,951,781 B2 | 2/2015 | Williamson et al. | |
| 9,371,598 B2 | 6/2016 | Chee | |
| 9,557,330 B2 | 1/2017 | Siciliano et al. | |
| 9,582,877 B2 | 2/2017 | Fu et al. | |
| 9,593,365 B2 | 3/2017 | Frisen et al. | |
| 9,727,810 B2 | 8/2017 | Fodor et al. | |
| 9,783,841 B2 | 10/2017 | Nolan et al. | |
| 9,868,979 B2 | 1/2018 | Chee et al. | |
| 10,002,316 B2 | 6/2018 | Fodor et al. | |
| 10,041,949 B2 | 8/2018 | Bendall et al. | |
| 10,059,990 B2 | 8/2018 | Boyden et al. | |
| 11,501,440 B2 | 11/2022 | Weisenfeld et al. | |
| 2002/0022261 A1 * | 2/2002 | Anderson | B01L 3/5027 435/287.9 |
| 2002/0040275 A1 | 4/2002 | Cravatt et al. | |
| 2002/0150909 A1 | 10/2002 | Stuelpnagel et al. | |
| 2002/0164611 A1 | 11/2002 | Bamdad et al. | |
| 2003/0175947 A1 | 9/2003 | Liu et al. | |
| 2003/0215936 A1 | 11/2003 | Kallioniemi et al. | |
| 2004/0067492 A1 | 4/2004 | Peng et al. | |
| 2004/0082059 A1 | 4/2004 | Webb et al. | |
| 2004/0112442 A1 | 6/2004 | Maerkl et al. | |
| 2004/0248287 A1 * | 12/2004 | Hu | B01L 3/508 435/287.2 |
| 2005/0095627 A1 | 5/2005 | Kolman et al. | |
| 2005/0106617 A1 * | 5/2005 | Besemer | B01L 9/527 506/40 |
| 2005/0179746 A1 | 8/2005 | Roux et al. | |
| 2006/0164490 A1 | 7/2006 | Kim et al. | |
| 2007/0099208 A1 | 5/2007 | Drmanac et al. | |
| 2007/0116612 A1 | 5/2007 | Williamson, IV | |
| 2007/0264656 A1 | 11/2007 | Kawamura | |
| 2008/0145616 A1 | 6/2008 | Gharib et al. | |
| 2008/0218838 A1 * | 9/2008 | Rey-Mermet | G02F 1/1339 428/34.1 |
| 2009/0005252 A1 | 1/2009 | Drmanac et al. | |
| 2009/0018024 A1 | 1/2009 | Church et al. | |
| 2009/0068667 A1 * | 3/2009 | Meisner | C12Q 1/6841 435/6.16 |
| 2009/0152116 A1 * | 6/2009 | Boles | C12Q 1/6816 204/461 |
| 2009/0253582 A1 | 10/2009 | Pena et al. | |
| 2009/0321262 A1 | 12/2009 | Adachi et al. | |
| 2010/0035249 A1 | 2/2010 | Hayashizaki et al. | |
| 2010/0151511 A1 | 6/2010 | Greenizen et al. | |
| 2010/0210475 A1 | 8/2010 | Lee et al. | |
| 2010/0282617 A1 | 11/2010 | Rothberg et al. | |
| 2011/0028685 A1 | 2/2011 | Purkayastha et al. | |
| 2011/0165178 A1 * | 7/2011 | Wasylyk | G01N 33/57434 435/7.1 |
| 2012/0279954 A1 | 11/2012 | Ceremony et al. | |
| 2013/0052331 A1 | 2/2013 | Kram et al. | |
| 2013/0053273 A1 | 2/2013 | Juncker et al. | |
| 2013/0065788 A1 | 3/2013 | Glezer et al. | |
| 2013/0096033 A1 | 4/2013 | Routenberg | |
| 2013/0244895 A1 * | 9/2013 | Voros | G01N 21/6428 506/9 |
| 2014/0011707 A1 * | 1/2014 | Ye | B01L 3/5027 506/16 |
| 2014/0066318 A1 | 3/2014 | Frisen et al. | |
| 2014/0323330 A1 | 10/2014 | Bergo | |
| 2015/0148239 A1 | 5/2015 | Peter et al. | |
| 2015/0346104 A1 * | 12/2015 | Chou | G01N 21/763 422/69 |
| 2016/0033496 A1 | 2/2016 | Chou et al. | |
| 2016/0299165 A1 | 10/2016 | Zhou | |
| 2017/0016053 A1 | 1/2017 | Beechem et al. | |
| 2018/0095067 A1 | 4/2018 | Huff et al. | |
| 2018/0104694 A1 | 4/2018 | Huff et al. | |
| 2018/0127817 A1 | 5/2018 | Borchert et al. | |
| 2018/0217094 A1 | 8/2018 | Herr et al. | |
| 2018/0245142 A1 | 8/2018 | So et al. | |
| 2018/0257075 A1 | 9/2018 | Yellen et al. | |
| 2018/0305681 A1 | 10/2018 | Jovanovich et al. | |
| 2019/0276880 A1 * | 9/2019 | Fan | C12Q 1/6837 |
| 2020/0277663 A1 | 9/2020 | Ramachandran Iyer et al. | |
| 2020/0277664 A1 | 9/2020 | Frenz | |
| 2020/0325531 A1 | 10/2020 | Chee | |
| 2020/0363408 A1 | 11/2020 | Chou et al. | |
| 2021/0150707 A1 | 5/2021 | Weisenfeld et al. | |
| 2021/0155982 A1 | 5/2021 | Yin et al. | |

FOREIGN PATENT DOCUMENTS

| | | |
|---|---|---|
| EP | 1 782 737 A1 | 5/2007 |
| EP | 1878502 A1 | 1/2008 |
| EP | 1923471 B1 | 12/2012 |
| EP | 3013983 A1 | 5/2016 |
| EP | 3013984 A1 | 5/2016 |
| EP | 2350648 B1 | 3/2017 |
| WO | 8910977 A1 | 11/1989 |
| WO | 9525116 A1 | 9/1995 |
| WO | 9535505 A1 | 12/1995 |
| WO | 02077283 A1 | 10/2002 |
| WO | 03002979 A2 | 1/2003 |

(56) References Cited

FOREIGN PATENT DOCUMENTS

| | | |
|---|---|---|
| WO | WO-2004/108268 A1 | 12/2004 |
| WO | 2005007814 A3 | 6/2005 |
| WO | 2007076726 A1 | 7/2007 |
| WO | 2008157801 A2 | 12/2008 |
| WO | 2010126614 A2 | 11/2010 |
| WO | 2011102903 A1 | 8/2011 |
| WO | WO-2011/094669 A1 | 8/2011 |
| WO | WO-2011/127099 A1 | 10/2011 |
| WO | WO-2012/140224 A1 | 10/2012 |
| WO | WO-2014/060483 A1 | 4/2014 |
| WO | 2014142841 A1 | 9/2014 |
| WO | WO-2014/163886 A1 | 10/2014 |
| WO | 2014210223 A1 | 12/2014 |
| WO | 2014210225 A1 | 12/2014 |
| WO | WO-2014/210233 A1 | 12/2014 |
| WO | WO-2015/161173 A1 | 10/2015 |
| WO | WO-2016/007839 A1 | 1/2016 |
| WO | WO-2016/057552 A1 | 4/2016 |
| WO | WO-2016/126882 A1 | 8/2016 |
| WO | 2016138496 A1 | 9/2016 |
| WO | 2016138500 A1 | 9/2016 |
| WO | 2016162309 A1 | 10/2016 |
| WO | 2016168825 A1 | 10/2016 |
| WO | WO-2016/166128 A1 | 10/2016 |
| WO | 2017019456 A2 | 2/2017 |
| WO | WO-2017/027367 A1 | 2/2017 |
| WO | WO-2017/027368 A1 | 2/2017 |
| WO | 2017048871 A1 | 3/2017 |
| WO | WO-2017/048881 A1 | 3/2017 |
| WO | 2017112957 A1 | 6/2017 |
| WO | WO-2017/144338 A1 | 8/2017 |
| WO | WO-2017/147483 A1 | 8/2017 |
| WO | WO-2017/222453 A1 | 12/2017 |
| WO | WO-2018/022809 A1 | 2/2018 |
| WO | WO-2018/045181 A1 | 3/2018 |
| WO | WO-2018/045186 A1 | 3/2018 |
| WO | WO-2018/057999 A1 | 3/2018 |
| WO | WO-2018/075436 A1 | 4/2018 |
| WO | 2018091676 A1 | 5/2018 |
| WO | WO-2018/107054 A1 | 6/2018 |
| WO | WO-2018/136856 A1 | 7/2018 |
| WO | 2018148471 A2 | 8/2018 |
| WO | WO-2018/144582 A1 | 8/2018 |
| WO | 2019012005 A1 | 1/2019 |
| WO | WO-2019/068880 A1 | 4/2019 |
| WO | WO-2019/075091 A1 | 4/2019 |
| WO | 2019140334 A1 | 7/2019 |
| WO | 2020047004 A2 | 3/2020 |
| WO | WO-2020/061108 A1 | 3/2020 |
| WO | 2020123320 A3 | 7/2020 |
| WO | WO-2020/176788 A1 | 9/2020 |
| WO | WO-2021/067514 A1 | 4/2021 |
| WO | WO-2021/102003 A1 | 5/2021 |
| WO | WO-2021/102005 A1 | 5/2021 |
| WO | 2021252747 A1 | 12/2021 |

OTHER PUBLICATIONS

U.S. Appl. No. 61/839,320, filed Jun. 25, 2013, Chee et al.
(Aug. 8, 2022) BeadArray Technology, Gene Arrays Services, <https://web.archive.org/web/20150214084616/http://genearrays.com/services/microarrays/illumina/beadarray-technology/>, [retrieved on Jan. 30, 2020], 3 pages.
International Search Report and Written Opinion received for PCT Application No. PCT/US2021/036788, dated Nov. 1, 2021, 14 pages.
Affymetrix ( Feb. 26, 2003) "GeneChip® Human Genome U133 Set", retrieved from the Internet: on the World Wide Web at affymetrix.com/support/technical/datasheets/hgu133_datasheet.pdf, 2 pages.
Affymetrix (Oct. 2, 2002) "GeneChip® Human Genome U95 Set", Datasheet, retrieved from the internet: on the World Wide Web affymetrix.com, 2 pages.
Anonymous (Jun. 15, 2018) "ST Spot Detector Usage Guide. A Guide to Using the Spatial Transcriptomics Spot Detector 2.0", GitHub, 1 page.
Anonymous (2019) "Visium Spatial Gene Expression Imaging Guidelines", 10xGenomics.com, pp. 1-8 (11 pages).
Armani et al. (Dec. 21, 2009) "2D-PCR: A Method of Mapping DNA in Tissue Sections", Lab on a Chip, 9 (24):3526-3534 (19 pages).
Asp et al. (May 4, 2020) "Spatially Resolved Transcriptomes-Next Generation Tools for Tissue Exploration", Bioessays, 42(10):1900221(16 pages).
Beechem et al. (2020) "High-Plex Spatially Resolved RNA and Protein Detection Using Digital Spatial Profiling: A Technology Designed for Immuno-oncology Biomarker Discovery and Translational Research", Chapter 25 in Biomarkers for Immunotherapy of Cancer. Methods and Protocols, Methods in Molecular Biology, 563-583.
Birney et al. (Jun. 14, 2007) "Identification and Analysis of Functional Elements in 1% of The Human Genome by the ENCODE Pilot Project", Nature, 447(7146):799-816.
Blokzijl et al. (Sep. 2010) "Profiling Protein Expression and Interactions: Proximity Ligation as a Tool for Personalized Medicine", Journal of Internal Medicine, 268(3):232-245.
Blow et al. (Aug. 23, 2007) "Tissue preparation: Tissue issues", Nature, 448(7156):959-962.
Brenner et al. (Jun. 2000) "Gene Expression Analysis by Massively Parallel Signature Sequencing (MPSS) on Microbead Arrays", Nature Biotechnology, 18(6):630-634.
Burgess D.J. (Jul. 15, 2016) "Gene Expression: a Space for Transcriptomics", Nature Reviews Genetics, 1 page.
Burgess D.J. (Apr. 13, 2018) "Transcriptomics: Finding Structure in Gene Expression", Nature Reviews Genetics, 19(5):249(1 page).
Burton et al. (Jan. 1998) "Coverslip mounted-immersion cycled in situ RT-PCR for the localization of mRNA in issue sections", Biotechniques, 24(1):92-100 (6 pages).
Cardona et al. (Sep. 8, 2011) "TrakEM2 0.9a User Manual", https://www.ini.uzh.ch/~acardona/trakem2manual.html, 38 pages.
Chandra, (Feb. 2010) "Cell-free synthesis-based protein microarrays and their applications", Proteomics, 5 (6):717-730.
Constantine et al. (1998) "Use of genechip high-density oligonucleotide arrays for gene expression monitoring", Amersham Life Science, 11-14.
Crosetto et al. (Jan. 2015) "Spatially resolved transcriptomics and beyond", Nature Review Genetics, 16 (1):57-66.
Eguiluz et al. (2006) "Multitissue array review: a chronological description of tissue array techniques, applications and procedures", Pathology Research and Practice, 202(8):561-568.
Fodor et al. (Feb. 15, 1991) "Light-Directed, Spatially Addressable Parallel Chemical Synthesis", Science, 251 (4995):767-773.
Gnanapragasam V.J. (Jan. 2010) "Unlocking the molecular archive: the emerging use of formalin-fixed paraffin-embedded tissue for biomarker research in urological cancer", BJU International, 105(2):274-278.
Gunderson et al. (May 2004) "Decoding Randomly Ordered DNA Arrays", Genome Research, 14(5):870-877 (9 pages).
He et al. (Feb. 2008) "In situ synthesis of protein arrays", Current Opinion in Biotechnology, 19(1):4-9.
Jemt et al. (Nov. 16, 2016) "An automated approach to prepare tissue-derived spatially barcoded RNA-sequencing libraries", Scientific Reports, 6:37137(10 pages).
Lage et al. (Feb. 2003) "Whole genome analysis of genetic alterations in small DNA samples using hyperbranched strand displacement amplification and array-CGH", Genome Research, 13(2):294-307.
Miller et al. (Oct. 2009) "Basic concepts of microarrays and potential applications in clinical microbiology", Clinical Microbiology Reviews, 22(4):611-633.
Navarro et al. (Mar. 15, 2019) "ST Viewer: A Tool for Analysis and Visualization of Spatial Transcriptomics Datasets", Bioinformatics, 35(6):1058-1060.
Pettersson et al. (Feb. 2009) "Generations of sequencing technologies", Genomics, 93(2):105-111.

(56) References Cited

OTHER PUBLICATIONS

Schena et al. (Oct. 20, 1995) "Quantitative Monitoring of Gene Expression Patterns with a Complementary DNA Microarray", Science, 270(5235):467-470.
Stahl et al. (Jul. 1, 2016) "Visualization and analysis of gene expression in tissue sections by spatial transcriptomics", Science, 353(6294):78-82 (6 pages).
Strell et al. (Apr. 2019) "Placing RNA in context and space—methods for spatially resolved transcriptomics,", The FEBS Journal, 286(8):1468-1481.
Wilbrey-Clark et al. (Apr. 27, 2020) "Cell Atlas Technologies and Insights Into Tissue Architecture", The Biochemical Journal, 477(8):1427-1442.
Wong et al. (Jun. 1, 2018) "ST Spot Detector: A Web-Based Application for Automatic Spot and Tissue Detection for Spatial Transcriptomics Image Datasets", Bioinformatics, 34(11):1966-1968.
Chen, K.H et al. (Apr. 24, 2015). "Spatially resolved, highly multiplexed RNA profiling in single cells," Science 348(6233): aaa6090.
Credle, J.J. et al. (Aug. 21, 2017). "Multiplexed analysis of fixed tissue RNA using Ligation in situ Hybridization," *Nucleic Acids Research* 45(14): e128.
Final Office Action mailed on Jan. 31, 2022, for U.S. Appl. No. 17/172,926, filed Feb. 10, 2021, 33 pages.
Final Office Action mailed on Sep. 14, 2022, for U.S. Appl. No. 17/172,926, filed Feb. 10, 2021, 30 pages.
Final Office Action mailed on Jan. 26, 2023, for U.S. Appl. No. 17/172,926, filed Feb. 10, 2021, 24 pages.
Final Office Action mailed on Sep. 20, 2022, for U.S. Appl. No. 17/665,169, filed Feb. 4, 2022, 7 pages.
Forster, S.C. et al. (Feb. 2019, e-published Feb. 4, 2019). "A human gut bacterial genome and culture collection for improved metagenomic analyses," *Nature Biotechnology* 37(2): 186-192.
Gabbatiss, J. et al. (Apr. 24, 2018). "New form of DNA discovered inside living human cells," *The Independent* pp. 1-3.
Gao, R. et al. (2017). "Q&A: Expansion microscopy," *BMC Biology* 15(1):50.
Gupta, I. et al. (Oct. 15, 2018). "Single-cell isoform RNA sequencing characterizes isoforms in thousands of cerebellar cells," *Nature Biotechnology* 36:1197-1202.
"Human Genome" Wikipedia .com located at <https://en.wikipedia.org/wiki/Human_genome#:~:text=The%20human%20genome%20is%20a,genome%20and%20the%20mitochondrial%20genome> last accessed Feb. 7, 2024, 33 pages.

International Preliminary Report on Patentability mailed on Jun. 8, 2021, for PCT Application No. PCT/US2019/065100, filed Dec. 6, 2019, 13 pages.
International Search Report mailed on Jun. 23, 2020, for PCT Application No. PCT/US2019/065100, filed Dec. 6, 2019, 8 pages.
International Preliminary Report on Patentability mailed on Sep. 28, 2021, for PCT Application No. PCT/US2020/029843, filed Apr. 24, 2020, 14 pages.
International Search Report mailed on Oct. 7, 2020, for PCT Application No. PCT/US2020/029843, filed Apr. 24, 2020, 6 pages.
Lee, J.H. et al. (Mar. 2015, e-published Feb. 12, 2015). "Fluorescent in situ sequencing (FISSEQ) of RNA for gene expression profiling in intact cells and tissues," *Nature Protocols* 10(3):442-458.
Liu, H. et al. (Dec. 15, 2010, e-published Jul. 30, 2010). "An integrated and sensitive detection platform for biosensing application based on Fe@Au magnetic nanoparticles as bead array carries," *Biosensors and Bioelectronics* 26(4): 1442-1448.
Non-Final Office Action mailed on May 10, 2021, for U.S. Appl. No. 17/172,926, filed Feb. 10, 2021, 33 pages.
Non-Final Office Action mailed on May 12, 2022, for U.S. Appl. No. 17/665,169, filed Feb. 4, 2022, 8 pages.
Non-Final Office Action mailed on Aug. 3, 2023, for U.S. Appl. No. 17/665,169, filed Feb. 4, 2022, 6 pages.
Non-Final Office Action mailed on Nov. 27, 2023, for U.S. Appl. No. 17/665,169, filed Feb. 4, 2022, 8 pages.
Non-Final Office Action mailed on May 22, 2023, for U.S. Appl. No. 18/049,094, filed Oct. 24, 2022, 32 pages.
Rodriques, S.G. et al. (Mar. 29, 2019, e-published Mar. 28, 2019). "Slide-seq: A scalable technology for measuring genome-wide expression at high spatial resolution," *Science* 363(6434): 1463-1467.
Sah, R. et al. (Mar. 12, 2020). "Complete Genome Sequence of a 2019 Novel Coronavirus (SARS-CoV-2) Strain Isolated in Nepal," *Microbiology Resource Announcements* 9(11):e00169-20.
Sumitomo, K. et al. (Jan. 15, 2012, e-published Nov. 15, 2011). "Ca2+ ion transport through channels formed by α-hemolysin analyzed using a microwell array on a Si substrate," *Biosensors and Bioelectronics* 31(1):445-450.
Trejo, C.L. et al. "Extraction-free whole transcriptome gene expression analysis of FFPE sections and histology-directed subareas of tissue," *PLoS One* 14(2): e0212031.
Wu, L. et al. (Jun. 18, 2010). Bioinformatics and Biomedical Engineering (ICBBE), 2010 4th International Conference, IEEE, Piscataway, NJ, USA pp. 1-4.
Zeberg, H. et al. (Nov. 2020, e-published Sep. 30, 2020). "The major genetic risk factor for severe COVID-19 is inherited from Neanderthals," *Nature* 587(7835):610-612.

\* cited by examiner

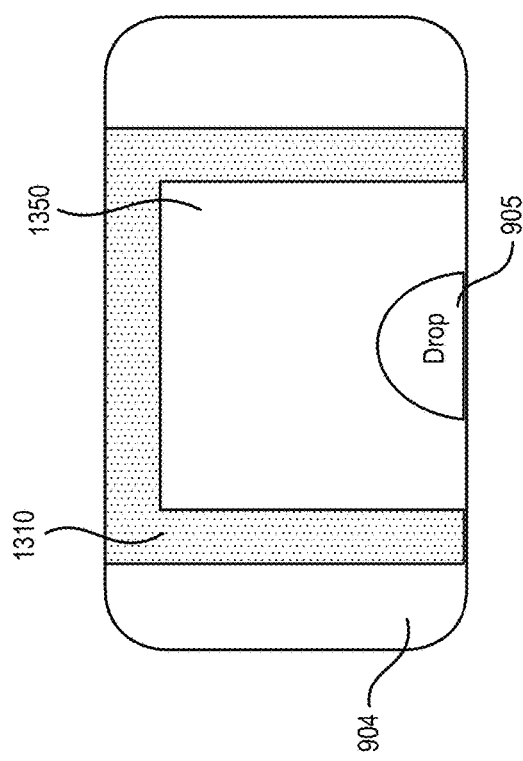
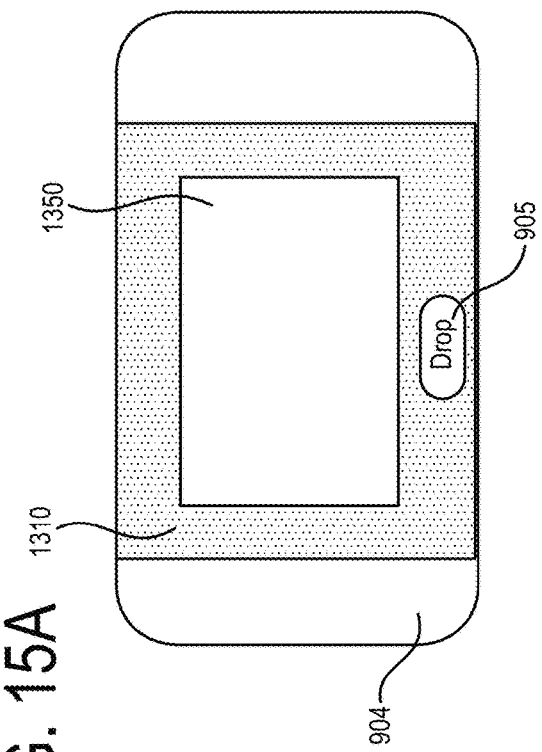
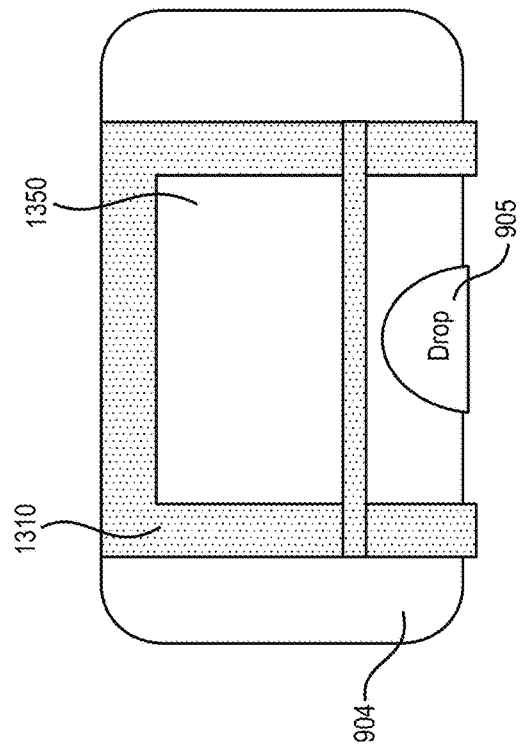
FIG. 15A
FIG. 15B
FIG. 15C

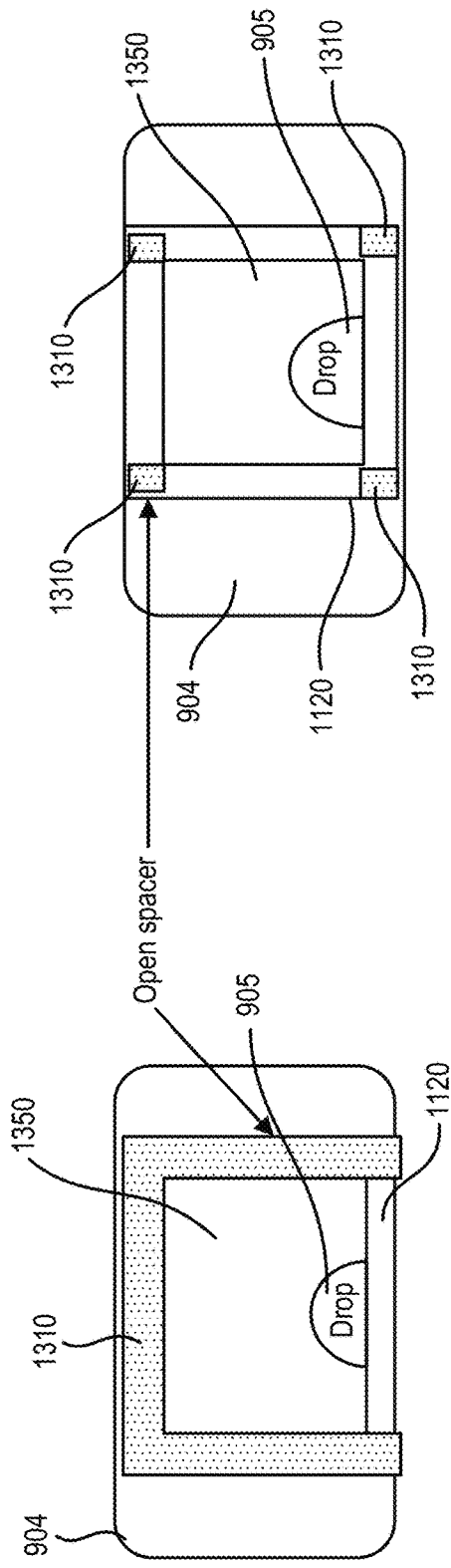
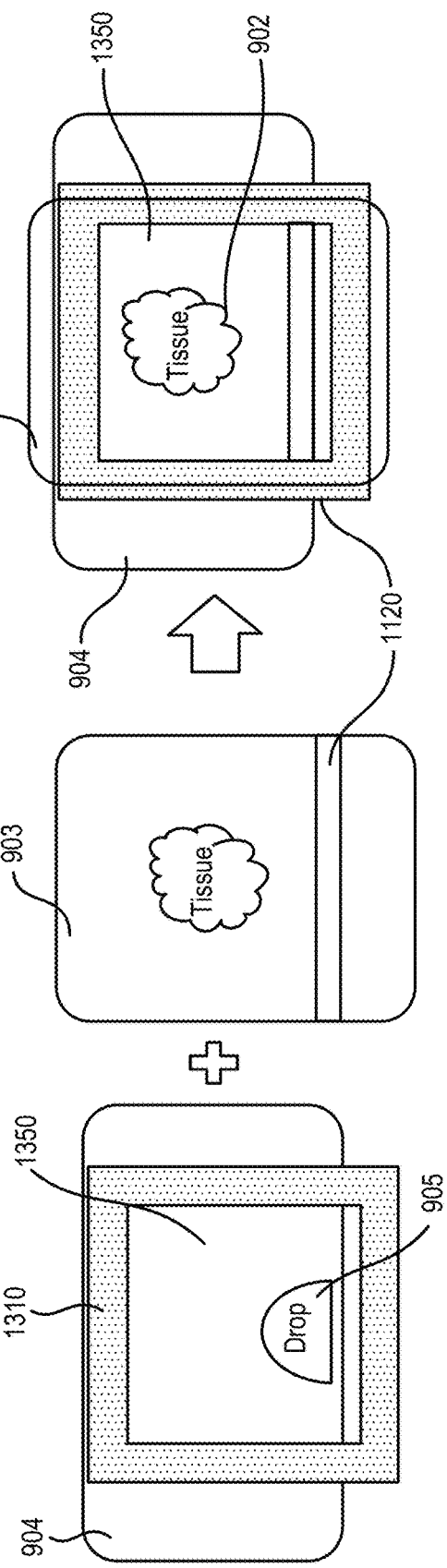

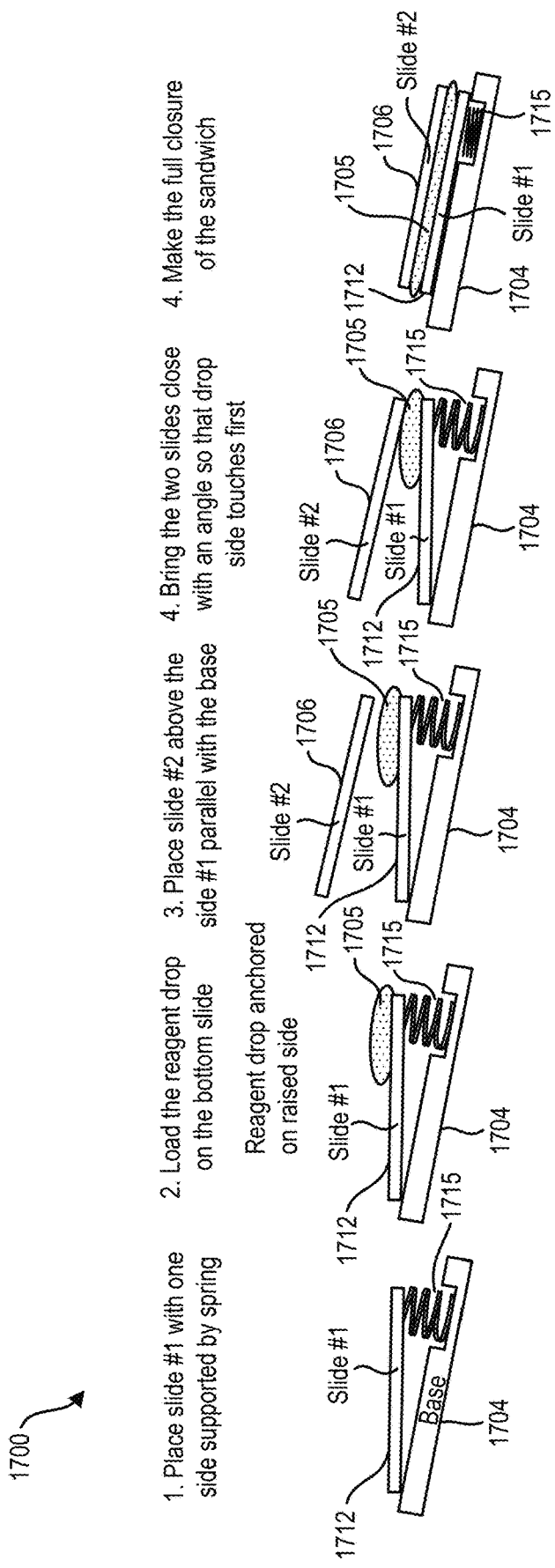

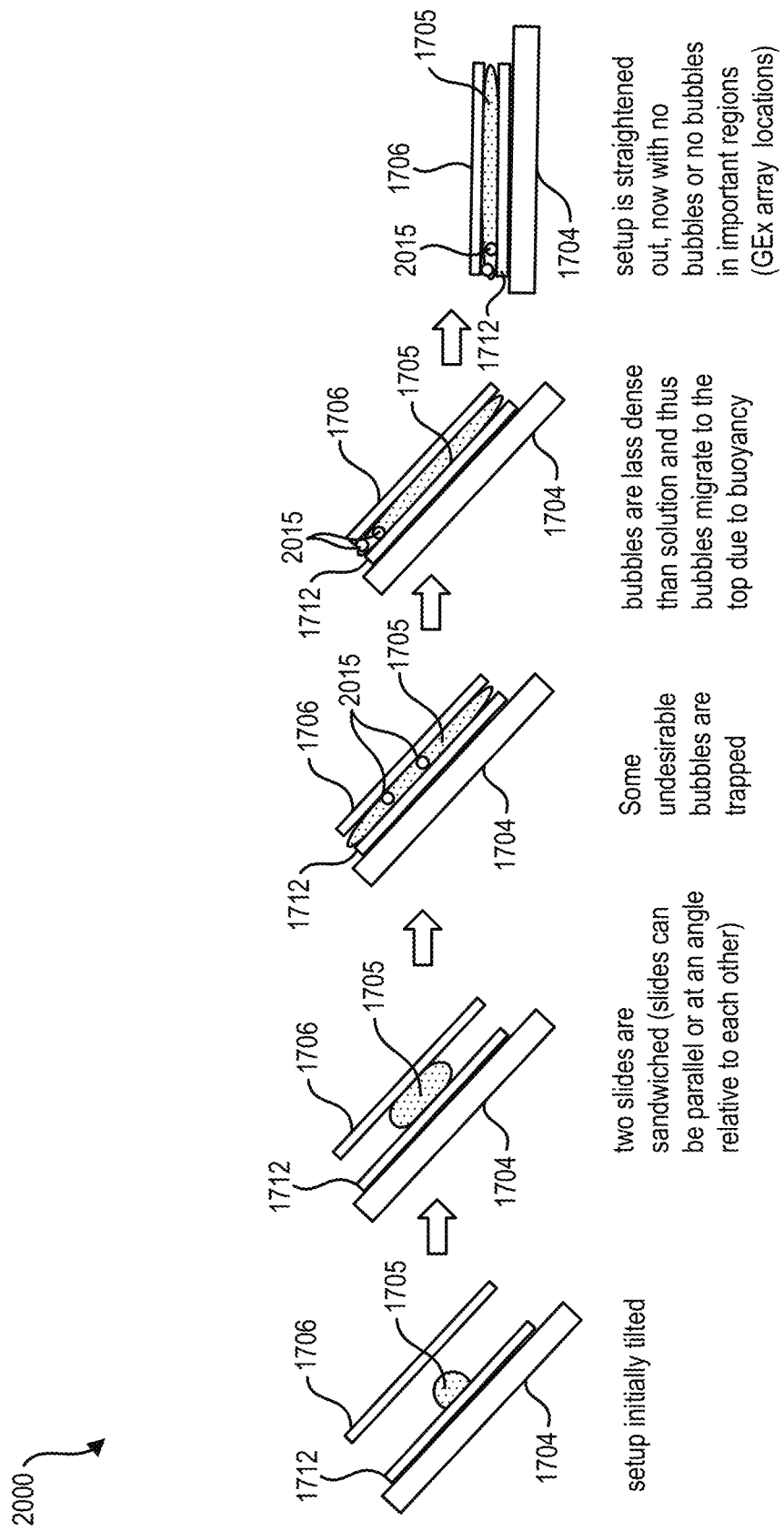

Step 1) Hydrophobic coating
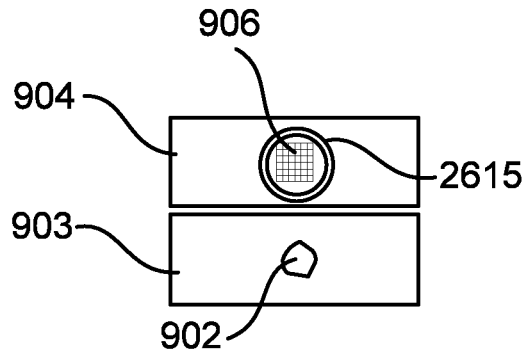
Step 2) Load permeabilization solution
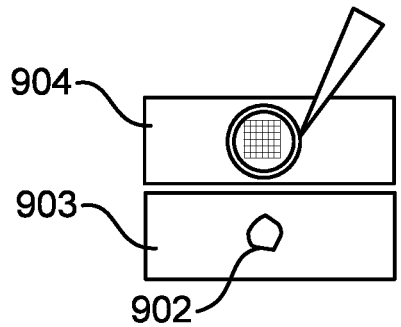
Step 3) Assemble sandwich
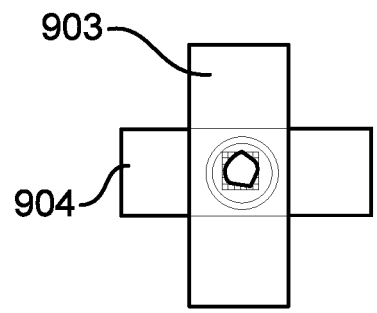
FIG. 26

| Analysis ID | Sample | Description | Permeabilization time | Permeabilization buffer | mm10 Median genes per spot (30k raw reads per spot) | mm10 Median umi counts per spot (30k raw reads per spot) |
|---|---|---|---|---|---|---|
| 1046321 | Mouse Brains (FF) | Non-sandwich control | 5 minutes | 30mM Tris (pH7.4); 5% Sarkosyl | 5194 | 17660 |
| 1046322 | | Permeabilization in sandwich assembly | 1 minutes | | 4592 | 13083 |
| 1046514 | | | | | 4072 | 14017 |
| 1046515 | | | | | 3758 | 13731 |

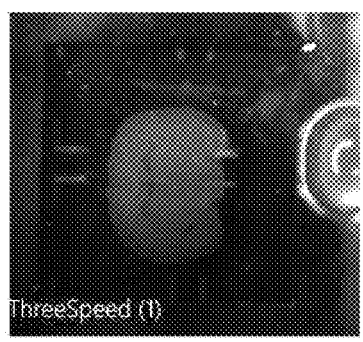 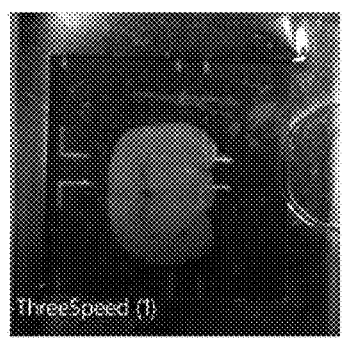 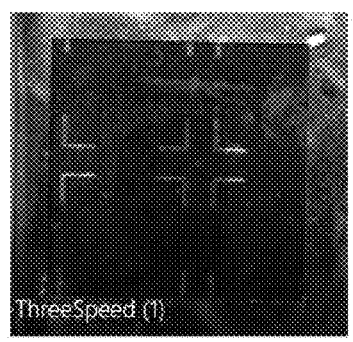
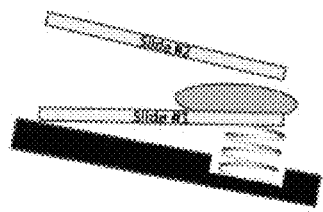 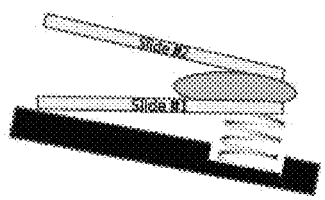 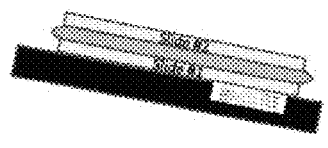
FIG. 38A  FIG. 38B  FIG. 38C

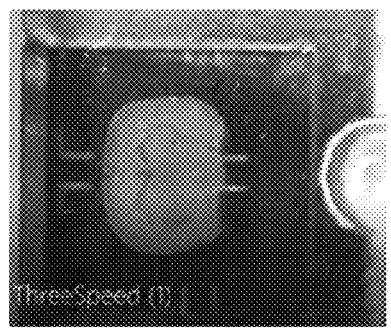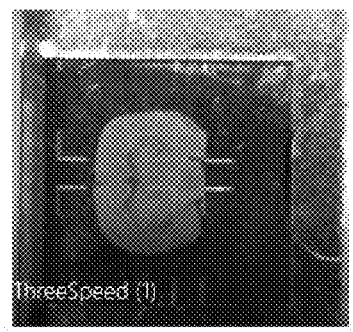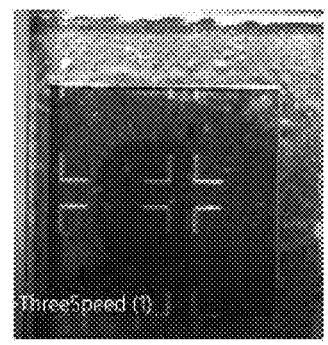
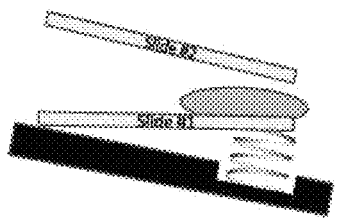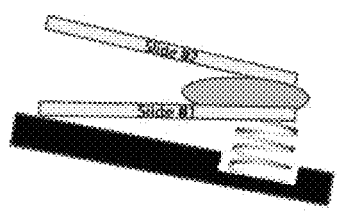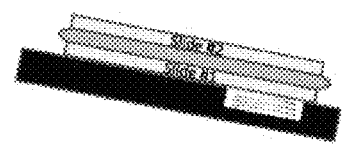
FIG. 39A  FIG. 39B  FIG. 39C Flow-Control-25uLCarb-HeaterOff_20210504_112933_sandwich_1fps_A

FLUID DELIVERY METHODS

CROSS REFERENCE TO RELATED APPLICATIONS

This application is a continuation of and claims priority to WO Application No. PCT/US21/36788 filed on Jun. 10, 2021, which claims the benefit of U.S. Provisional Application No. 63/037,417 filed on Jun. 10, 2020, U.S. Provisional Application No. 63/106,779 filed Oct. 28, 2020 and U.S. Provisional Application No. 63/080,514 filed Sep. 18, 2020. The entire contents of these applications are incorporated herein by reference in their entirety.

BACKGROUND

Cells within a tissue of a subject have differences in cell morphology and/or function due to varied analyte levels (e.g., gene and/or protein expression) within the different cells. The specific position of a cell within a tissue (e.g., the cell's position relative to neighboring cells or the cell's position relative to the tissue microenvironment) can affect, e.g., the cell's morphology, differentiation, fate, viability, proliferation, behavior, and signaling and cross-talk with other cells in the tissue.

Spatial heterogeneity has been previously studied using techniques that only provide data for a small handful of analytes in the context of an intact tissue or a portion of a tissue, or provide a lot of analyte data for single cells, but fail to provide information regarding the position of the single cell in a parent biological sample (e.g., tissue sample).

Analytes from a biological sample (e.g., within the biological sample) can be released through disruption (e.g., via permeabilization). The released analytes can migrate to an array for capture while preserving spatial context of the analytes. The released analytes can migrate, for example, via a reagent medium to the array. There exists a need for methods and systems that optimize fluidics behavior of the reagent medium (e.g., via improved fluid delivery), in order to preserve the spatial context of the released analytes for capture by the array.

SUMMARY

All publications, patents, patent applications, and information available on the internet and mentioned in this specification are herein incorporated by reference to the same extent as if each individual publication, patent, patent application, or item of information was specifically and individually indicated to be incorporated by reference. To the extent publications, patents, patent applications, and items of information incorporated by reference contradict the disclosure contained in the specification, the specification is intended to supersede and/or take precedence over any such contradictory material.

Analytes within a biological sample are generally released through disruption (e.g., permeabilization) of the biological sample. Various methods of disrupting a biological sample are known, including permeabilization of the cell membrane of the biological sample. Described herein are methods of delivering a fluid, including for example, a buffer or a permeabilization solutions having various detergents, buffers, proteases, and/or nucleases for different periods of time and at various temperatures.

Additionally, various methods of delivering fluids (e.g., a permeabilization solution) to a biological sample are described herein including the use of a substrate holder.

In one aspect, a method for delivering a fluid to biological sample disposed on a first substrate and an array disposed on a second substrate is provided. The method includes delivering the fluid to the first substrate and/or the second substrate. At least one of the first substrate and the second substrate including a spacer. The method further includes assembling, subsequent to the delivering, the chamber including the first substrate, the second substrate, the biological sample, and the spacer. The spacer is disposed between the first substrate and the second substrate. The spacer is configured to maintain the fluid within the chamber and maintain a separation distance between the first substrate and the second substrate. The spacer is positioned to at least partially surround an area on the first substrate on which the biological sample is disposed and/or at least partially surround the array disposed on the second substrate. The area of the first substrate, the spacer, and the second substrate at least partially encloses a volume including the biological sample.

In some variations of the method, the chamber includes a partially or fully sealed chamber. The second substrate includes a hydrophobic area positioned away from a region of interest. The hydrophobic area may be configured to remove bubbles in the fluid from the chamber. The region of interest may include an area where the biological sample and the array overlap. The hydrophobic area may include a hydrophobic coating. The separation distance may include a distance of at least 2 μm. The separation distance may include a distance between about 5 μm to 25 μm. the second substrate may include the spacer. The first substrate may include the spacer. The method may further include applying, prior to delivering the fluid, a hydrophilic coating to the first substrate and/or the second substrate. The fluid may include a wetting agent. The fluid may include one or more permeabilization reagent(s). The spacer may include an air permeable spacer portion configured to vent a bubble from the fluid. The method may further include generating a vibration to the first substrate and/or the second substrate. Delivering the fluid to the first substrate and/or the second substrate may include adjusting a humidity of the chamber. Delivering the fluid to the first substrate and/or the second substrate may include generating a vacuum to a region proximate to the first substrate and/or the second substrate. Delivering the fluid to the first substrate and/or the second substrate may include delivering the fluid to a region of the second substrate. The spacer may include three sides partially surrounding the fluid. Delivering the fluid to the first substrate and/or the second substrate may include delivering the fluid to a region of the second substrate. The region may be disposed outside an enclosed area of the second substrate. The enclosed area may be formed by the spacer. Delivering the fluid to the first substrate and/or the second substrate may include delivering the fluid to a region of the spacer. The region disposed outside an enclosed area of the second substrate. The enclosed area may be formed by the spacer. Assembling the chamber may include positioning, responsive to the delivering, the first substrate at an angle such that a dropped side of the first substrate contacts at least a portion of the fluid when the first substrate and the second substrate are within a threshold distance along an axis orthogonal to the second substrate. The dropped side may urge the fluid toward the three sides partially surrounding the fluid. The chamber may include a hydrophobic pattern at least partially surrounding the fluid and positioned to at least partially surround the area on the first substrate and/or the array disposed on the second substrate. The spacer may be formed from a uniform thickness material. The spacer may be formed from a material with a variable thickness. The spacer may be printed on the first substrate and/or the second substrate. The spacer may include a photoresist pattern. The spacer may include a beveled edge on one or more sides of the spacer.

In one aspect, a system is provided. The system includes a first substrate including a coating for adhering a biological sample. The system further includes a second substrate including an array. The system further includes a spacer disposed between the first substrate and the second substrate and configured to maintain a fluid within a chamber comprising the first substrate, the second substrate, the biological sample, and the spacer, the spacer further configured to maintain a separation distance between the first substrate and the second substrate, the spacer positioned to at least partially surround the biological sample on the first substrate and/or at least partially surround the array disposed on the second substrate.

In one aspect, a kit is provided. The kit includes a second substrate including an array. The second substrate further includes a spacer surrounding the array.

In another aspect, a kit is provided. The kit includes a first substrate including a biological sample. The first substrate further includes a spacer surrounding the biological sample.

In one aspect, a kit is provided. The kit includes a spacer configured to be disposed between a first substrate and the second substrate. The kit further includes instructions for use according to a method described herein.

Provided herein are methods for delivering a fluid to a biological sample disposed on an area of a first substrate and an array disposed on a second substrate, comprising: assembling a partially sealed chamber comprising the first substrate, the second substrate, the biological sample, and a gasket, wherein the gasket is disposed between the first substrate and second substrate, and surrounds the area on the first substrate and/or the array disposed on the second substrate, wherein the area of the first substrate, the gasket, and the second substrate at least partially encloses a volume comprising the biological sample. The method further comprises delivering the fluid to the partially sealed chamber through one or more apertures of the gasket, thereby delivering the fluid to the array and the biological sample.

In some embodiments, the method further includes prior to assembling, providing the biological sample on the area of the first substrate and the array disposed on the second substrate.

In some embodiments, the first substrate, the second substrate, or both comprises a glass surface. In some embodiments, the glass surface is a glass slide. In some embodiments, the first substrate and the second substrate are axially aligned. In some embodiments, the first substrate and the second substrate are in a cross-configuration.

In some embodiments, delivering the fluid includes flowing the fluid through the one or more apertures of the gasket. Delivering the fluid may include injecting the fluid through the one or more apertures of the gasket using a syringe. In some embodiments, the syringe is configured to interface or lock with one of the one or more apertures of the gasket. In some embodiments, delivering the fluid may be at a temperature of about 5° C. to about 80° C.

In some embodiments, the method further includes permeabilizing the biological sample. In some embodiments, the second substrate may include one or more dried permeabilization reagent(s) disposed thereon. In some embodiments, the fluid solubilizes the one or more dried permeabilization reagent(s). In some embodiments, the fluid comprises one or more permeabilization reagent(s). In some embodiments, the permeabilizing is performed for about 1 minute to about 90 minutes. In some embodiments, the permeabilizing may include heating the first substrate, the second substrate, or both the first substrate and the second substrate. In some embodiments, the permeabilizing of the biological sample may be controlled by modulating the temperature of the fluid. In some embodiments, modulating the temperature of the fluid may include heating the fluid to at least about 40° C.

In some embodiments, the one or more permeabilization reagent(s) may be selected from the group consisting of: a detergent, an enzyme, and a buffer. In some embodiments, the one or more dried permeabilization reagent(s) comprises one or both of a detergent and an enzyme. In some embodiments, the detergent comprises one or more of SDS, N-lauroylsarcosine, saponin, or any combination thereof. In some embodiments, the enzyme may include one or more of proteinase K, pepsin, collagenase, trypsin, or any combination thereof. In some embodiments, the buffer may include TE, TAE, TBE, or PBS.

In some embodiments, delivering the one or more permeabilization reagent(s) may include delivering the detergent, the enzyme, and the buffer sequentially in any order. In some embodiments, delivering the one or more permeabilization reagent(s) may include delivering the detergent, the enzyme, and the buffer as a mixture. In some embodiments, delivering may include delivering the one or more permeabilization reagent(s) two or more times to the partially sealed chamber. In some embodiments, the one or more apertures may include a hydrophobic coating.

Also provided herein are methods for delivering a fluid to a biological sample disposed on an area of a first substrate and an array disposed on a second substrate, the method comprising: assembling a partially sealed chamber comprising the first substrate, the second substrate, the biological sample, and a gasket, wherein a gasket is disposed between the first substrate and second substrate, and surrounds the area on the first substrate and/or the array disposed on the second substrate, wherein the first substrate, the gasket, and the second substrate at least partially encloses a volume comprising the biological sample. The method further comprising delivering the fluid to the partially sealed chamber through one or more via-holes in the first substrate or one or more via-holes in the second substrate, thereby delivering the fluid to the array and the biological sample.

In some embodiments, the method further includes prior to assembling, providing the biological sample on the area of the first substrate and the array disposed on the second substrate.

In some embodiments, the first substrate, the second substrate, or both comprises a glass surface. In some embodiments, the glass surface is a glass slide. In some embodiments, the first substrate and the second substrate are axially aligned. In some embodiments, the first substrate and the second substrate are in a cross-configuration.

In some embodiments, delivering the fluid includes flowing the fluid through via-holes in the first substrate. In some embodiments, delivering the fluid comprises flowing the fluid through one or more via-holes in the second substrate. Delivering the fluid may include injecting the fluid through the one or more via-holes using a syringe. In some embodiments, the syringe is configured to interface or lock with one of the one or more via-holes in the first substrate. In some embodiments, the syringe is configured to interface or lock with one of the one or more via-holes in the second substrate.

In some embodiments, delivering the fluid comprises delivering the fluid to one or more via-holes in the first substrate by capillary flow. In some embodiments, delivering the fluid comprises delivering the fluid to one or more via-holes in the second substrate by capillary flow.

In some embodiments of delivering a fluid to a biological sample disposed on an area of a first substrate and an array disposed on a second substrate, delivering the fluid is at temperature of about 5° C. to about 80° C.

In some embodiments, the method includes permeabilizing the biological sample. In some embodiments, the substrate comprises one or more dried permeabilization reagent(s) disposed thereon. In some embodiments, the fluid solubilizes the one or more dried permeabilization reagent(s). In some embodiments, the fluid comprises one or more permeabilization reagent(s). In some embodiments, the permeabilizing is performed for about 1 minute to about 90 minutes. In some embodiments, the permeabilizing comprises heating the first substrate, the second substrate, or both the first substrate and the second substrate. In some embodiments, the permeabilizing of the biological sample is controlled by modulating the temperature of the fluid. In some embodiments, modulating the temperature of the fluid comprises heating the fluid to at least about 40° C.

In some embodiments, the one or more permeabilization reagent(s) may be selected from the group consisting of: a detergent, an enzyme, and a buffer. In some embodiments, the one or more dried permeabilization reagent(s) comprises one or both of a detergent and an enzyme. In some embodiments, the detergent comprises one or more of SDS, N-lauroylsarcosine, saponin, or any combination thereof. In some embodiments, the enzyme may include one or more of proteinase K, pepsin, collagenase, trypsin, or any combination thereof. In some embodiments, the buffer may include TE, TAE, TBE, or PBS.

In some embodiments, delivering the one or more permeabilization reagent(s) may include delivering the detergent, the enzyme, and the buffer sequentially in any order. In some embodiments, delivering the one or more permeabilization reagent(s) may include delivering the detergent, the enzyme, and the buffer as a mixture. In some embodiments, delivering may include delivering the one or more permeabilization reagent(s) two or more times to the partially sealed chamber.

Also provided herein are method for delivering a fluid to a biological sample disposed on an area of a first substrate and an array disposed on a second substrate, the method comprising delivering a fluid to the area on the first substrate, wherein a virtual gasket surrounds the area on the first substrate and contains the fluid within the area; and assembling the second substrate with the first substrate, thereby delivering the fluid to the array and the biological sample.

Also provided herein are methods for delivering a fluid to a biological sample disposed on an area of a first substrate and an array disposed on a second substrate, the method comprising: delivering a fluid to the area on the second substrate, wherein a virtual gasket surrounds the area on the second substrate and contains the fluid on the array; and assembling the first substrate with the second substrate, thereby delivering the fluid to the array and the biological sample.

In some embodiments, prior to assembling, providing the biological sample on the area of the first substrate and the array disposed on the second substrate.

In some embodiments, the first substrate, the second substrate, or both comprises a glass surface. In some embodiments, the glass surface is a glass slide.

In some embodiments, the first substrate and the second substrate are axially aligned. In some embodiments, the first substrate and the second substrate are in a cross configuration.

In some embodiments, the virtual gasket comprises a hydrophobic coating. In some embodiments, the virtual gasket includes one or more apertures. In some embodiments, the hydrophobic coating is applied with a stamp. In some embodiments, the hydrophobic coating is a paraffin-based wax. In some embodiments, the hydrophobic coating covers the all, or a portion of, the first substrate outside the area on the first substrate. In some embodiments, the hydrophobic coating covers all, or a portion of, the second substrate outside the array on the second substrate. In some embodiments, the hydrophobic coating is applied in a pattern. In some embodiments, the hydrophobic coating comprises electrowetting.

In some embodiments, delivering the fluid comprises delivering the fluid to the first substrate. In some embodiments, delivering the fluid comprises delivering the fluid to the second substrate. In some embodiments, delivering the fluid comprises flowing the fluid through the one or more apertures of the virtual gasket. In some embodiments, delivering the fluid comprises injecting the fluid through the one or more apertures of the gasket with a syringe.

In some embodiments, the syringe is configured to interface or lock with one of the one or more apertures of the virtual gasket. In some embodiments, delivering the fluid comprises flowing the fluid by capillary flow. In some embodiments, delivering the fluid is at temperature of about 5° C. to about 80° C.

In some embodiments, the method includes permeabilizing the biological sample. In some embodiments, the second substrate comprises one or more dried permeabilization reagent(s) disposed thereon. In some embodiments, the fluid solubilizes the one or more dried permeabilization reagent(s). In some embodiments, the fluid comprises one or more permeabilization reagent(s). In some embodiments, the permeabilizing is performed for about 1 minute to about 90 minutes. In some embodiments, the permeabilizing comprises heating the first substrate, the second substrate, or both the first substrate and the second substrate. In some embodiments, the permeabilizing of the biological sample is controlled by modulating the temperature of the fluid. In some embodiments, modulating the temperature of the fluid comprises heating to at least about 40° C.

In some embodiments, the one or more permeabilization reagent(s) is/are selected from the group consisting of: a detergent, an enzyme, and a buffer. In some embodiments, the one or more dried permeabilization reagent(s) comprises one or both of a detergent and an enzyme. In some embodiments, the detergent comprises one or more of SDS, N-lauroylsarcosine, saponin, or any combination thereof. In some embodiments, the enzyme comprises one or more of proteinase K, pepsin, collagenase, trypsin, or any combination thereof. In some embodiments, the buffer comprises TE, TAE, TBE, and PBS. In some embodiments, delivering the one or more permeabilization reagent(s) comprises delivering the detergent, the enzyme, and the buffer sequentially in any order. In some embodiments, delivering the one or more permeabilization reagent(s) comprises delivering the detergent, the enzyme, and the buffer as a mixture. In some embodiments, delivering comprises delivering the one or more permeabilization reagent(s) two or more times to the partially sealed chamber.

In some embodiments, patterning the hydrophobic coating surrounds one or more regions of interest in the biological sample.

In some embodiments, the method includes imaging the biological sample. In some embodiments, the biological sample is a tissue section. In some embodiments, the biological sample is a fresh-frozen tissue section. In some embodiments, the biological sample is a fixed biological sample. In some embodiments, the fixed biological sample is a formalin-fixed paraffin-embedded biological sample.

In some embodiments, the array comprises a plurality of features. In some embodiments, the array comprises about 5,000 features. In some embodiments, a feature of the plurality of features is selected from the group consisting of a bead, a spot, an inkjet spot, a well, a hydrogel pad, and a nanoparticle. In some embodiments, a plurality of capture probes are attached to the bead. In some embodiments, a capture probe of the plurality of capture probes comprises (i) a capture domain; and (ii) a spatial barcode unique to the feature. In some embodiments, the capture domain of the capture probe comprises a poly(T) sequence. In some embodiments, the capture probe includes one or more of: a functional domain, a cleavage domain, a unique molecular identifier, or any combination thereof.

Also provided herein are kits including a first substrate comprising a coating for adhering a biological sample; a second substrate comprising an array; and a gasket. In some kits, the gasket comprises no apertures. In some embodiments, the gasket comprises one aperture for fluid delivery. In some kits, the gasket comprises two apertures for fluid delivery. In some kits, the first substrate comprises one or more via-holes for fluid delivery. In some kits, the second substrate comprises one or more via-holes for fluid delivery. In some kits, the kit includes a paraffin-based crayon. In some kits, the kit includes a hydrophobic coating stamp. In some kits, the kit includes a reverse transcriptase and a nuclease. In some kits, the kit includes one or more permeabilization agent(s). In some kits, the first substrate, the second substrate, and the gasket are assembled into a partially sealed chamber. In some kits, the kit includes instructions for assembling a partially sealed chamber.

Also provided herein is a method for delivering a fluid to a biological sample disposed on an area of a first substrate and an array disposed on a second area of a second substrate. The method includes assembling a partially sealed chamber comprising the first substrate, the second substrate, the biological sample, and a spacer, wherein the spacer is disposed between the first substrate and second substrate, and surrounds the area on the first substrate and/or the array disposed on the second substrate, wherein the area of the first substrate, the spacer, and the second substrate at least partially encloses a volume comprising the biological sample. The method further includes delivering the fluid to the partially sealed chamber, thereby delivering the fluid to the array and the biological sample.

In some variations of the method, the method includes prior to assembling, providing the biological sample on the area of the first substrate and providing the array disposed on the second substrate. The first substrate, the second substrate, or both may include a glass surface. The glass surface may include a glass slide. The first substrate and the second substrate may be axially aligned. The first substrate and the second substrate may be in a cross configuration. Delivering the fluid comprises flowing the fluid through the one or more apertures of the spacer. In some embodiments, delivering the fluid comprises injecting the fluid through the one or more apertures of the spacer using a syringe. The syringe may be configured to interface or lock with one of the one or more apertures of the spacer. Delivering the fluid may be at a temperature of about 5° C. to about 80° C. The method may include permeabilizing the biological sample. The second substrate may include one or more dried permeabilization reagent(s) disposed thereon. The fluid may solubilize the one or more dried permeabilization reagent(s). The fluid may include one or more permeabilization reagent(s). The permeabilizing may be performed for about 1 minute to about 90 minutes. The permeabilizing may include heating the first substrate, the second substrate, or both the first substrate and the second substrate. The permeabilizing of the biological sample may be controlled by modulating the temperature of the fluid. Modulating the temperature of the fluid may include heating to at least about 40° C. The one or more permeabilization reagent(s) may be selected from the group consisting of: a detergent, an enzyme, and a buffer. The one or more dried permeabilization reagent(s) may include one or both of a detergent and an enzyme. The detergent may include one or more of SDS, N-lauroylsarcosine, saponin, or any combination thereof. The enzyme may include one or more of proteinase K, pepsin, collagenase, trypsin, or any combination thereof. The buffer may include TE, TAE, TBE, and PBS. Delivering the one or more permeabilization reagent(s) may include delivering the detergent, the enzyme, and the buffer sequentially in any order. Delivering the one or more permeabilization reagent(s) may include delivering the detergent, the enzyme, and the buffer as a mixture. Delivering may include delivering the one or more permeabilization reagent(s) two or more times to the partially sealed chamber. The one or more apertures may include a hydrophobic coating.

Also provided herein is a method for delivering a fluid to a biological sample disposed on an area of a first substrate and an array disposed on a second area of a second substrate. The method includes delivering a fluid to the second area on the second substrate. A spacer surrounds the second area on the second substrate and contains the fluid on the array. The method further includes assembling the first substrate with the second substrate, thereby delivering the fluid to the array and the biological sample.

In some variations of the method, the method includes, prior to assembling, providing the biological sample on the area of the first substrate and providing the array disposed on the second substrate. The first substrate, the second substrate, or both may include a glass surface. The glass surface may include a glass slide. The first substrate and the second substrate may be axially aligned. The first substrate and the second substrate may be in a cross configuration. Delivering the fluid may include flowing the fluid through one or more via-holes in the first substrate. Delivering the fluid may include flowing the fluid through one or more via-holes in the second substrate. In some embodiments, delivering the fluid comprises injecting the fluid through the one or more via-holes using a syringe. The syringe may be configured to interface or lock with one of the one or more via-holes in the first substrate. The syringe may be configured to interface or lock with one of the one or more via-holes in the second substrate. Delivering the fluid may include delivering the fluid to one or more via-holes in the first substrate by capillary flow. Delivering the fluid may include delivering the fluid to one or more via-holes in the second substrate by capillary flow. Delivering the fluid may be at a temperature of about 5° C. to about 80° C. The method may include permeabilizing the biological sample. The second substrate may include one or more dried permeabilization reagent(s) disposed thereon. The fluid may solubilize the one or more dried permeabilization reagent(s). The fluid may include one or more permeabilization reagent(s). The permeabilizing may be performed for about 1 minute to about 90 minutes. The permeabilizing may include heating the first substrate, the second substrate, or both the first substrate and the second substrate. The permeabilizing of the biological sample may be controlled by modulating the temperature of the fluid. Modulating the temperature of the fluid may include heating to at least about 40° C. The one or more permeabilization reagent(s) may be selected from the group consisting of: a detergent, an enzyme, and a buffer. The one or more dried permeabilization reagent(s) may include one or both of a detergent and an enzyme. The detergent may include one or more of SDS, N-lauroylsarcosine, saponin, or any combination thereof. The enzyme may include one or more of proteinase K, pepsin, collagenase, trypsin, or any combination thereof. The buffer may include TE, TAE, TBE, and PBS. Delivering the one or more permeabilization reagent(s) may include delivering the detergent, the enzyme, and the buffer sequentially in any order. Delivering the one or more permeabilization reagent(s) may include delivering the detergent, the enzyme, and the buffer as a mixture. Delivering may include delivering the one or more permeabilization reagent(s) two or more times to the partially sealed chamber.

Also provided herein is a system. The system comprising a first substrate for adhering a biological sample. The system further comprising a second substrate comprising an array. The system further comprising a spacer disposed between the first substrate and the second substrate and configured to maintain a fluid within a chamber comprising the first substrate, the second substrate, the biological sample, and the spacer, the spacer further configured to maintain a separation distance between the first substrate and the second substrate, the spacer positioned to at least partially surround the biological sample on the first substrate and/or the array disposed on the second substrate.

In some variations of the system, the first substrate comprises the biological sample mounted thereon. The system of any one of the preceding aspects may further include a sample holder. In some embodiments, the sample holder comprises a first member comprising a first retaining mechanism configured to retain the first substrate disposed in a first plane, a second member comprising a second retaining mechanism configured to retain the second substrate disposed in the second plane, and an alignment mechanism connected to one or both of the first member and the second member, and configured to align the first and second members along the first plane and/or the second plane such that the sample contacts at least a portion of the reagent medium when the first and second members are aligned and within a threshold distance along an axis orthogonal to the second plane. The sample holder further comprises an adjustment mechanism configured to move the second member along the axis orthogonal to the second plane and/or move the first member along an axis orthogonal to the first plane to assemble the chamber comprising the first substrate, the second substrate, the biological sample, and the spacer when the first and second members are aligned and within the threshold distance along an axis orthogonal to the second plane.

In some variations, the systems provided herein further comprise a sample holder. For example, the system comprising: a first substrate comprising a coating for adhering a biological sample; a second substrate comprising an array; and a spacer disposed between the first substrate and the second substrate may further comprise the sample holder.

Further, the system comprising: a first substrate for adhering a biological sample; a second substrate comprising an array; and a spacer disposed between the first substrate and the second substrate may further comprise the sample holder. The sample holder comprises a first member comprising a retaining mechanism that retains the first substrate, a second member comprising a second retaining mechanism that retains the second substrate, and an alignment mechanism that is connected to at least one of first and second members or to both first and second members and configured to align the first and second members such that the biological sample (or a portion thereof) on the first substrate is aligned with and contacts the array of the second substrate.

The term "each," when used in reference to a collection of items, is intended to identify an individual item in the collection but does not necessarily refer to every item in the collection, unless expressly stated otherwise, or unless the context of the usage clearly indicates otherwise.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. Similarly, the use of these terms in the specification does not by itself connote any required priority, precedence, or order.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

Various embodiments of the features of this disclosure are described herein. However, it should be understood that such embodiments are provided merely by way of example, and numerous variations, changes, and substitutions can occur to those skilled in the art without departing from the scope of this disclosure. It should also be understood that various alternatives to the specific embodiments described herein are also within the scope of this disclosure.

DESCRIPTION OF DRAWINGS

The following drawings illustrate certain embodiments of the features and advantages of this disclosure. These embodiments are not intended to limit the scope of the appended claims in any manner. Like reference symbols in the drawings indicate like elements.

FIGS. 15A-15C show example configurations for that one or more spacers disposed on the first substrate and/or the second substrate in accordance with some example implementations.

FIGS. 16A-16E depict example configurations of the one or more spacers combined with one or more hydrophobic areas in accordance with some example implementations.

FIGS. 17A-17E depict an example workflow for an angled sandwich assembly in accordance with some example implementations.

FIGS. 20A-20E show an example workflow for an angled sandwich assembly in accordance with some example implementations.

FIG. 26 shows an exemplary fluid delivery scheme.

FIGS. 38A-C depict an example fast closing speed condition for a sandwich assembly using angled closure in accordance with some example implementations.

FIGS. 39A-C depict an example medium closing speed condition for a sandwich assembly using angled closure in accordance with some example implementations.

DETAILED DESCRIPTION

I. Introduction

Figure 1:
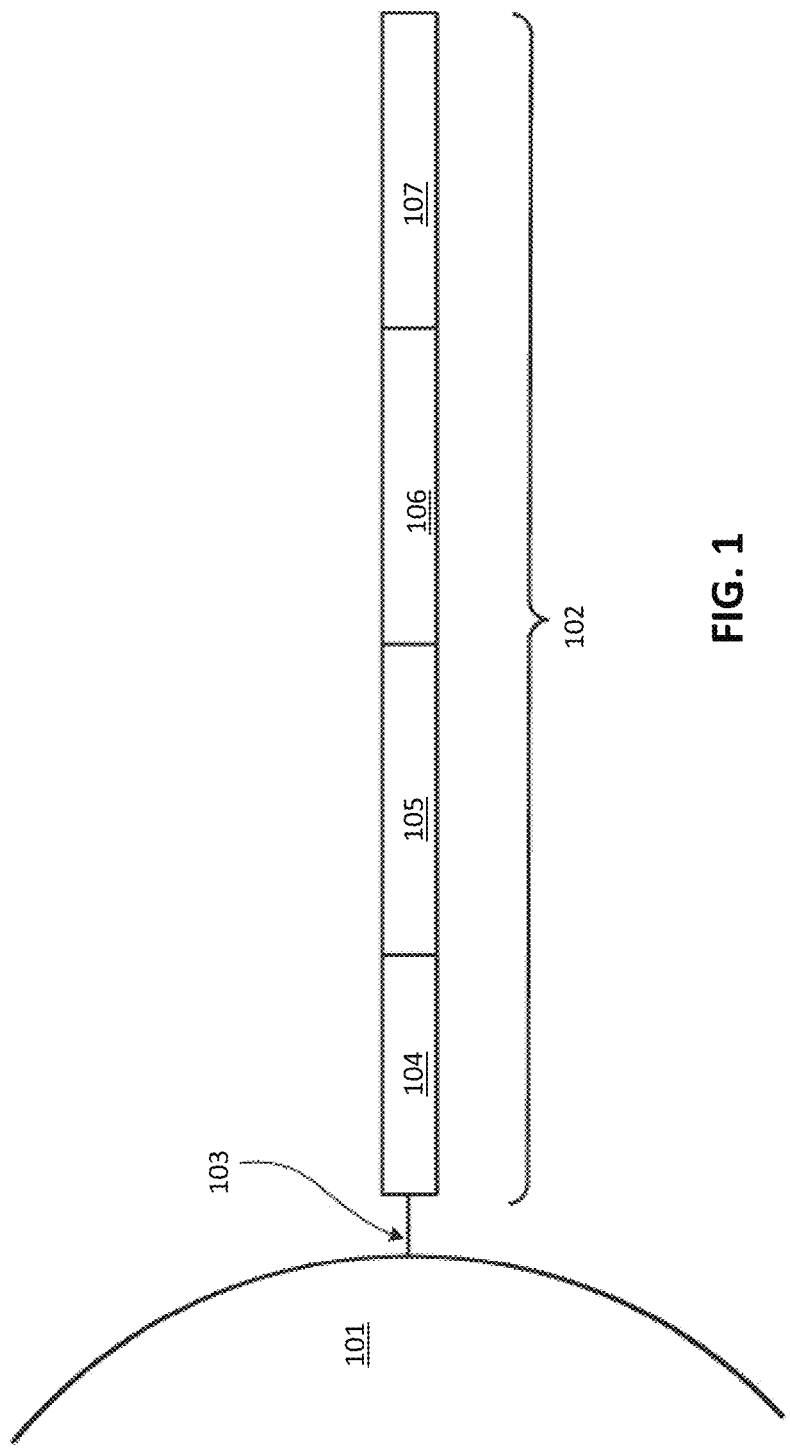
FIG. 1 is a schematic diagram showing an example of a barcoded capture probe, as described herein.

This disclosure describes apparatus, systems, methods, and compositions for spatial analysis of biological samples. This section describes certain general terminology, analytes, sample types, and preparative steps that are referred to in later sections of the disclosure. For example, the terms and phrases: spatial analysis, barcode, nucleic acid, nucleotide, probe, target, oligonucleotide, polynucleotide, subject, genome, adaptor, adapter, tag, hybridizing, hybridize, annealing, anneal, primer, primer extension, proximity ligation, nucleic acid extension, polymerase chain reaction (PCR) amplification, antibody, affinity group, label, detectable label, optical label, template switching oligonucleotide, splint oligonucleotide, analytes, biological samples, general spatial array-based analytical methodology, spatial analysis methods, immunohistochemistry and immunofluorescence, capture probes, substrates, arrays, analyte capture, partitioning, analysis of captured analytes, quality control, and/or the like are described in more detail in PCT Patent Application Publication No. WO2020/123320, the entire contents of which are incorporated herein by reference.\

(a) Spatial Analysis

Tissues and cells can be obtained from any source. For example, tissues and cells can be obtained from single-cell or multicellular organisms (e.g., a mammal). Tissues and cells obtained from a mammal, e.g., a human, often have varied analyte levels (e.g., gene and/or protein expression) which can result in differences in cell morphology and/or function. The position of a cell or a subset of cells (e.g., neighboring cells and/or non-neighboring cells) within a tissue can affect, e.g., the cell's fate, behavior, morphology, and signaling and cross-talk with other cells in the tissue. Information regarding the differences in analyte levels (gene and/or protein expression) within different cells in a tissue of a mammal can also help physicians select or administer a treatment that will be effective and can allow researchers to identify and elucidate differences in cell morphology and/or cell function in the single-cell or multicellular organisms (e.g., a mammal) based on the detected differences in analyte levels within different cells in the tissue. Differences in analyte levels within different cells in a tissue of a mammal can also provide information on how tissues (e.g., healthy and diseased tissues) function and/or develop. Differences in analyte levels within different cells in a tissue of a mammal can also provide information of different mechanisms of disease pathogenesis in a tissue and mechanism of action of a therapeutic treatment within a tissue. Differences in analyte levels within different cells in a tissue of a mammal can also provide information on drug resistance mechanisms and the development of the same in a tissue of a mammal. Differences in the presence or absence of analytes within different cells in a tissue of a multicellular organism (e.g., a mammal) can provide information on drug resistance mechanisms and the development of the same in a tissue of a multicellular organism.

The spatial analysis methodologies herein provide for the detection of differences in an analyte level (e.g., gene and/or protein expression) within different cells in a tissue of a mammal or within a single cell from a mammal. For example, spatial analysis methodologies can be used to detect the differences in analyte levels (e.g., gene and/or protein expression) within different cells in histological slide samples, the data from which can be reassembled to generate a three-dimensional map of analyte levels (e.g., gene and/or protein expression) of a tissue sample obtained from a mammal, e.g., with a degree of spatial resolution (e.g., single-cell resolution).

Spatial heterogeneity in developing systems has typically been studied via RNA hybridization, immunohistochemistry, fluorescent reporters, or purification or induction of pre-defined subpopulations and subsequent genomic profiling (e.g., RNA-seq). Such approaches, however, rely on a relatively small set of pre-defined markers, therefore introducing selection bias that limits discovery. These prior approaches also rely on a priori knowledge. RNA assays traditionally relied on staining for a limited number of RNA species. In contrast, single-cell RNA-sequencing allows for deep profiling of cellular gene expression (including non-coding RNA), but the established methods separate cells from their native spatial context.

Spatial analysis methodologies described herein provide a vast amount of analyte level and/or expression data for a variety of multiple analytes within a sample at high spatial resolution, e.g., while retaining the native spatial context. Spatial analysis methods include, e.g., the use of a capture probe including a spatial barcode (e.g., a nucleic acid sequence that provides information as to the position of the capture probe within a cell or a tissue sample (e.g., mammalian cell or a mammalian tissue sample) and a capture domain that is capable of binding to an analyte (e.g., a protein and/or nucleic acid) produced by and/or present in a cell. As described herein, the spatial barcode can be a nucleic acid that has a unique sequence, a unique fluorophore or a unique combination of fluorophores, a unique amino acid sequence, a unique heavy metal or a unique combination of heavy metals, or any other unique detectable agent. The capture domain can be any agent that is capable of binding to an analyte produced by and/or present in a cell (e.g., a nucleic acid that is capable of hybridizing to a nucleic acid from a cell (e.g., an mRNA, genomic DNA, mitochondrial DNA, or miRNA), a substrate including an analyte, a binding partner of an analyte, or an antibody that binds specifically to an analyte). A capture probe can also include a nucleic acid sequence that is complementary to a sequence of a universal forward and/or universal reverse primer. A capture probe can also include a cleavage site (e.g., a cleavage recognition site of a restriction endonuclease), a photolabile bond, a thermosensitive bond, or a chemical-sensitive bond.

The binding of an analyte to a capture probe can be detected using a number of different methods, e.g., nucleic acid sequencing, fluorophore detection, nucleic acid amplification, detection of nucleic acid ligation, and/or detection of nucleic acid cleavage products. In some examples, the detection is used to associate a specific spatial barcode with a specific analyte produced by and/or present in a cell (e.g., a mammalian cell).

Capture probes can be, e.g., attached to a surface, e.g., a solid array, a bead, or a coverslip. In some examples, capture probes are not attached to a surface. In some examples, capture probes can be encapsulated within, embedded within, or layered on a surface of a permeable composition (e.g., any of the substrates described herein). For example, capture probes can be encapsulated or disposed within a permeable bead (e.g., a gel bead). In some examples, capture probes can be encapsulated within, embedded within, or layered on a surface of a substrate (e.g., any of the exemplary substrates described herein, such as a hydrogel or a porous membrane).

In some examples, a cell or a tissue sample including a cell are contacted with capture probes attached to a substrate (e.g., a surface of a substrate), and the cell or tissue sample is permeabilized to allow analytes to be released from the cell and bind to the capture probes attached to the substrate. In some examples, analytes released from a cell can be actively directed to the capture probes attached to a substrate using a variety of methods, e.g., electrophoresis, chemical gradient, pressure gradient, fluid flow, or magnetic field.

In other examples, a capture probe can be directed to interact with a cell or a tissue sample using a variety of methods, e.g., inclusion of a lipid anchoring agent in the capture probe, inclusion of an agent that binds specifically to, or forms a covalent bond with a membrane protein in the capture probe, fluid flow, pressure gradient, chemical gradient, or magnetic field.

Non-limiting aspects of spatial analysis methodologies are described in WO 2011/127099, WO 2014/210233, WO 2014/210225, WO 2016/162309, WO 2018/091676, WO 2012/140224, WO 2014/060483, U.S. Pat. Nos. 10,002,316, 9,727,810, U.S. Patent Application Publication No. 2017/0016053, Rodrigues et al., *Science* 363(6434):1463-1467, 2019; WO 2018/045186, Lee et al., *Nat. Protoc.* 10(3):442-458, 2015; WO 2016/007839, WO 2018/045181, WO 2014/163886, Trejo et al., *PLoS ONE* 14(2):e0212031, 2019, U.S. Patent Application Publication No. 2018/0245142, Chen et al., *Science* 348(6233):aaa6090, 2015, Gao et al., *BMC Biol.* 15:50, 2017, WO 2017/144338, WO 2018/107054, WO 2017/222453, WO 2019/068880, WO 2011/094669, U.S. Pat. Nos. 7,709,198, 8,604,182, 8,951,726, 9,783,841, 10,041,949, WO 2016/057552, WO 2017/147483, WO 2018/022809, WO 2016/166128, WO 2017/027367, WO 2017/027368, WO 2018/136856, WO 2019/075091, U.S. Pat. No. 10,059,990, WO 2018/057999, WO 2015/161173, and Gupta et al., *Nature Biotechnol.* 36:1197-1202, 2018, the entire contents of which are incorporated herein by reference and can be used herein in any combination. Further non-limiting aspects of spatial analysis methodologies are described herein.

Some general terminologies that may be used in this disclosure can be found in Section (I)(b) of WO 2020/176788 and/or U.S. Patent Application Publication No. 2020/0277663. Typically, a "barcode" is a label, or identifier, that conveys or is capable of conveying information (e.g., information about an analyte in a sample, a bead, and/or a capture probe). A barcode can be part of an analyte, or independent of an analyte. A barcode can be attached to an analyte. A particular barcode can be unique relative to other barcodes. For the purpose of this disclosure, an "analyte" can include any biological substance, structure, moiety, or component to be analyzed. The term "target" can similarly refer to an analyte of interest.

Analytes can be broadly classified into one of two groups: nucleic acid analytes, and non-nucleic acid analytes. Examples of non-nucleic acid analytes include, but are not limited to, lipids, carbohydrates, peptides, proteins, glycoproteins (N-linked or O-linked), lipoproteins, phosphoproteins, specific phosphorylated or acetylated variants of proteins, amidation variants of proteins, hydroxylation variants of proteins, methylation variants of proteins, ubiquitylation variants of proteins, sulfation variants of proteins, viral proteins (e.g., viral capsid, viral envelope, viral coat, viral accessory, viral glycoproteins, viral spike, etc.), extracellular and intracellular proteins, antibodies, and antigen binding fragments. In some embodiments, analyte(s) can be peptides or proteins, including without limitation antibodies and enzymes. Additional examples of analytes can be found in Section (I)(c) of WO 2020/176788 and/or U.S. Patent Application Publication No. 2020/0277663. In some embodiments, an analyte can be detected indirectly, such as through detection of an intermediate agent, for example, a connected probe (e.g., a ligation product) or an analyte capture agent (e.g., an oligonucleotide-conjugated antibody), such as those described herein.

A "biological sample" is typically obtained from the subject for analysis using any of a variety of techniques including, but not limited to, biopsy, surgery, and laser capture microscopy (LCM), and generally includes cells and/or other biological material from the subject. In some embodiments, a biological sample can be a tissue section. In some embodiments, a biological sample can be a fixed and/or stained biological sample (e.g., a fixed and/or stained tissue section). Non-limiting examples of stains include histological stains (e.g., hematoxylin and/or eosin) and immunological stains (e.g., fluorescent stains). In some embodiments, a biological sample (e.g., a fixed and/or stained biological sample) can be imaged. Biological samples are also described in Section (I)(d) of WO 2020/176788 and/or U.S. Patent Application Publication No. 2020/0277663.

In some embodiments, a biological sample is permeabilized with one or more permeabilization reagents. For example, permeabilization of a biological sample can facilitate analyte capture. Exemplary permeabilization agents and conditions are described in Section (I)(d)(ii)(13) or the Exemplary Embodiments Section of WO 2020/176788 and/or U.S. Patent Application Publication No. 2020/0277663.

Array-based spatial analysis methods involve the transfer of one or more analytes from a biological sample to an array of features on a substrate, where each feature is associated with a unique spatial location on the array. Subsequent analysis of the transferred analytes includes determining the identity of the analytes and the spatial location of the analytes within the biological sample. The spatial location of an analyte within the biological sample is determined based on the feature to which the analyte is bound (e.g., directly or indirectly) on the array, and the feature's relative spatial location within the array.

A "capture probe" refers to any molecule capable of capturing (directly or indirectly) and/or labelling an analyte (e.g., an analyte of interest) in a biological sample. In some embodiments, the capture probe is a nucleic acid or a polypeptide. In some embodiments, the capture probe includes a barcode (e.g., a spatial barcode and/or a unique molecular identifier (UMI)) and a capture domain. In some embodiments, a capture probe can include a cleavage domain and/or a functional domain (e.g., a primer-binding site, such as for next-generation sequencing (NGS)).

FIG. 1 is a schematic diagram showing an exemplary capture probe, as described herein. As shown, the capture probe 102 is optionally coupled to a feature 101 by a cleavage domain 103, such as a disulfide linker. The capture probe can include a functional sequence 104 that is useful for subsequent processing. The functional sequence 104 can include all or a part of sequencer specific flow cell attachment sequence (e.g., a P5 or P7 sequence), all or a part of a sequencing primer sequence, (e.g., a R1 primer binding site, a R2 primer binding site), or combinations thereof. The capture probe can also include a spatial barcode 105. The capture probe can also include a unique molecular identifier (UMI) sequence 106. While FIG. 1 shows the spatial barcode 105 as being located upstream (5') of UMI sequence 106, it is to be understood that capture probes wherein UMI sequence 106 is located upstream (5') of the spatial barcode 105 is also suitable for use in any of the methods described herein. The capture probe can also include a capture domain 107 to facilitate capture of a target analyte. The capture domain can have a sequence complementary to a sequence of a nucleic acid analyte. The capture domain can have a sequence complementary to a connected probe described herein. The capture domain can have a sequence complementary to a capture handle sequence present in an analyte capture agent. The capture domain can have a sequence complementary to a splint oligonucleotide. Such splint oligonucleotide, in addition to having a sequence complementary to a capture domain of a capture probe, can have a sequence of a nucleic acid analyte, a sequence complementary to a portion of a connected probe described herein, and/or a capture handle sequence described herein.

The functional sequences can generally be selected for compatibility with any of a variety of different sequencing systems, e.g., Ion Torrent Proton or PGM, Illumina sequencing instruments, PacBio, Oxford Nanopore, etc., and the requirements thereof. In some embodiments, functional sequences can be selected for compatibility with non-commercialized sequencing systems. Examples of such sequencing systems and techniques, for which suitable functional sequences can be used, include (but are not limited to) Ion Torrent Proton or PGM sequencing, Illumina sequencing, PacBio SMRT sequencing, and Oxford Nanopore sequencing. Further, in some embodiments, functional sequences can be selected for compatibility with other sequencing systems, including non-commercialized sequencing systems.

In some embodiments, the spatial barcode 105 and functional sequences 104 are common to all of the probes attached to a given feature. In some embodiments, the UMI sequence 106 of a capture probe attached to a given feature is different from the UMI sequence of a different capture probe attached to the given feature.

Figure 2:
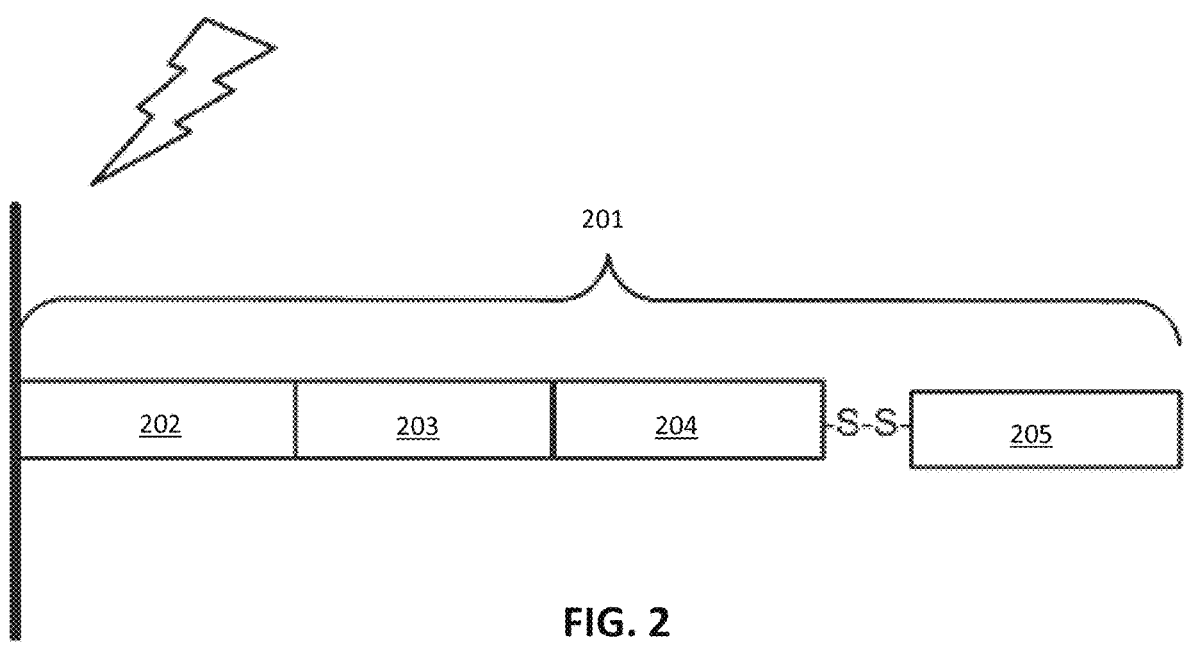
FIG. 2 is a schematic illustrating a cleavable capture probe, wherein the cleaved capture probe can enter into a non-permeabilized cell and bind to target analytes within the sample.

FIG. 2 is a schematic illustrating a cleavable capture probe, wherein the cleaved capture probe can enter into a non-permeabilized cell and bind to analytes within the sample. The capture probe 201 contains a cleavage domain 202, a cell penetrating peptide 203, a reporter molecule 204, and a disulfide bond (—S—S—). 205 represents all other parts of a capture probe, for example a spatial barcode and a capture domain.

Figure 3:
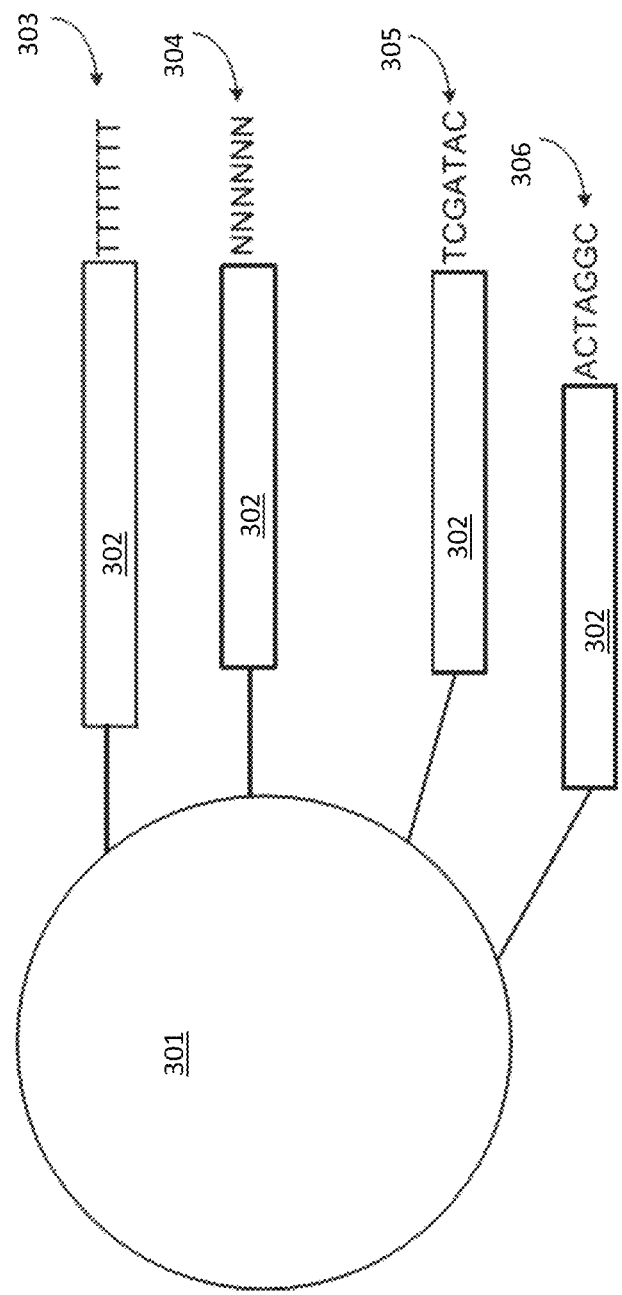
FIG. 3 is a schematic diagram of an exemplary multiplexed spatially-barcoded feature.

FIG. 3 is a schematic diagram of an exemplary multiplexed spatially-barcoded feature. In FIG. 3, the feature 301 can be coupled to spatially-barcoded capture probes, wherein the spatially-barcoded probes of a particular feature can possess the same spatial barcode, but have different capture domains designed to associate the spatial barcode of the feature with more than one target analyte. For example, a feature may be coupled to four different types of spatially-barcoded capture probes, each type of spatially-barcoded capture probe possessing the spatial barcode 302. One type of capture probe associated with the feature includes the spatial barcode 302 in combination with a poly(T) capture domain 303, designed to capture mRNA target analytes. A second type of capture probe associated with the feature includes the spatial barcode 302 in combination with a random N-mer capture domain 304 for gDNA analysis. A third type of capture probe associated with the feature includes the spatial barcode 302 in combination with a capture domain complementary to a capture handle sequence of an analyte capture agent of interest 305. A fourth type of capture probe associated with the feature includes the spatial barcode 302 in combination with a capture domain that can specifically bind a nucleic acid molecule 306 that can function in a CRISPR assay (e.g., CRISPR/Cas9). While only four different capture probe-barcoded constructs are shown in FIG. 3, capture-probe barcoded constructs can be tailored for analyses of any given analyte associated with a nucleic acid and capable of binding with such a construct. For example, the schemes shown in FIG. 3 can also be used for concurrent analysis of other analytes disclosed herein, including, but not limited to: (a) mRNA, a lineage tracing construct, cell surface or intracellular proteins and metabolites, and gDNA; (b) mRNA, accessible chromatin (e.g., ATAC-seq, DNase-seq, and/or MNase-seq) cell surface or intracellular proteins and metabolites, and a perturbation agent (e.g., a CRISPR crRNA/sgRNA, TALEN, zinc finger nuclease, and/or antisense oligonucleotide as described herein); (c) mRNA, cell surface or intracellular proteins and/or metabolites, a barcoded labelling agent (e.g., the MEW multimers described herein), and a V(D)J sequence of an immune cell receptor (e.g., T-cell receptor). In some embodiments, a perturbation agent can be a small molecule, an antibody, a drug, an aptamer, a miRNA, a physical environmental (e.g., temperature change), or any other known perturbation agents. See, e.g., Section (II)(b) (e.g., subsections (i)-(vi)) of WO 2020/176788 and/or U.S. Patent Application Publication No. 2020/0277663. Generation of capture probes can be achieved by any appropriate method, including those described in Section (II)(d)(ii) of WO 2020/176788 and/or U.S. Patent Application Publication No. 2020/0277663.

In some embodiments, more than one analyte type (e.g., nucleic acids and proteins) from a biological sample can be detected (e.g., simultaneously or sequentially) using any appropriate multiplexing technique, such as those described in Section (IV) of WO 2020/176788 and/or U.S. Patent Application Publication No. 2020/0277663.

In some embodiments, detection of one or more analytes (e.g., protein analytes) can be performed using one or more analyte capture agents. As used herein, an "analyte capture agent" refers to an agent that interacts with an analyte (e.g., an analyte in a biological sample) and with a capture probe (e.g., a capture probe attached to a substrate or a feature) to identify the analyte. In some embodiments, the analyte capture agent includes: (i) an analyte binding moiety (e.g., that binds to an analyte), for example, an antibody or antigen-binding fragment thereof; (ii) analyte binding moiety barcode; and (iii) a capture handle sequence. As used herein, the term "analyte binding moiety barcode" refers to a barcode that is associated with or otherwise identifies the analyte binding moiety. As used herein, the term "analyte capture sequence" or "capture handle sequence" refers to a region or moiety configured to hybridize to, bind to, couple to, or otherwise interact with a capture domain of a capture probe. In some embodiments, a capture handle sequence is complementary to a capture domain of a capture probe. In some cases, an analyte binding moiety barcode (or portion thereof) may be able to be removed (e.g., cleaved) from the analyte capture agent.

Figure 4:
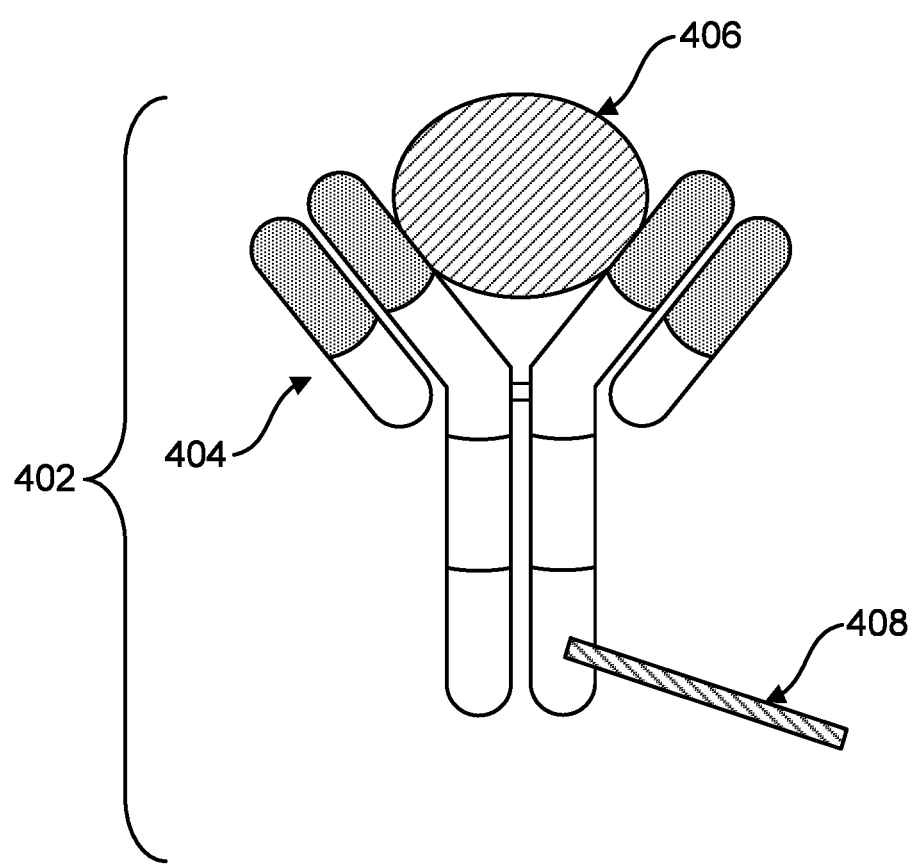
FIG. 4 is a schematic diagram of an exemplary analyte capture agent.

FIG. 4 is a schematic diagram of an exemplary analyte capture agent 402 comprised of an analyte-binding moiety 404 and an analyte-binding moiety barcode domain 408. The exemplary analyte-binding moiety 404 is a molecule capable of binding to an analyte 406 and the analyte capture agent is capable of interacting with a spatially-barcoded capture probe. The analyte-binding moiety can bind to the analyte 406 with high affinity and/or with high specificity. The analyte capture agent can include an analyte-binding moiety barcode domain 408, a nucleotide sequence (e.g., an oligonucleotide), which can hybridize to at least a portion or an entirety of a capture domain of a capture probe. The analyte-binding moiety barcode domain 408 can comprise an analyte binding moiety barcode and a capture handle sequence described herein. The analyte-binding moiety 404 can include a polypeptide and/or an aptamer. The analyte-binding moiety 404 can include an antibody or antibody fragment (e.g., an antigen-binding fragment).

Figure 5:
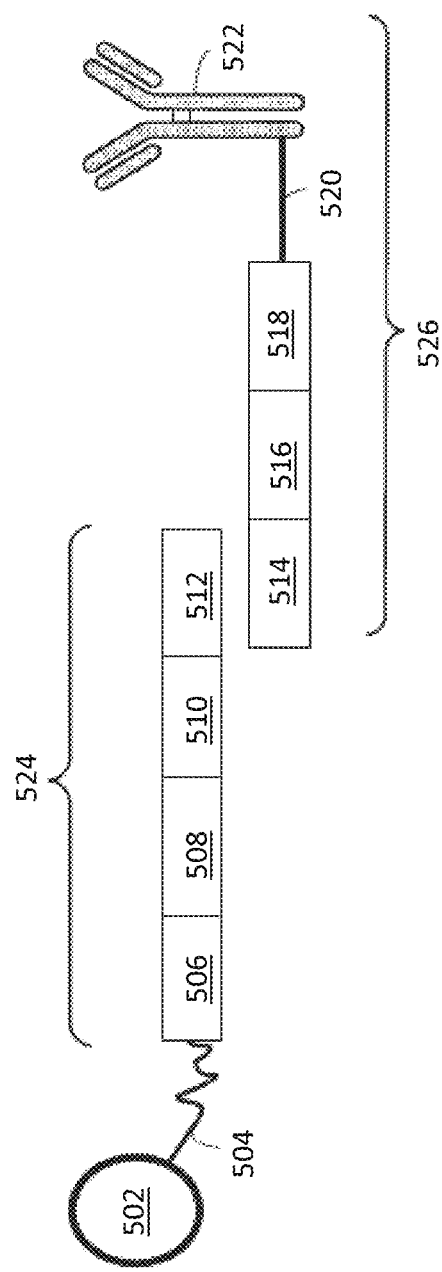
FIG. 5 is a schematic diagram depicting an exemplary interaction between a feature-immobilized capture probe and an analyte capture agent.

FIG. 5 is a schematic diagram depicting an exemplary interaction between a feature-immobilized capture probe 524 and an analyte capture agent 526. The feature-immobilized capture probe 524 can include a spatial barcode 508 as well as functional sequences 506 and UMI 510, as described elsewhere herein. The capture probe can also include a capture domain 512 that is capable of binding to an analyte capture agent 526. The analyte capture agent 526 can include a functional sequence 518, analyte binding moiety barcode 516, and a capture handle sequence 514 that is capable of binding to the capture domain 512 of the capture probe 524. The analyte capture agent can also include a linker 520 that allows the capture agent barcode domain 516 to couple to the analyte binding moiety 522.

Figure 6A:
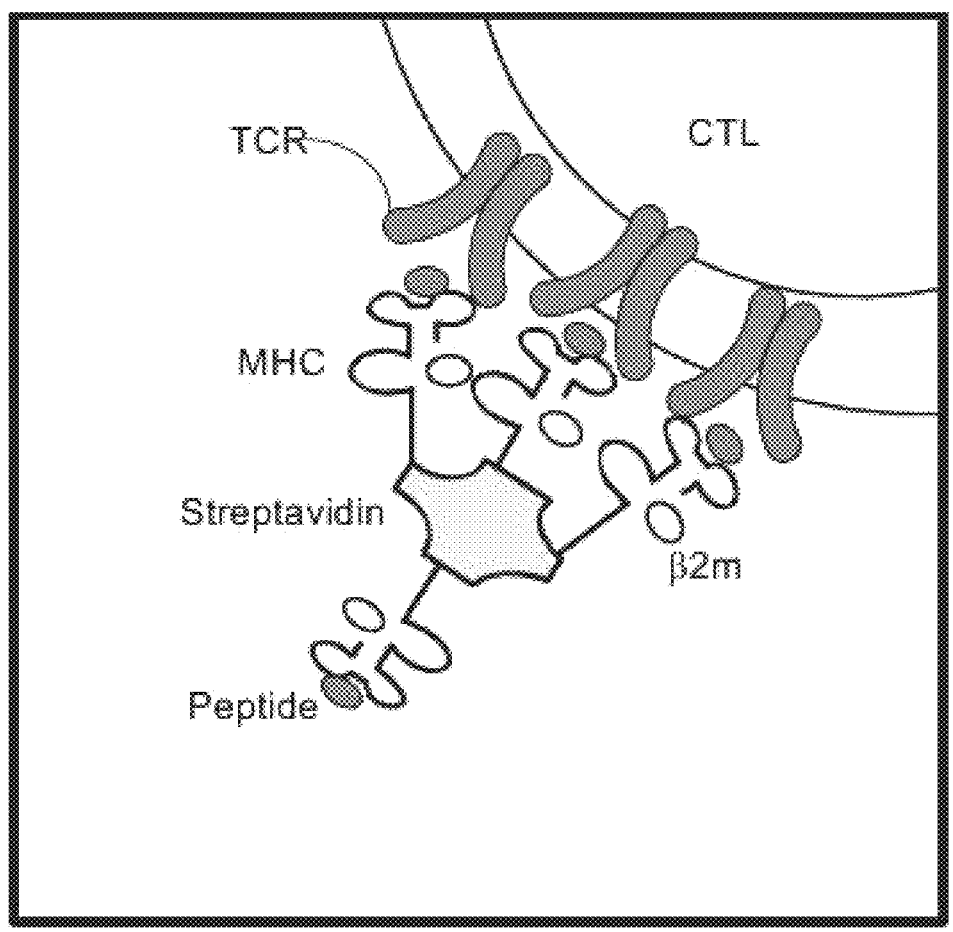
FIGS. 6A, 6B, and 6C are schematics illustrating how streptavidin cell tags can be utilized in an array-based system to produce spatially-barcoded cells or cellular contents.
Figure 6B:
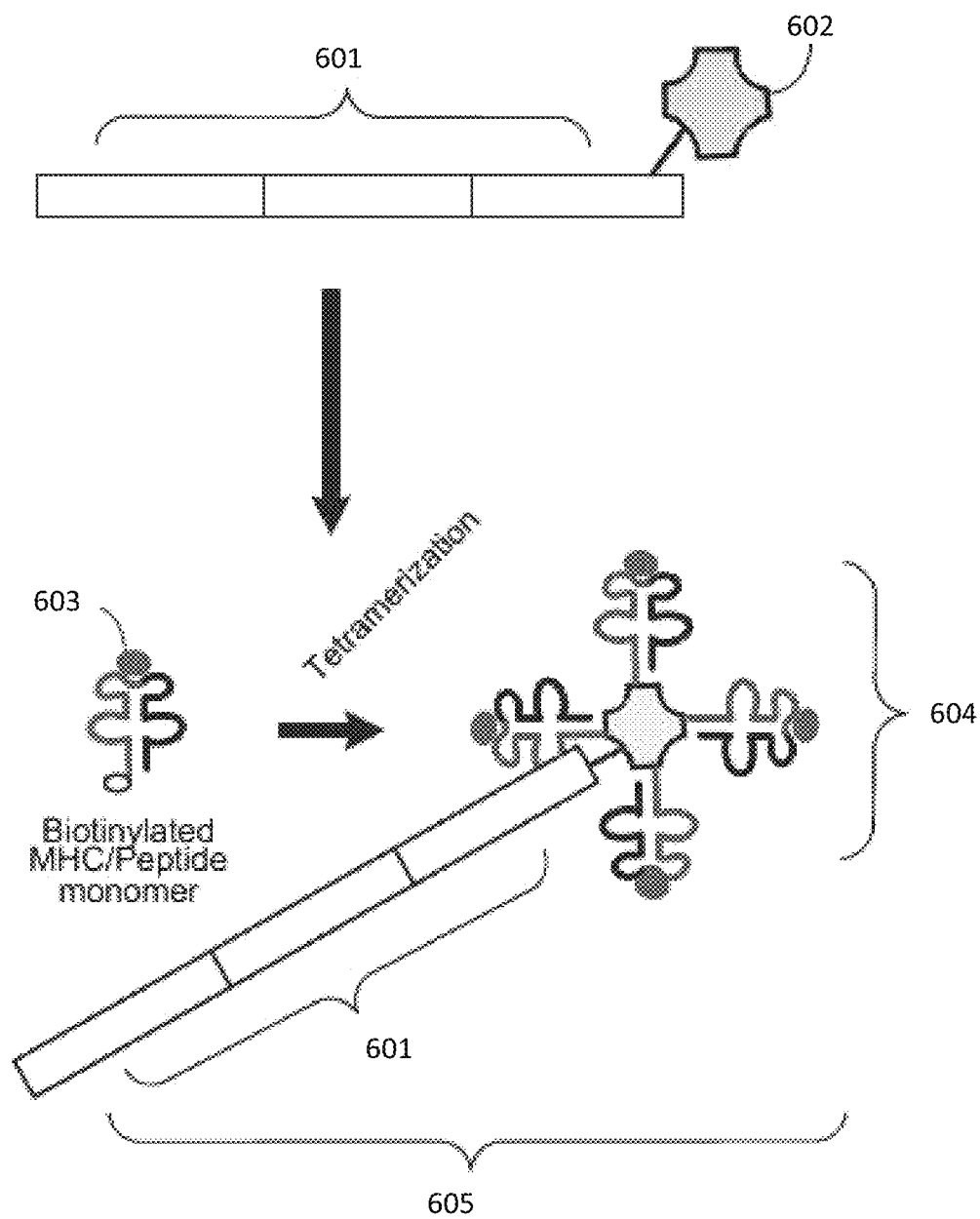
Figure 6C:
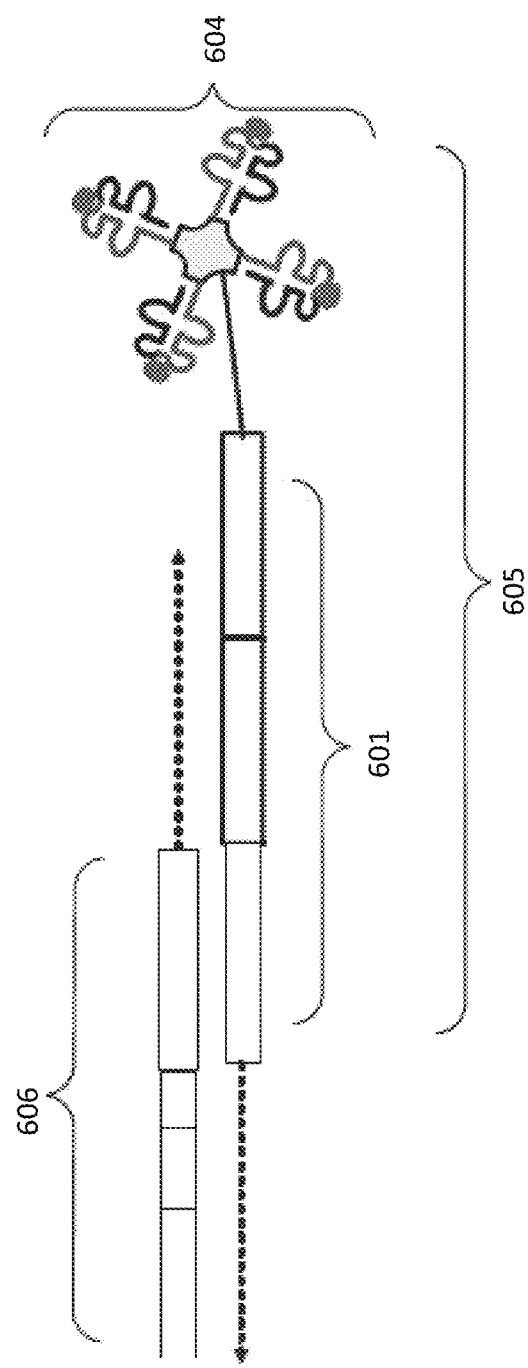

FIGS. 6A, 6B, and 6C are schematics illustrating how streptavidin cell tags can be utilized in an array-based system to produce a spatially-barcoded cell or cellular contents. For example, as shown in FIG. 6A, peptide-bound major histocompatibility complex (MHC) can be individually associated with biotin (β2m) and bound to a streptavidin moiety such that the streptavidin moiety comprises multiple pMHC moieties. Each of these moieties can bind to a TCR such that the streptavidin binds to a target T-cell via multiple MHC/TCR binding interactions. Multiple interactions synergize and can substantially improve binding affinity. Such improved affinity can improve labelling of T-cells and also reduce the likelihood that labels will dissociate from T-cell surfaces. As shown in FIG. 6B, a capture agent barcode domain 601 can be modified with streptavidin 602 and contacted with multiple molecules of biotinylated MHC 603 such that the biotinylated MHC 603 molecules are coupled with the streptavidin conjugated capture agent barcode domain 601. The result is a barcoded MHC multimer complex 605. As shown in FIG. 6B, the capture agent barcode domain sequence 601 can identify the MHC as its associated label and also includes optional functional sequences such as sequences for hybridization with other oligonucleotides. As shown in FIG. 6C, one example oligonucleotide is capture probe 606 that comprises a complementary sequence (e.g., rGrGrG corresponding to C C C), a barcode sequence and other functional sequences, such as, for example, a UMI, an adapter sequence (e.g., comprising a sequencing primer sequence (e.g., R1 or a partial R1 ("pR1"), R2), a flow cell attachment sequence (e.g., P5 or P7 or partial sequences thereof)), etc. In some cases, capture probe 606 may at first be associated with a feature (e.g., a gel bead) and released from the feature. In other embodiments, capture probe 606 can hybridize with a capture agent barcode domain 601 of the MHC-oligonucleotide complex 605. The hybridized oligonucleotides (Spacer C C C and Spacer rGrGrG) can then be extended in primer extension reactions such that constructs comprising sequences that correspond to each of the two spatial barcode sequences (the spatial barcode associated with the capture probe, and the barcode associated with the MHC-oligonucleotide complex) are generated. In some cases, one or both of the corresponding sequences may be a complement of the original sequence in capture probe 606 or capture agent barcode domain 601. In other embodiments, the capture probe and the capture agent barcode domain are ligated together. The resulting constructs can be optionally further processed (e.g., to add any additional sequences and/or for clean-up) and subjected to sequencing. As described elsewhere herein, a sequence derived from the capture probe 606 spatial barcode sequence may be used to identify a feature and the sequence derived from spatial barcode sequence on the capture agent barcode domain 601 may be used to identify the particular peptide WIC complex 604 bound on the surface of the cell (e.g., when using WIC-peptide libraries for screening immune cells or immune cell populations).

Additional description of analyte capture agents can be found in Section (II)(b)(ix) of WO 2020/176788 and/or Section (II)(b)(viii) U.S. Patent Application Publication No. 2020/0277663.

There are at least two methods to associate a spatial barcode with one or more neighboring cells, such that the spatial barcode identifies the one or more cells, and/or contents of the one or more cells, as associated with a particular spatial location. One method is to promote analytes or analyte proxies (e.g., intermediate agents) out of a cell and towards a spatially-barcoded array (e.g., including spatially-barcoded capture probes). Another method is to cleave spatially-barcoded capture probes from an array and promote the spatially-barcoded capture probes towards and/ or into or onto the biological sample.

In some cases, capture probes may be configured to prime, replicate, and consequently yield optionally barcoded extension products from a template (e.g., a DNA or RNA template, such as an analyte or an intermediate agent (e.g., a connected probe (e.g., a ligation product) or an analyte capture agent), or a portion thereof), or derivatives thereof (see, e.g., Section (II)(b)(vii) of WO 2020/176788 and/or U.S. Patent Application Publication No. 2020/0277663 regarding extended capture probes). In some cases, capture probes may be configured to form a connected probe (e.g., a ligation product) with a template (e.g., a DNA or RNA template, such as an analyte or an intermediate agent, or portion thereof), thereby creating ligations products that serve as proxies for a template.

As used herein, an "extended capture probe" refers to a capture probe having additional nucleotides added to the terminus (e.g., 3' or 5' end) of the capture probe thereby extending the overall length of the capture probe. For example, an "extended 3' end" indicates additional nucleotides were added to the most 3' nucleotide of the capture probe to extend the length of the capture probe, for example, by polymerization reactions used to extend nucleic acid molecules including templated polymerization catalyzed by a polymerase (e.g., a DNA polymerase or a reverse transcriptase). In some embodiments, extending the capture probe includes adding to a 3' end of a capture probe a nucleic acid sequence that is complementary to a nucleic acid sequence of an analyte or intermediate agent specifically bound to the capture domain of the capture probe. In some embodiments, the capture probe is extended using reverse transcription. In some embodiments, the capture probe is extended using one or more DNA polymerases. The extended capture probes include the sequence of the capture probe and the sequence of the spatial barcode of the capture probe.

In some embodiments, extended capture probes are amplified (e.g., in bulk solution or on the array) to yield quantities that are sufficient for downstream analysis, e.g., via DNA sequencing. In some embodiments, extended capture probes (e.g., DNA molecules) act as templates for an amplification reaction (e.g., a polymerase chain reaction).

Additional variants of spatial analysis methods, including in some embodiments, an imaging step, are described in Section (II)(a) of WO 2020/176788 and/or U.S. Patent Application Publication No. 2020/0277663. Analysis of captured analytes (and/or intermediate agents or portions thereof), for example, including sample removal, extension of capture probes, sequencing (e.g., of a cleaved extended capture probe and/or a cDNA molecule complementary to an extended capture probe), sequencing on the array (e.g., using, for example, in situ hybridization or in situ ligation approaches), temporal analysis, and/or proximity capture, is described in Section (II)(g) of WO 2020/176788 and/or U.S. Patent Application Publication No. 2020/0277663. Some quality control measures are described in Section (II)(h) of WO 2020/176788 and/or U.S. Patent Application Publication No. 2020/0277663.

Spatial information can provide information of biological importance. For example, the methods and compositions described herein can allow for: identification of transcriptome and/or proteome expression profiles (e.g., in healthy and/or diseased tissue); identification of multiple analyte types in close proximity (e.g., nearest neighbor analysis); determination of up- and/or down-regulated genes and/or proteins in diseased tissue; characterization of tumor microenvironments; characterization of tumor immune responses; characterization of cells types and their co-localization in tissue; and identification of genetic variants within tissues (e.g., based on gene and/or protein expression profiles associated with specific disease or disorder biomarkers).

Typically, for spatial array-based methods, a substrate functions as a support for direct or indirect attachment of capture probes to features of the array. A "feature" is an entity that acts as a support or repository for various molecular entities used in spatial analysis. In some embodiments, some or all of the features in an array are functionalized for analyte capture. Exemplary substrates are described in Section (II)(c) of WO 2020/176788 and/or U.S. Patent Application Publication No. 2020/0277663. Exemplary features and geometric attributes of an array can be found in Sections (II)(d)(i), (II)(d)(iii), and (II)(d)(iv) of WO 2020/176788 and/or U.S. Patent Application Publication No. 2020/0277663.

Generally, analytes and/or intermediate agents (or portions thereof) can be captured when contacting a biological sample with a substrate including capture probes (e.g., a substrate with capture probes embedded, spotted, printed, fabricated on the substrate, or a substrate with features (e.g., beads, wells) comprising capture probes). As used herein, "contact," "contacted," and/or "contacting," a biological sample with a substrate refers to any contact (e.g., direct or indirect) such that capture probes can interact (e.g., bind covalently or non-covalently (e.g., hybridize)) with analytes from the biological sample. Capture can be achieved actively (e.g., using electrophoresis) or passively (e.g., using diffusion). Analyte capture is further described in Section (II)(e) of WO 2020/176788 and/or U.S. Patent Application Publication No. 2020/0277663.

In some cases, spatial analysis can be performed by attaching and/or introducing a molecule (e.g., a peptide, a lipid, or a nucleic acid molecule) having a barcode (e.g., a spatial barcode) to a biological sample (e.g., to a cell in a biological sample). In some embodiments, a plurality of molecules (e.g., a plurality of nucleic acid molecules) having a plurality of barcodes (e.g., a plurality of spatial barcodes) are introduced to a biological sample (e.g., to a plurality of cells in a biological sample) for use in spatial analysis. In some embodiments, after attaching and/or introducing a molecule having a barcode to a biological sample, the biological sample can be physically separated (e.g., dissociated) into single cells or cell groups for analysis. Some such methods of spatial analysis are described in Section (III) of WO 2020/176788 and/or U.S. Patent Application Publication No. 2020/0277663.

In some cases, spatial analysis can be performed by detecting multiple oligonucleotides that hybridize to an analyte. In some instances, for example, spatial analysis can be performed using RNA-templated ligation (RTL). Methods of RTL have been described previously. See, e.g., Credle et al., *Nucleic Acids Res.* 2017 Aug. 21; 45(14):e128. Typically, RTL includes hybridization of two oligonucleotides to adjacent or proximal sequences on an analyte (e.g., an RNA molecule, such as an mRNA molecule). After hybridization to the analyte, a ligase (e.g., SplintR ligase) ligates the two oligonucleotides together, creating a connected probe (e.g., a ligation product). After ligation, the connected probe (e.g., a ligation product) is released from the analyte. The released connected probe (e.g., a ligation product) can then be captured by capture probes (e.g., instead of direct capture of an analyte) on an array, optionally amplified, and sequenced, thus determining the location and optionally the abundance of the analyte in the biological sample.

During analysis of spatial information, sequence information for a spatial barcode associated with an analyte is obtained, and the sequence information can be used to provide information about the spatial distribution of the analyte in the biological sample. Various methods can be used to obtain the spatial information. In some embodiments, specific capture probes and the analytes they capture are associated with specific locations in an array of features on a substrate.

When sequence information is obtained for capture probes and/or analytes during analysis of spatial information, the locations of the capture probes and/or analytes can be determined by referring to the stored information that uniquely associates each spatial barcode with an array feature location. In this manner, specific capture probes and captured analytes are associated with specific locations in the array of features. Each array feature location represents a position relative to a coordinate reference point (e.g., an array location, a fiducial marker) for the array. Accordingly, each feature location has an "address" or location in the coordinate space of the array.

Some exemplary spatial analysis workflows are described in the Exemplary Embodiments section of WO 2020/176788 and/or U.S. Patent Application Publication No. 2020/0277663. See, for example, the Exemplary embodiment starting with "In some non-limiting examples of the workflows described herein, the sample can be immersed . . . " of WO 2020/176788 and/or U.S. Patent Application Publication No. 2020/0277663. See also, e.g., the Visium Spatial Gene Expression Reagent Kits User Guide (e.g., Rev D, dated October 2020), and/or the Visium Spatial Tissue Optimization Reagent Kits User Guide (e.g., Rev D, dated October 2020). In some embodiments, spatial analysis can be performed using dedicated hardware and/or software, such as any of the systems described in Sections (II)(e)(ii) and/or (V) of WO 2020/176788 and/or U.S. Patent Application Publication No. 2020/0277663, or any of one or more of the devices or methods described in Sections Control Slide for Imaging, Methods of Using Control Slides and Substrates for, Systems of Using Control Slides and Substrates for Imaging, and/or Sample and Array Alignment Devices and Methods, Informational labels of WO 2020/123320.

Suitable systems for performing spatial analysis can include components such as a chamber (e.g., a flow cell or sealable, fluid-tight chamber) for containing a biological sample. The biological sample can be mounted for example, in a biological sample holder. One or more fluid chambers can be connected to the chamber and/or the sample holder via fluid conduits, and fluids can be delivered into the chamber and/or sample holder via fluidic pumps, vacuum sources, or other devices coupled to the fluid conduits that create a pressure gradient to drive fluid flow. One or more valves can also be connected to fluid conduits to regulate the flow of reagents from reservoirs to the chamber and/or sample holder.

The systems can optionally include a control unit that includes one or more electronic processors, an input interface, an output interface (such as a display), and a storage unit (e.g., a solid state storage medium such as, but not limited to, a magnetic, optical, or other solid state, persistent, writeable and/or re-writeable storage medium). The control unit can optionally be connected to one or more remote devices via a network. The control unit (and components thereof) can generally perform any of the steps and functions described herein. Where the system is connected to a remote device, the remote device (or devices) can perform any of the steps or features described herein. The systems can optionally include one or more detectors (e.g., CCD, CMOS) used to capture images. The systems can also optionally include one or more light sources (e.g., LED-based, diode-based, lasers) for illuminating a sample, a substrate with features, analytes from a biological sample captured on a substrate, and various control and calibration media.

The systems can optionally include software instructions encoded and/or implemented in one or more of tangible storage media and hardware components such as application specific integrated circuits. The software instructions, when executed by a control unit (and in particular, an electronic processor) or an integrated circuit, can cause the control unit, integrated circuit, or other component executing the software instructions to perform any of the method steps or functions described herein.

In some cases, the systems described herein can detect (e.g., register an image) the biological sample on the array. Exemplary methods to detect the biological sample on an array are described in PCT Application No. 2020/061064 and/or U.S. patent application Ser. No. 16/951,854.

Prior to transferring analytes from the biological sample to the array of features on the substrate, the biological sample can be aligned with the array. Alignment of a biological sample and an array of features including capture probes can facilitate spatial analysis, which can be used to detect differences in analyte presence and/or level within different positions in the biological sample, for example, to generate a three-dimensional map of the analyte presence and/or level. Exemplary methods to generate a two- and/or three-dimensional map of the analyte presence and/or level are described in PCT Application No. 2020/053655 and spatial analysis methods are generally described in WO 2020/061108 and/or U.S. patent application Ser. No. 16/951,864.

In some cases, a map of analyte presence and/or level can be aligned to an image of a biological sample using one or more fiducial markers, e.g., objects placed in the field of view of an imaging system which appear in the image produced, as described in the Substrate Attributes Section, Control Slide for Imaging Section of WO 2020/123320, PCT Application No. 2020/061066, and/or U.S. patent application Ser. No. 16/951,843. Fiducial markers can be used as a point of reference or measurement scale for alignment (e.g., to align a sample and an array, to align two substrates, to determine a location of a sample or array on a substrate relative to a fiducial marker) and/or for quantitative measurements of sizes and/or distances.

Embodiments described herein may map the spatial gene expression of complex tissue samples (e.g., on tissue slides) with slides (e.g., array slides) that utilize analyte and/or mRNA transcript capture and spatial barcoding technology for library preparation. A tissue (e.g., fresh-frozen, formalin-fixed paraffin-embedded (FFPE), or the like) may be sectioned and placed in proximity to a slide with thousands of barcoded spots, each containing millions of capture oligonucleotides with spatial barcodes unique to that spot. Once tissue sections are fixed, stained, and permeabilized, they release mRNA which binds to capture oligos from a proximal location on the tissue. A reverse transcription reaction may occur while the tissue is still in place, generating a cDNA library that incorporates the spatial barcodes and preserves spatial information. Barcoded cDNA libraries are mapped back to a specific spot on a capture area of the barcoded spots. This gene expression data may be subsequently layered over a high-resolution microscope image of the tissue section, making it possible to visualize the expression of any mRNA, or combination of mRNAs, within the morphology of the tissue in a spatially-resolved manner.

I. Sample and Array Alignment Devices and Methods

Spatial analysis workflows described herein generally involve contacting a sample with an array of features. With such workflows, aligning the sample with the array may be important in performing spatial (e.g., spatial transcriptomic) assays. The ability to efficiently generate robust experimental data for a given sample can depend greatly on the alignment of the sample and the array. Traditional techniques require samples to be placed directly onto the array. This approach can require skilled personnel and additional experimental time to prepare a section of the sample and to mount the section of the sample directly on the array. Misalignment of the sample and the array can result in wasted resources, extended sample preparation time, and inefficient use of samples, which may be limited in quantity.

The systems, methods, and computer readable mediums described herein can enable efficient and precise alignment of samples and arrays, thus facilitating the spatial omic (e.g., spatial transcriptomic) imaging and analysis workflows or assays described herein. Samples, such as portions of tissue, can be placed on a first substrate. The first substrate can include a slide onto which a user can place a sample of the tissue. An array, such as a reagent array, can be included (e.g., formed) on a second substrate. The second substrate can include a slide and the array can be formed on the second substrate. The use of separate substrates for the sample and the array can beneficially allow user to perform the spatial omic (e.g., spatial transcriptomic) assays described herein without requiring the sample to be placed onto an array substrate. The sample holder and methods of use described herein can improve the ease by which users provide samples for spatial omic (e.g., spatial transcriptomic) analysis. For example, the systems and methods described herein alleviate users from possessing advanced sample or tissue sectioning or mounting expertise. Additional benefits of utilizing separate substrates for samples and arrays can include improved sample preparation and sample imaging times, greater ability to perform region of interest (ROI) selection, and more efficient use of samples and array substrates. The systems, methods, and computer readable mediums described herein can further enable users to select the best sections of a sample to commit to sequencing workflows. Some tissue samples or portions of the tissue samples can be damaged during mounting. For examples, the tissue samples or portions of the tissue samples can be folded over on themselves. The systems, methods, and computer readable mediums described herein can further enable users to confirm relevant pathology and/or biology prior to committing to sequencing workflows.

The sample substrate and the array substrate, and thus, the sample and the array, can be aligned using the instrument and processes described herein. The alignment techniques and methods described herein can generate more accurate spatial (e.g., spatial transcriptomic) assay results due to the improved alignment of samples with an array, such as a reagent array.

In some embodiments, a workflow described herein comprises contacting a sample disposed on an area of a first substrate with at least one feature array of a second substrate. In some embodiments, the contacting comprises bringing the two substrates into proximity such that the sample on the first substrate may be aligned with the barcoded array on the second substrate. In some instances, the contacting is achieved by arranging the first substrate and the second substrate in a sandwich assembly. In some embodiments, the workflow comprises a prior step of mounting the sample onto the first substrate.

Alignment of the sample on the first substrate with the array on the second substrate may be achieved manually or automatically (e.g., via a motorized alignment). In some aspects, manual alignment may be done with minimal optical or mechanical assistance and may result in limited precision when aligning a desired region of interest for the sample and the barcoded array. Additionally, adjustments to alignment done manually may be time-consuming due to the relatively small time requirements during the permeabilization step.

Figure 7:
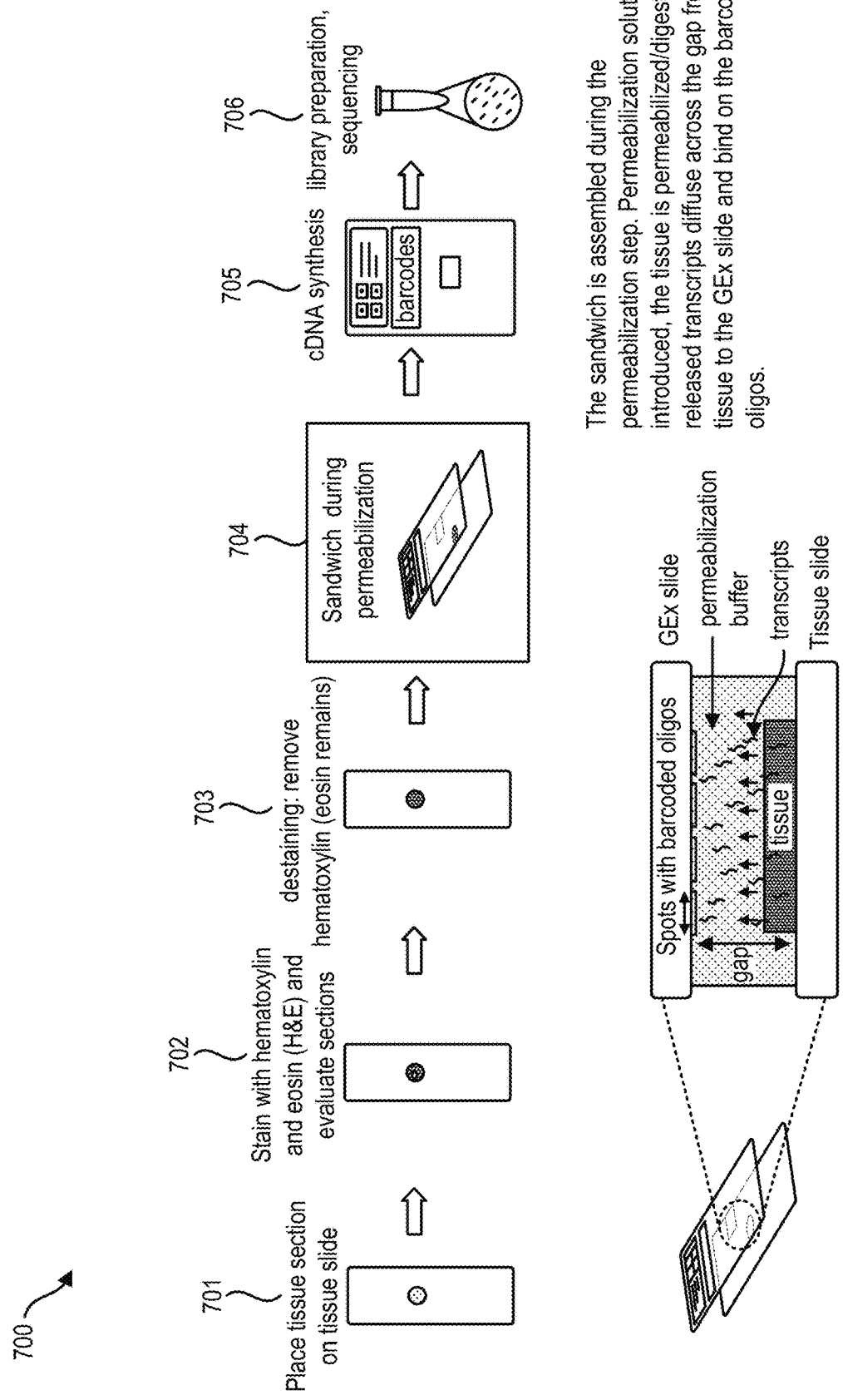
FIG. 7 shows an exemplary spatial analysis workflow in accordance with some example implementations.

FIG. 7 shows an exemplary spatial analysis workflow 700 in accordance with some example implementations. The workflow 700 includes preparing a biological sample on a slide (e.g., a pathology slide) 701, fixing the sample, and/or staining 702 the biological sample for imaging. The stained sample can be then imaged on the slide using brightfield (to image the sample hematoxylin and eosin stain) and/or fluorescence (to image features) modalities. The imaging may include high resolution imaging (e.g., images that can disclose pathological and histological features). Optionally, at 703, the sample can be destained prior to permeabilization. At 704, a permeabilization solution may be applied to biological sample while the pathology slide is aligned in a "sandwich" configuration with a slide comprising a spatially barcoded array (e.g., a GEx slide). The permeabilization solution allows the analyte and/or mRNA transcripts to migrate away from the sample, diffuse across the permeabilization solution, and toward the array. The analyte and/or mRNA transcripts interacts with a capture probe on the spatially-barcoded array on the slide.

At 705, the capture probes can be optionally cleaved from the array, and the captured analytes can be spatially-barcoded by performing a reverse transcriptase first strand cDNA reaction. A first strand cDNA reaction can be optionally performed using template switching oligonucleotides. At 706, the first strand cDNA can be amplified (e.g., using polymerase chain reaction (PCR)), where the forward and reverse primers flank the spatial barcode and analyte regions of interest, generating a library associated with a particular spatial barcode. In some embodiments, the cDNA comprises a sequencing by synthesis (SBS) primer sequence. The library amplicons may be sequenced and analyzed to decode spatial information.

Figure 8:
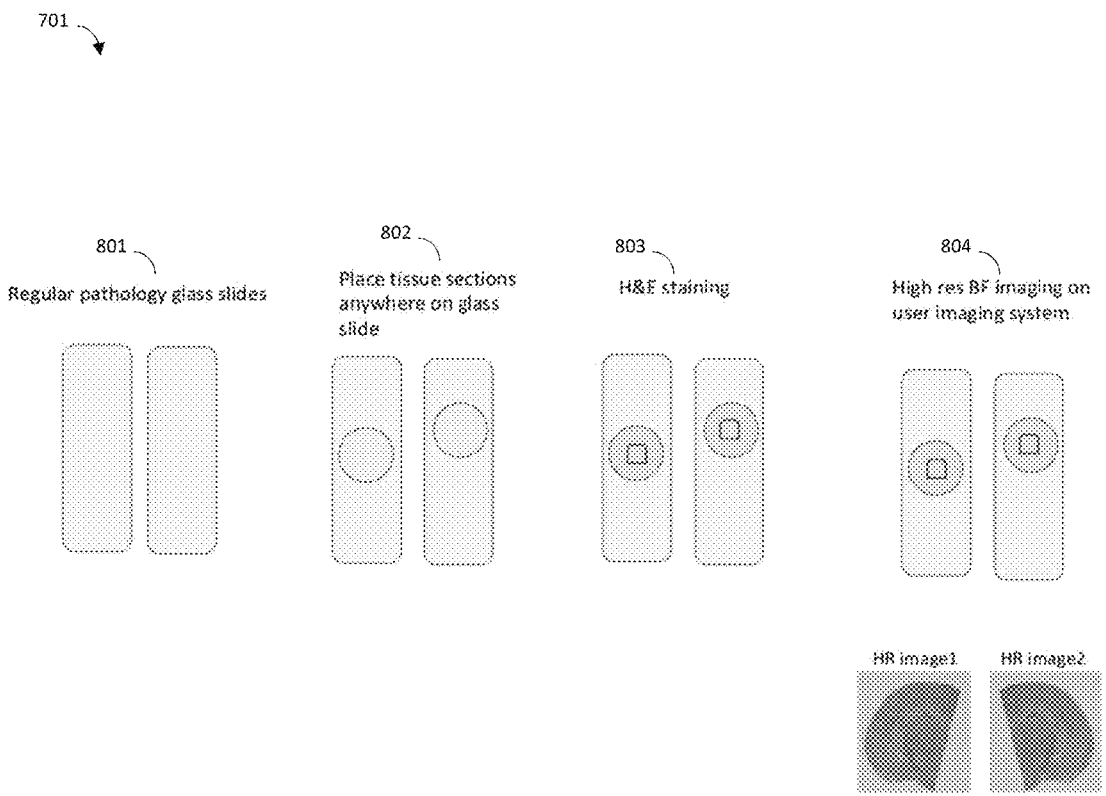
FIG. 8 depicts an example workflow for preparing the biological sample on a slide in accordance with some example implementations.

FIG. 8 depicts the example workflow 701 for preparing the biological sample on the slide (e.g., a pathology slide) in accordance with some example implementations. Preparing the biological sample on the slide may include selecting a pathology glass slide 801. The workflow 701 further includes placing tissue sections on the glass slide 802. Placing tissue sections on the glass slide may include placing the tissue anywhere on the glass slide including placing the tissue on or in relation to a fiducial disposed on the glass slide. The fiducial may include any marking to aid in placement of the tissue on the slide and/or aid in the alignment of the tissue slide relative to the array slide. The workflow 701 further includes staining the tissue with hematoxylin and eosin 803 or another staining agent or method. The workflow 701 further includes imaging the tissue 804 on the slide using brightfield (to image the sample hematoxylin and eosin stain) or another imaging technique. The imaging may include high resolution imaging on a user imaging system. The imaging may allow the user to confirm the relevant pathology and/or identify any target areas for analysis.

Embodiments described herein relating to preparing the biological sample on the slide may beneficially allow a user to confirm pathology or relevant regions on a tissue section, to confirm selection of best or undamaged tissue sections for analysis, to improve array-tissue alignment by allowing placement anywhere on the pathology slide. Further, workflows for preparing the biological sample on the slide may empower user or scientists to choose what to sequence (e.g., what tissue section(s) to sequence).

Figure 9A:
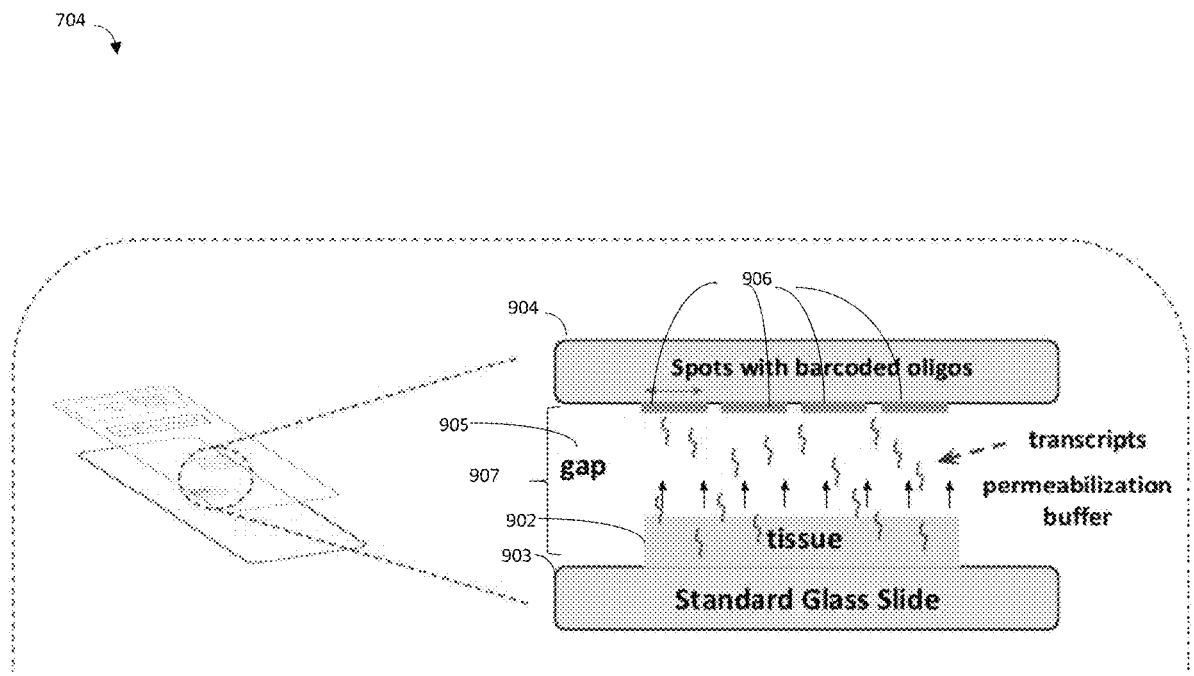
FIG. 9A is a schematic diagram depicting an exemplary permeabilization solution interaction between a tissue slide and an array slide in a sandwich configuration in accordance with some example implementations.

FIG. 9A is a schematic diagram depicting an exemplary permeabilization solution interaction 704 between a tissue slide and an array slide in a sandwich configuration in accordance with some example implementations. In the exemplary configuration of FIG. 9A, a sample (e.g., a tissue or biological sample) 902 is disposed on a pathology slide 903 and is sandwiched between the pathology slide 903 and a slide 904 (e.g., an array slide, e.g., a gene expression slide) that is populated with spatially-barcoded capture probes 906. As shown, the slide 904 is in a superior position to the pathology slide 903. In some embodiments, the pathology slide 903 may be positioned superior to the slide 904. When a permeabilization solution 905 is applied to a gap 907 between the pathology slide 903 and the slide 904, the permeabilization solution 905 may create a permeabilization buffer which permeabilizes or digests the sample 902 and analytes (e.g., mRNA transcripts and/or other molecules) 908 of the tissue sample 902 may release, diffuse across the gap 907 toward the capture probes 906, and bind on the capture probes 906. After the analytes 908 (e.g., transcripts) bind on the capture probes 906, a reverse transcription reaction may occur, generating a cDNA library associated with a particular spatial barcode (e.g., a cDNA library wherein library members comprise spatial barcodes). Barcoded cDNA libraries (e.g., library members) may be mapped back to a specific spot on a capture area of the capture probes 906. This data (e.g., gene expression data)

may be subsequently layered over a high-resolution microscope image of the tissue section ((e.g., taken at 804 of FIG. 8), making it possible to visualize the expression of any mRNA, or combination of mRNAs, within the morphology of the tissue in a spatially-resolved manner.

The sandwich configuration of the sample 902, the pathology slide 903 and the slide 904 may provide advantages over other methods of spatial analysis and/or analyte capture. For example, the sandwich configuration may reduce a burden of users to develop in house tissue sectioning and/or tissue mounting expertise. Further, the sandwich configuration may decouple sample preparation/tissue imaging from the barcoded array (e.g., spatially-barcoded capture probes 906) and enable selection of a particular region of interest of analysis (e.g., for a tissue section larger than the barcoded array). The sandwich configuration also beneficially enables spatial omics (e.g., transcriptomics) assays without having to place a tissue section 902 directly on the array slide (e.g., slide 904) which may reduce cost and risk of mistakes/issues during sample preparation. The sandwich configuration may also provide an improvement of sensitivity and spatial resolution by vertically confining target molecules within the diffusion distance.

Figure 9B:
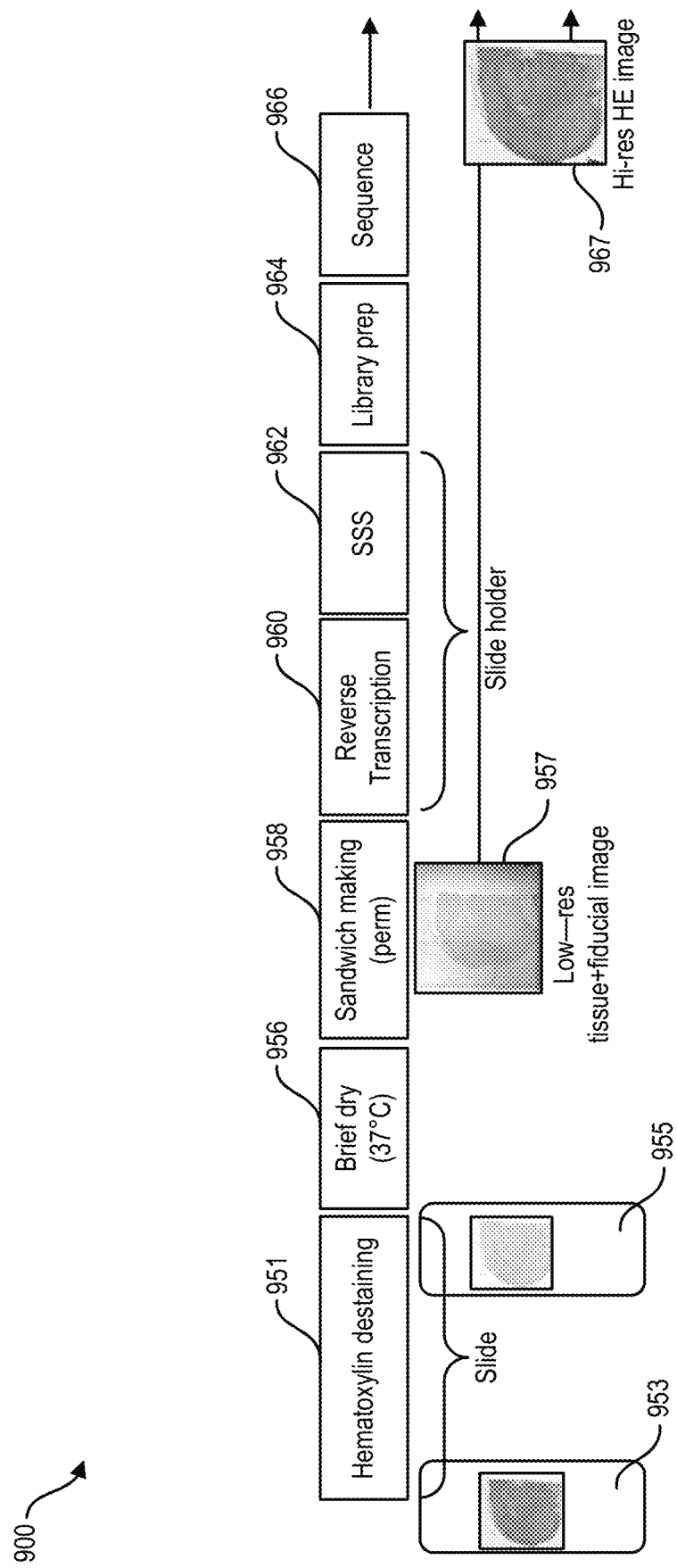
FIG. 9B depicts a workflow for performing sample analysis in accordance with example implementations.

FIG. 9B depicts an exemplary experimental workflow 900 for performing sample analysis in accordance with example implementations. As shown, the workflow 900 includes a destaining step 951, a drying step 956, a sandwich making (e.g., permeabilization) step 958, a reverse transcription step 960, a second strand synthesis (SSS) 962, a library prep step 964, and a sequence step 966. The destaining step 951 may include a hematoxylin destaining of a tissue slide. As further shown, the step 951 may include an initial stained tissue slide 953 and, after a destaining process, a destained tissue slide 955. At the drying step 956, the tissue slide 955 may be dried for a duration at 37° C. or another temperature. At step 958, the tissue slide 955 may be sandwiched in a sample handling apparatus with an array slide (e.g., slide 904 with barcoded array capture probes 906) and a permeabilization medium (e.g., permeabilization solution 905).

In some aspects, during the step 958, the sample handling apparatus may capture an image 957 of the tissue section. The image may include a low resolution image of the tissue section and any fiducial on the tissue slide. At step 960, the workflow 900 may include performing reverse transcription on the second substrate. Step 962, the workflow 900 may include performing second strand synthesis on the second substrate. At step 964, the workflow 900 may include generating a cDNA library associated with a particular spatial barcode of the array slide. The sequence step 966 may include library amplicons may be sequenced and analyzed to decode spatial information. Barcoded cDNA libraries may be mapped back to a specific spot on a capture area of the capture probes 906. This gene expression data may be subsequently layered over a high-resolution microscope image of the tissue section. In some aspects, during or before sequencing, a high resolution image 967 of the tissue section may be captured for the layering described above.

The methods described above for analyzing biological samples, such as the sandwich configuration described above, can be implemented using a variety of hardware components. In this section, examples of such components are described. However, it should be understood that in general, the various steps and techniques discussed herein can be performed using a variety of different devices and system components, not all of which are expressly set forth.

Figure 10:
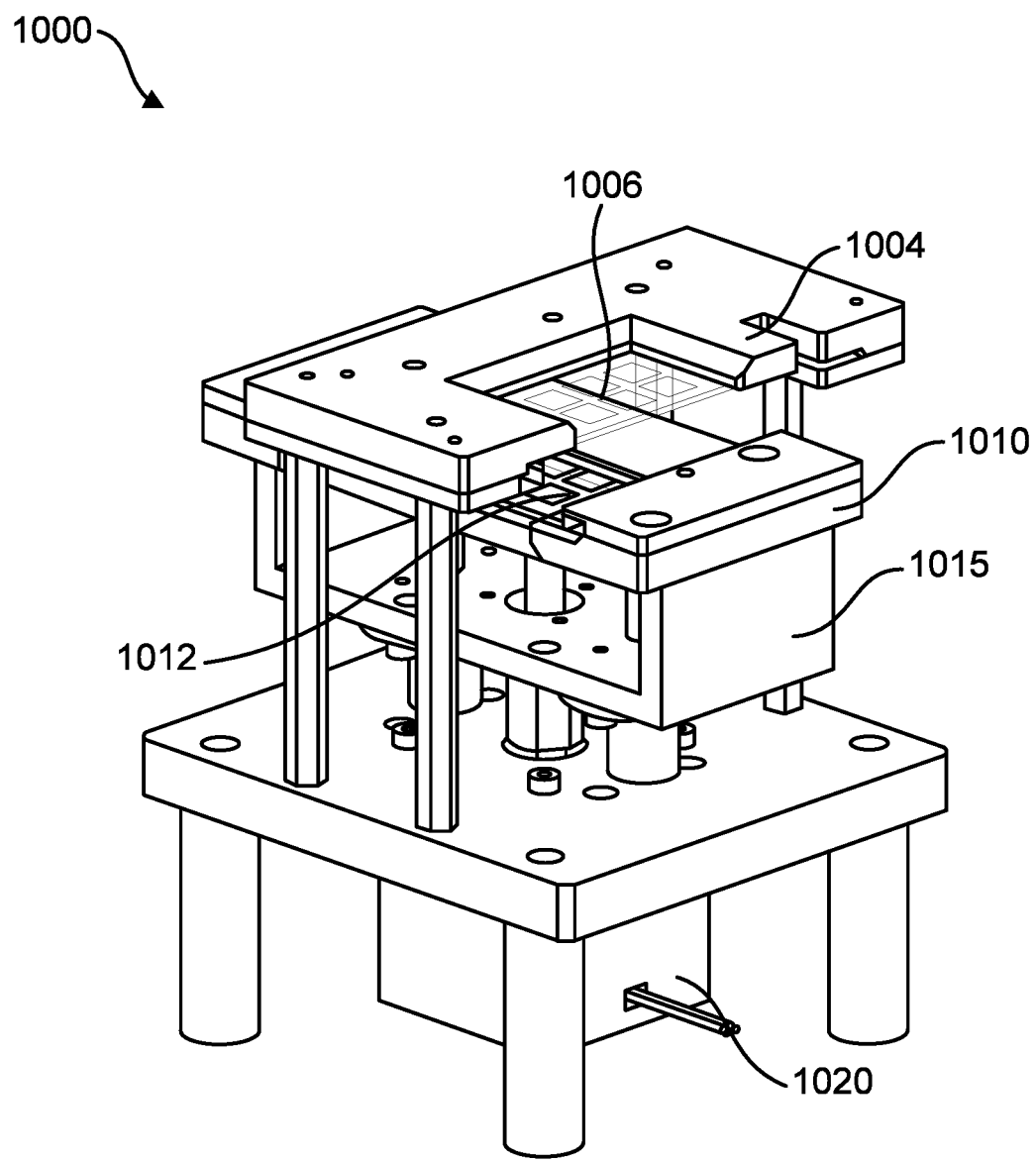
FIG. 10 is a schematic diagram showing an example sample handling apparatus in accordance with some example implementations.

FIG. 10 is a schematic diagram showing an example sample handling apparatus 1000 in accordance with some example implementations. Sample handling apparatus 1000, also referred to as sample holder 1000, includes a first member 1004 that holds a first substrate 1006 on which a sample 902 may be positioned. The first member 1004 may include a first retaining mechanism configured to retain the first substrate 1006 in a fixed position along an axis and disposed in a first plane. As shown, the sample handling apparatus 1000 also includes a second member 1010 that holds a second substrate 1012. The second member 1010 may include a second retaining mechanism configured to retain the second substrate 1012 disposed in a second plane. The second substrate 1012 may include a barcoded array (e.g., array of spatially-barcoded capture probes 906), as described above. As shown, the sample handling apparatus 1000 also includes an adjustment mechanism 1015 configured to move the second member 1010. The adjustment mechanism 1015 may be coupled to the second member 1010 and includes a linear actuator 1020 configured to move the second member 1010 along a z axis orthogonal to the second plane. In some aspects, the adjustment mechanism 1015 may be alternatively or additionally coupled to the first member 1004, e.g., configured to move the first member 1004.

In some embodiments, the first substrate 1006 overlaps with the second substrate 1012 in accordance with some example implementations. The overlap may occur along an axis orthogonal to the first substrate 1006 and/or orthogonal to the second substrate 1012. In some aspects, a camera may capture an image of the overlap area that may be used as part of the spatial analysis further described herein.

Figure 11:
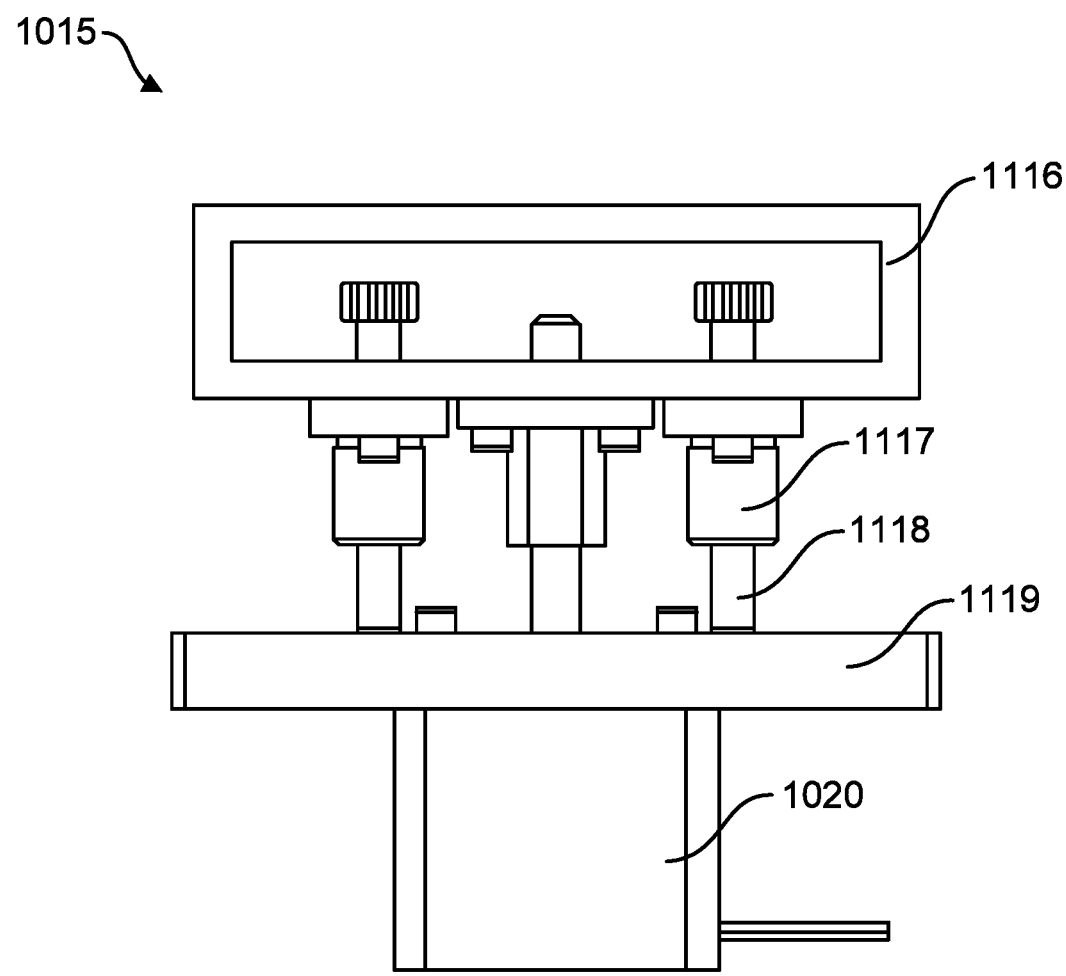
FIG. 11 is diagram of an example adjustment mechanism in accordance with some example implementations.

FIG. 11 is diagram of an example adjustment mechanism 1015 in accordance with some example implementations. The adjustment mechanism 1015 may include a moving plate 1116, a bushing 1117, a shoulder screw 1118, a motor bracket 1119, and the linear actuator 1020. The moving plate 1116 may be coupled to the second member 1010 and adjust the separation distance (e.g., gap 907) along a z axis (e.g., orthogonal to the second substrate 1012) by moving the moving plate 1116 up in a superior direction toward the first substrate 406. The movement of the moving plate 1106 may be accomplished by the linear actuator 1020 configured to move the second member 1010 along the axis orthogonal to the second plane at a velocity. The velocity may be controlled by a controller communicatively coupled to the linear actuator 1020. For example, the velocity may be configured to move the moving plate between at least 0.1 mm/sec to 2 mm/sec. In some aspects, the velocity of the moving plate (e.g., closing the sandwich) may affect bubble generation or trapping within the permeabilization solution 905. Further, the linear actuator may be configured to move the moving plate 1106 with an amount of force (e.g., between 0.1-4.0 pounds of force). The controller may be configured to adjust the velocity and/or the amount of force of the linear actuator 1020 to accomplish a desired combination of velocity and force for the moving plate 1116.

In some aspects, the velocity of the moving plate (e.g., closing the sandwich) may affect bubble generation or trapping within the permeabilization solution 905. It may be advantageous to minimize bubble generation or trapping within the permeabilization solution during the "sandwiching" process, as bubbles can interfere with the migration of analytes via the solution to the array. In some embodiments, the closing speed is selected to minimize bubble generation or trapping within the permeabilization solution 905. In some embodiments, the closing speed is selected to reduce the time it takes the flow front of a reagent medium from an initial point of contact with the first and second substrate to sweep across the sandwich area (also referred to herein as "closing time". In some embodiments, the closing speed is selected to reduce the closing time to less than about 1100 ms. In some embodiments, the closing speed is selected to reduce the closing time to less than about 1000 ms. In some embodiments, the closing speed is selected to reduce the closing time to less than about 900 ms. In some embodiments, the closing speed is selected to reduce the closing time to less than about 750 ms. In some embodiments, the closing speed is selected to reduce the closing time to less than about 600 ms. In some embodiments, the closing speed is selected to reduce the closing time to about 550 ms or less. In some embodiments, the closing speed is selected to reduce the closing time to about 370 ms or less. In some embodiments, the closing speed is selected to reduce the closing time to about 200 ms or less. In some embodiments, the closing speed is selected to reduce the closing time to about 150 ms or less.

Figure 12A:
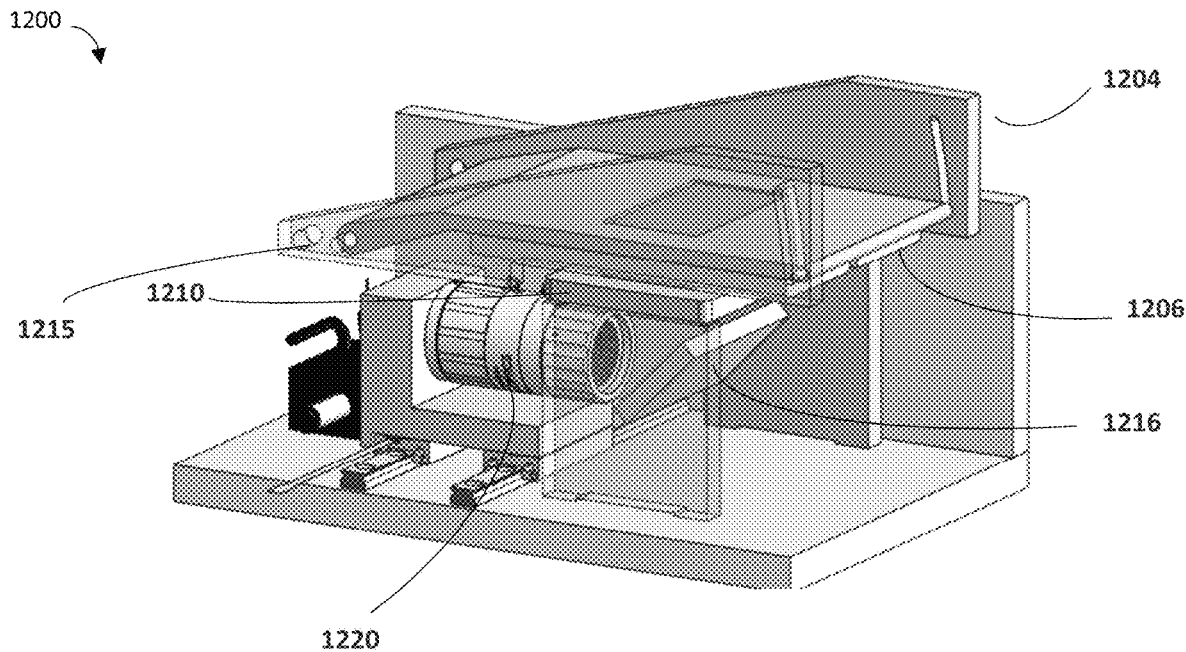
FIG. 12A is a perspective view of an example sample handling apparatus in a closed position in accordance with some example implementations.

FIG. 12A is a perspective view of an example sample handling apparatus 1200 in a closed position in accordance with some example implementations. As shown, the sample handling apparatus 1200 includes a first member 1204, a second member 1210, an image capture device 1220, a first substrate 1206, a hinge 1215, and a mirror 1216. The hinge 1215 may be configured to allow the first member 1204 to be positioned in an open or closed configuration by opening and/or closing the first member 1204 in a clamshell manner along the hinge 1215.

Figure 12B:
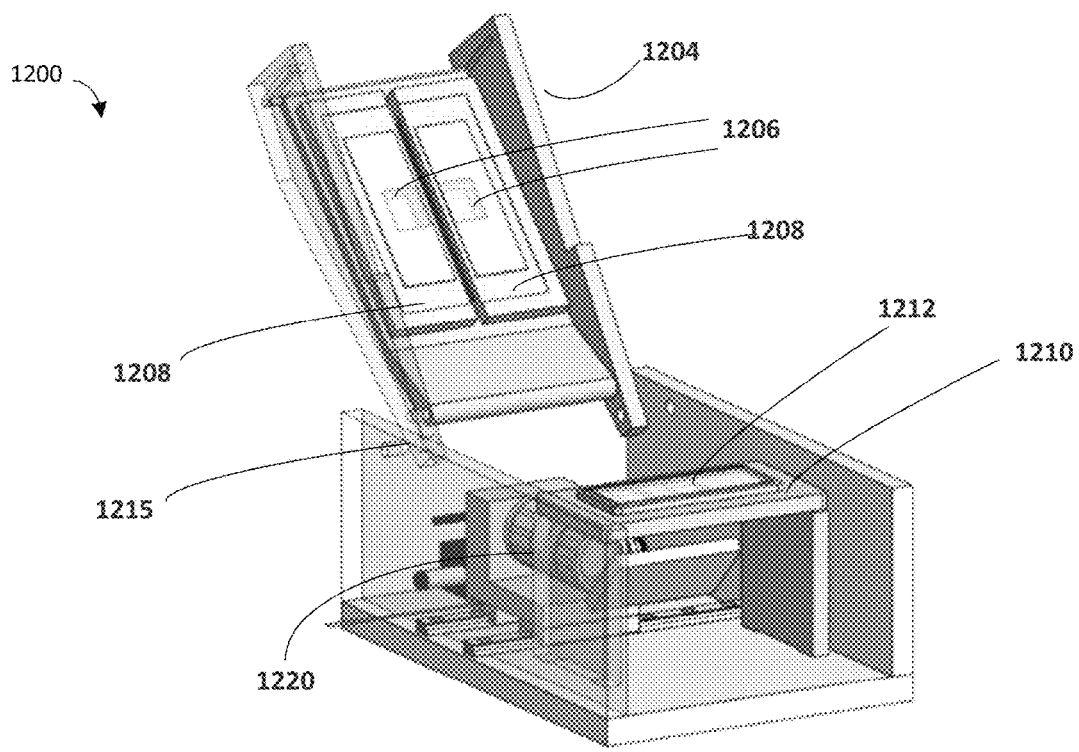
FIG. 12B is a perspective view of the example sample handling apparatus in an open position in accordance with some example implementations.

FIG. 12B is a perspective view of the example sample handling apparatus 1200 in an open position in accordance with some example implementations. As shown, the sample handling apparatus 1200 includes one or more first retaining mechanisms 1208 configured to retain one or more first substrates 1206. In the example of FIG. 12B, the first member 1204 is configured to retain two first substrates 1206, however the first member 1204 may be configured to retain more or fewer first substrates 1206.

In some aspects, when the sample handling apparatus 1200 is in an open position (as in FIG. 12B), the first substrate 1206 and/or the second substrate 1212 may be loaded and positioned within the sample handling apparatus 1200 such as within the first member 1204 and the second member 1210, respectively. As noted, the hinge 1215 may allow the first member 1204 to close over the second member 1210 and form a sandwich configuration (e.g., the sandwich configuration shown in FIG. 9).

In some aspects, after the first member 1204 closes over the second member 1210, an adjustment mechanism (not shown) of the sample handling apparatus 1200 may actuate the first member 1204 and/or the second member 1210 to form the sandwich configuration for the permeabilization step (e.g., bringing the first substrate 1206 and the second substrate 1212 closer to each other and within a threshold distance for the sandwich configuration). The adjustment mechanism may be configured to control a speed, an angle, or the like of the sandwich configuration.

In some embodiments, the tissue sample (e.g., sample 902) may be aligned within the first member 1204 (e.g., via the first retaining mechanism 1208) prior to closing the first member 1204 such that a desired region of interest of the sample 902 is aligned with the bar-coded array of the array slide (e.g., the slide 904), e.g., when the first and second substrates are aligned in the sandwich configuration. Such alignment may be accomplished manually (e.g., by a user) or automatically (e.g., via an automated alignment mechanism). After or before alignment, spacers may be applied to the first substrate 1206 and/or the second substrate 1212 to maintain a minimum spacing between the first substrate 1206 and the second substrate 1212 during sandwiching. In some aspects, the permeabilization solution (e.g., permeabilization solution 905) may be applied to the first substrate 1206 and/or the second substrate 1212. The first member 1204 may then close over the second member 1210 and form the sandwich configuration. Analytes (e.g., mRNA transcripts and/or other molecules) 908 may be captured by the capture probes 906 and may be processed for spatial analysis.

In some embodiments, during the permeabilization step, the image capture device 1220 may capture images of the overlap area (e.g., overlap area 710) between the tissue 902 and the capture probes 906. If more than one first substrates 1206 and/or second substrates 1212 are present within the sample handling apparatus 1200, the image capture device 1220 may be configured to capture one or more images of one or more overlap areas 710.

It may be desirable to perform real-time alignment of a tissue slide (e.g., the pathology slide 903) with an array slide (e.g., the slide 904 with barcoded capture probes 906). In some implementations, such real-time alignment may be achieved via motorized stages and actuators of a sample handling apparatus (e.g., the sample handling apparatus 1000, the sample handling apparatus 1200, or the like).

Thus, the devices of the disclosure can advantageously align (e.g., along an XY axis) 7B). (e.g., moving the first substrate and/or the second substrate toward each other along a Z axis) in an aligned manner. For example, the adjustment mechanism 1015 may be configured to move one or more first members 1004 along an axis orthogonal to the first members 1004 (e.g., along a z axis) to facilitate sandwiching of the first substrate and/or the second substrate.

Proper alignment of the first and second substrates may be beneficial in spatial transcriptomics applications as the sample (e.g., the biological sample 902) may align with a barcoded area of a substrate (e.g., capture probes 906) to provide accurate spatial data.

I. Fluid Delivery Methods and Kits

Analytes within a biological sample are generally released through disruption (e.g., permeabilization, digestion, etc.) of the biological sample or may be released without disruption. Various methods of permeabilizing (e.g., any of the permeabilization reagents and/or conditions described herein) a biological sample are described herein, including for example including the use of various detergents, buffers, proteases, and/or nucleases for different periods of time and at various temperatures. Additionally, various methods of delivering fluids (e.g., a buffer, a permeabilization solution) to a biological sample are described herein including the use of a substrate holder (e.g., sandwich assembly, sandwich configuration, as described herein).

Provided herein are methods for delivering a fluid to a biological sample disposed on an area of a first substrate and an array disposed on a second substrate.

In some embodiments and with reference to FIG. 9, the sandwich configuration described herein between a tissue sample slide (e.g., pathology slide 903) and an array slide (e.g., slide 904 with barcoded capture probes 906) may require the addition of a liquid reagent (e.g., permeabilization solution 905 or other target molecule release and capture solution) to fill a gap (e.g., gap 907). It may be desirable that the liquid reagent be free from air bubbles between the slides to facilitate transfer of target molecules with spatial information. Additionally, air bubbles present between the slides may obscure at least a portion of an image capture of a desired region of interest. Accordingly, it may be desirable to ensure or encourage suppression and/or elimination of air bubbles between the two slides during a permeabilization step (e.g., step 104).

In some aspects, it may be possible to reduce or eliminate bubble formation between the slides using a variety of filling methods and/or closing methods.

Workflows described herein may include contacting a drop of the liquid reagent disposed on a first substrate (e.g., the first substrate 1006, 1206, or the like) or a second substrate (e.g., the second substrate 1012, 1212, or the like) with at least a portion of a first substrate (e.g., the first substrate 1006, 1206, or the like) or second substrate (e.g., the second substrate 1012, 1212, or the like), respectively. In some embodiments, the contacting comprises bringing the two substrates into proximity such that the sample on the first substrate is aligned with the barcode array of capture probes on the second substrate.

In some embodiments, the drop includes permeabilization reagents (e.g., any of the permeabilization reagents described herein). In some embodiments, the rate of permeabilization of the biological sample is modulated by delivering the permeabilization reagents (e.g., a fluid containing permeabilization reagents) at various temperatures.

In some embodiments, the permeabilization reagents are dried permeabilization reagents. In some embodiments, the dried permeabilization reagents are disposed on a substrate (e.g., the first substrate, the second substrate). In some embodiments, delivering the fluid (e.g., by any of the fluid delivery methods described herein) solubilizes the dried permeabilization reagents. In some embodiments, solubilizing the permeabilization reagents results in permeabilization of the biological sample. In some embodiments, delivering the fluid to solubilize dried reagents is delivered via an aperture in a gasket. In some embodiments, delivering the fluid to solubilize dried reagents is delivered through a via-hole. In some embodiments, the fluid solubilizing dried reagents includes the use of a syringe. In some embodiments, the fluid solubilizing dried reagents includes the capillary flow.

The permeabilization solution 905) may fill a gap (e.g., the gap 907) between a tissue slide (e.g., slide 903) and a capture slide (e.g., slide 904 with barcoded capture probes 906) to warrant or enable transfer of target molecules with spatial information. Described herein are examples of filling methods that may suppress bubble formation and suppress undesirable flow of transcripts and/or target molecules or analytes. Robust fluidics in the sandwich making described herein may preserve spatial information by reducing or preventing deflection of molecules as they move from the tissue slide to the capture slide.

Figure 13A:
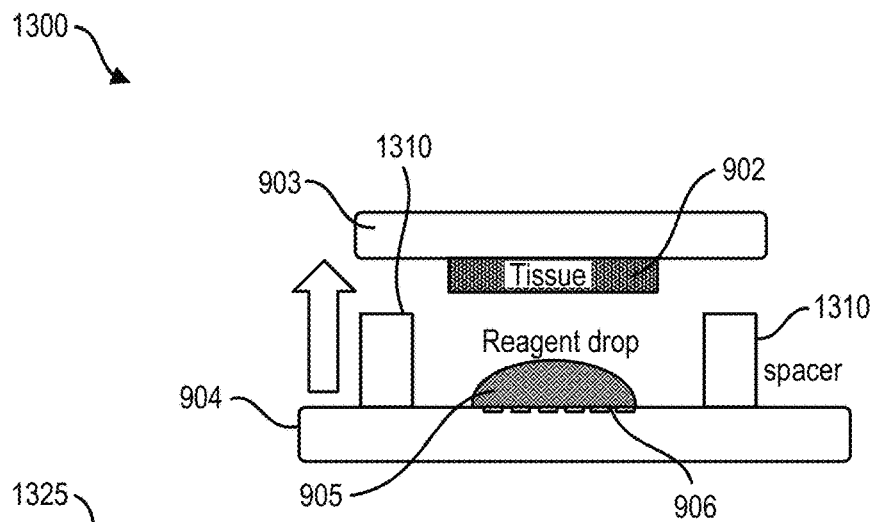
FIG. 13A shows an exemplary sandwich configuration in accordance with some example implementations.

FIG. 13A shows an exemplary sandwich configuration 1300 where a first substrate (e.g., pathology slide 903), including a biological sample 902 (e.g., a tissue section), and a second substrate (e.g., slide 904 including spatially barcoded capture probes 906) are brought into proximity with one another. As shown in FIG. 13A a liquid reagent drop (e.g., permeabilization solution 905) is introduced on the second substrate in proximity to the capture probes 906 and in between the biological sample 902 and the second substrate (e.g., slide 904). The permeabilization solution 905 may release analytes that can be captured by the capture probes 906 of the array. As further shown, one or more spacers 1310 may be positioned between the first substrate (e.g., pathology slide 903) and the second substrate (e.g., slide 904). The one or more spacers 1310 may be configured to maintain a separation distance between the first substrate and the second substrate. While the one or more spacers 1310 is shown as disposed on the second substrate, the one or more spacers 1310 may additionally or alternatively be disposed on the first substrate.

Figure 13B:
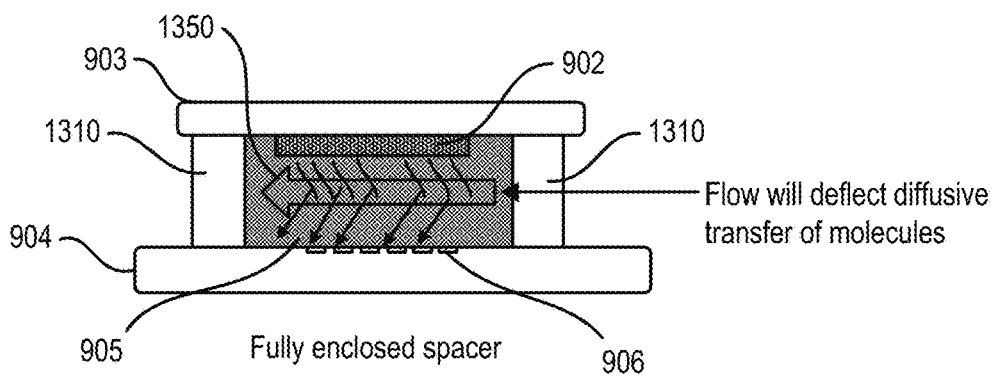
FIG. 13B shows a fully formed sandwich creating a chamber formed from the one or more spacers, the first substrate, and the second substrate in accordance with some example implementations.

FIG. 13B shows a fully formed sandwich creating a chamber 1350 formed from the one or more spacers 1310, the first substrate (e.g., the pathology slide 903), and the second substrate (e.g., the slide 904) in accordance with some example implementations. In the example of FIG. 13B, the liquid reagent (e.g., the permeabilization solution 905) fills the volume of the chamber 1350 and may create a permeabilization buffer that allows analytes (e.g., mRNA transcripts and/or other molecules) to diffuse from the biological sample 902 toward the capture probes 906 of the slide 904. In some aspects, any flow of the permeabilization buffer may deflect transcripts and/or molecules from the biological sample 902 and may affect diffusive transfer of analytes for spatial analysis. A partially or fully sealed chamber 1350 resulting from the one or more spacers 1310, the first substrate, and the second substrate may reduce or prevent flow from undesirable convective movement of transcripts and/or molecules over the diffusive transfer from the biological sample 902 to the capture probes 906.

Figure 13C:
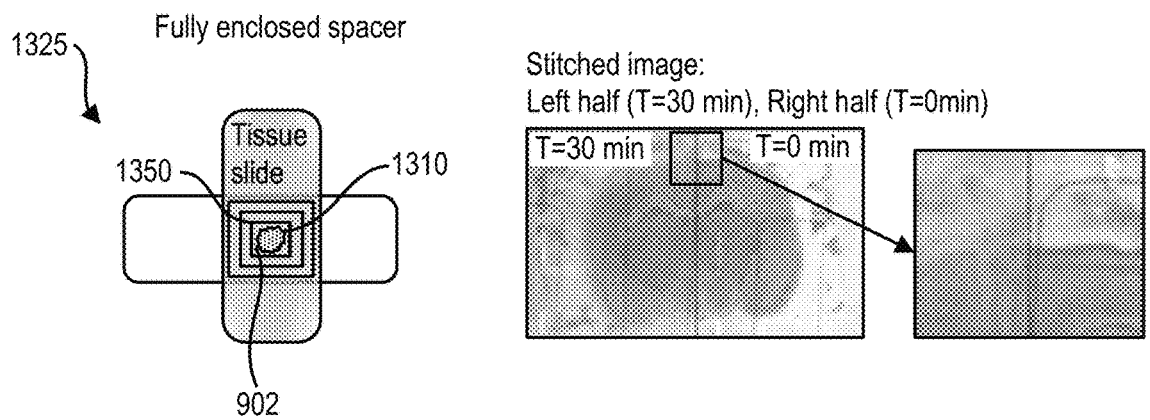
FIG. 13C depicts a top view of the configuration of FIG. 13B.

FIG. 13C depicts a top view of the configuration 1325 of FIG. 13B. As shown, the one or more spacers 1310 may fully enclose and surround the biological sample 902 and form the chamber 1350 when sandwiched between the first substrate and the second substrate. The right hand side of FIG. 13C depicts an example of reduced convection during by capturing images of the sample 902 at the start of the sandwich and at the end of the sandwich. Half of such images may be stitched together to pronounce the dominant diffusion and suppressed convection during sandwiching.

The one or more spacers 1310 may be configured to maintain a separation distance between the first substrate and the second substrate. The one or more spacers 1310 can be placed on the first substrate adjacent to the biological sample 902 and in between the first substrate and the second substrate. The one or more spacers 1310 can be placed on the second substrate adjacent to the array 906 and in between the first substrate and the second substrate. By doing so, the one or more spacers 1310 can create a chamber (e.g., chamber 1350) in which solutions (e.g., a buffer, a permeabilization solution 905) are contained throughout the permeabilization and analyte migration process. In some embodiments, more than one spacer is used.

In some embodiments, the one or more spacers 1310 is configured to maintain a separation distance between first and second substrates that is between about 2 microns and 1 mm (e.g., between about 2 microns and 800 microns, between about 2 microns and 700 microns, between about 2 microns and 600 microns, between about 2 microns and 500 microns, between about 2 microns and 400 microns, between about 2 microns and 300 microns, between about 2 microns and 200 microns, between about 2 microns and 100 microns, between about 2 microns and 25 microns, between about 2 microns and 20 microns, or between about 2 microns and 10 microns), measured in a direction orthogonal to the surface of first substrate that supports the sample. In some instances, the separation distance is about 2, 3, 4, 5, 6, 7, 8, 9, 10, 11, 12, 13, 14, 15, 16, 17, 18, 19, 20, 21, 22, 23, 24, or 25 microns. In some embodiments, the separation distance is less than 50 microns. In some embodiments, the separation distance is less than 25 microns. In some embodiments, the separation distance is less than 20 microns. The separation distance may include a distance of at least 2 μm.

In some embodiments, the separation distance is measured in a direction orthogonal to a surface of the first substrate that supports the biological sample.

In some embodiments, the one or more spacers 1310 have a height that is between about 2 microns and 1 mm (e.g., between about 2 microns and 800 microns, between about 2 microns and 700 microns, between about 2 microns and 600 microns, between about 2 microns and 500 microns, between about 2 microns and 400 microns, between about 2 microns and 300 microns, between about 2 microns and 200 microns, between about 2 microns and 100 microns, between about 2 microns and 25 microns, between about 2 microns and 20 microns, or between about 2 microns and 10 microns), measured in a direction orthogonal to the surface of first substrate that supports the sample. In some instances, the one or more spacers 1310 have a height that is about 2, 3, 4, 5, 6, 7, 8, 9, 10, 11, 12, 13, 14, 15, 16, 17, 18, 19, 20, 21, 22, 23, 24, or 25 microns. In some embodiments, the one or more spacers 1310 have a height that is less than 50 microns. In some embodiments the one or more spacers 1310 have a height that is less than 25 microns. In some embodiments, the one or more spacers 1310 have a height that is less than 20 microns.

In some instances, the separation between the first and second substrates can be maintained between 50 microns and 1 mm (e.g., between 50 microns and 800 microns, between 50 microns and 700 microns, between 50 microns and 600 microns, between 50 microns and 500 microns, between 50 microns and 400 microns, between 50 microns and 300 microns, between 50 microns and 200 microns, between 50 microns and 100 microns), measured in a direction orthogonal to the surface of the first substrate that supports the sample.

In some embodiments, the one or more spacers 1310 have a height of about 2 µm, about 12.5 µm, about 15 µm, about 17.5 µm, about 20 µm, about 22.5 µm, or about 25 µm. In some embodiments, the one or more spacers 1310 have a height of about 2 µm, about 12.5 µm, about 15 µm, about 17.5 µm, about 20 µm, about 22.5 µm, or about 25 µm. In some embodiments, the spacer has a height of about 50 µm, about 100 µm, about 200 µm, about 300 µm, about 400 µm, about 500 µm, about 600 µm, about 700 µm, about 800 µm, about 900 µm, or about 1000 µm. in some aspects, the one or more spacers 1310 may have a height ranging from 1 to 100 µm. The height or thickness of the one or more spacers 1310 may be based on the diffusive broadening of the fluid as described herein.

The one or more spacers 1310 may be formed of a material having uniform thickness or of a material having a variable (e.g., beveled) thickness. In some embodiments, the spacer material is selected to be fluidically sealable. The use of a substantially fluidically sealable spacer material may be advantageous for reducing lateral flow within the chamber formed from the spacer, the first substrate, and the second substrate during sandwiching, e.g., lateral flow due to capillary flow outside the chamber. For example, the one or more spacers 1310 may include graphite, polyester, Polytetrafluoroethylene (PTFE), polyamide, polychlorotrifluoroethylene (PCTFE), poly(ethene-co-tetrafluoroethene) (ETFE), PEEK (Polyether ether ketone), silicone elastomer, and the like.

Figure 30:
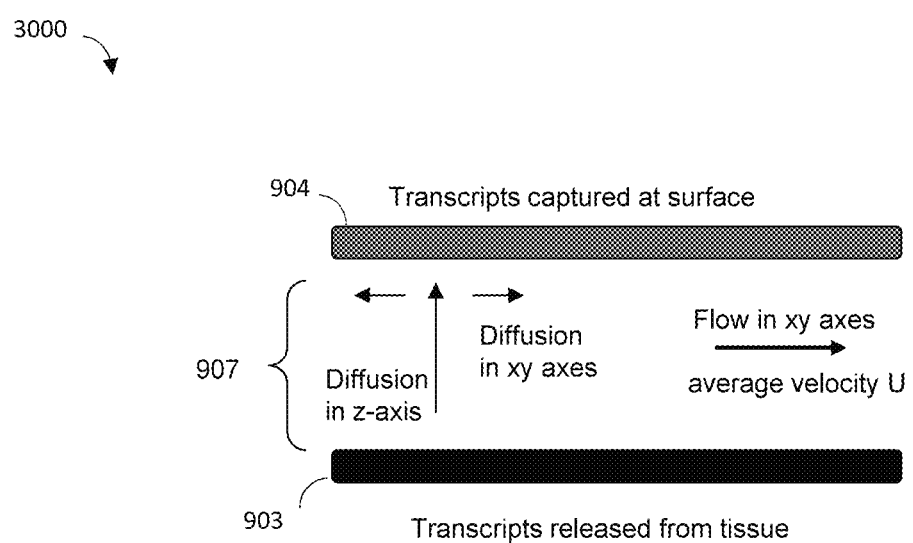
FIG. 30 is a schematic diagram depicting an exemplary permeabilization solution interaction between a tissue slide and an array slide in a sandwich configuration in accordance with some example implementations.

In some implementations, the chamber 1350 and one or more spacers 1310 may reduce or suppress flow of a fluid (e.g., permeabilization solution 905) during sandwiching. FIG. 30 is a schematic diagram 3000 depicting an exemplary permeabilization solution interaction between a tissue slide (e.g., slide 903) and an array slide (e.g., slide 904 with capture probes 906) in a sandwich configuration in accordance with some example implementations. As shown, analytes (e.g., mRNA transcripts and/or other molecules) may release from the tissue slide 903 toward the array slide 904 and across a gap 907. As described above with respect to FIG. 9, the gap 907 may include a permeabilization solution 905 that may promote the release of analytes (e.g., mRNA transcripts and/or other molecules). As further shown in the example of FIG. 30, the analytes may diffuse across the gap 907 along the Z axis and toward the array slide 904 and may also diffuse along the XY axis. In some aspects, the permeabilization solution 905 may include a flow along the XY axis having an average velocity, U. Such flow may cause a lateral displacement of the analytes due to the flow and may affect proper analyte (e.g., mRNA transcript and/or other molecule) capture at the array slide 904. In some implementations, a certain amount of flow may be acceptable to achieve accurate results and capture. For example, an acceptable amount of flow may be achieved when lateral displacement due to flow is less than a lateral diffusive broadening (e.g., displacement due to diffusion along the XY axis). In some aspects, acceptable amount of flow may be based on a gap diffusion time and/or a gap height. For example, an amount of flow may be acceptable when the lateral flow velocity, U, times a gap diffusion time is less than the gap 907 height. In another example, the amount of flow may be acceptable when the lateral flow velocity, U, times that gap height squared divided by a diffusion coefficient (e.g., $U*h2/D<h$). An example acceptance criteria for a flow amount may include a lateral flow velocity U less than a threshold that is some percentage (e.g., 70%) of a sandwich time. Some exemplary acceptable values for the lateral flow velocity U may include 0.1-6 um/sec.

Figure 31A:
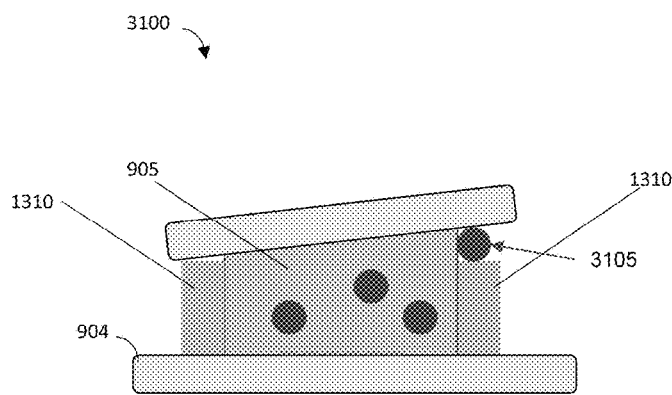
FIG. 31A is a diagram of an example sandwich configuration with a flow tracking particle within a permeabilization solution in accordance with some example implementations.

In some aspects, there may be different methods to measure flow. In one aspect, flow tracking particles may be included in a fluid (e.g., the permeabilization solution 905). FIG. 31A is a diagram 3100 of an example sandwich configuration with a flow tracking particle 3105 within the permeabilization solution 905. The flow tracking particle 3105 may be 5-10 um in size and may be visible from an imaging system of a sample holder as described herein to measure an amount of lateral diffusion due to flow during sandwiching.

Figure 31B:
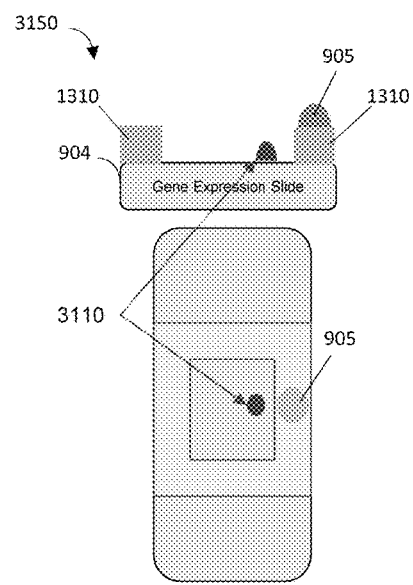
FIG. 31B is a diagram of an example dye on an array slide in accordance with some example implementations.

In another aspect, a dye may be included on an array slide 904 to measure flow. FIG. 31B is a diagram 3150 of an example dye 3110 on an array slide 904. In the presence of flow, the dye 3110 may streak and show a direction and/or amount of flow during sandwiching, such as through imaging as described herein.

Figure 32A:
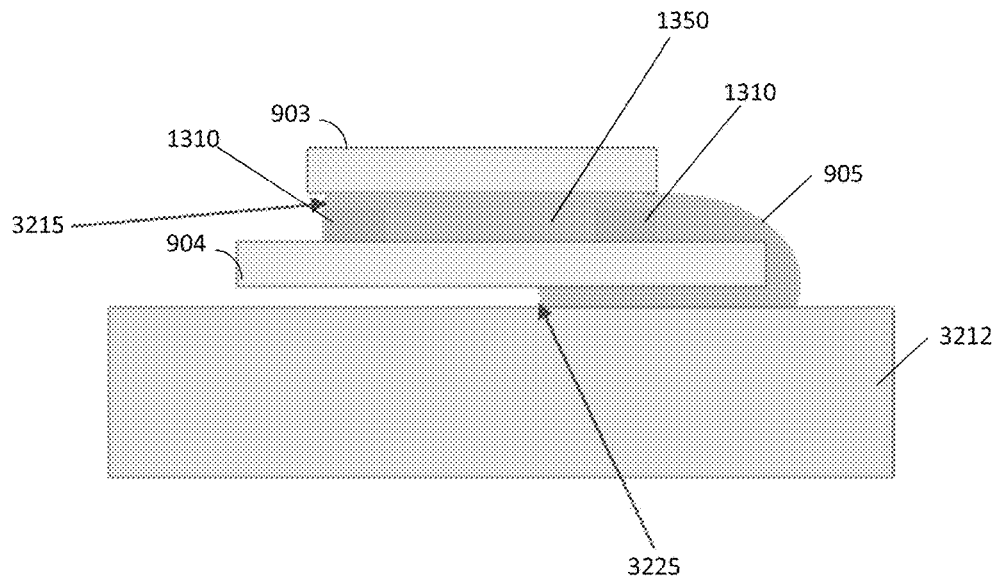
FIG. 32A depicts an example sandwich configuration in accordance with some exemplary implementations of capillary flow outside the sandwich chamber.

In some aspects, an amount of flow during sandwiching may be affected by capillary flow outside the sandwich chamber (e.g., chamber 1350). FIG. 32A depicts an example sandwich configuration 3200 in accordance with some exemplary implementations of capillary flow outside the sandwich chamber. As shown, a chamber 1350 includes one or more spacers 1310 and an opening 3215. Without wishing to be bound by theory, the opening 3215 may allow a portion of the permeabilization solution 905 to leak outside the chamber 1350 under certain conditions. As shown in the example of FIG. 32A, and amount of permeabilization solution 905 has leaked out one side of the chamber 1350 and has seeped under the slide 903 and between a slide holder 3212. As further shown, an air-water interface 3225 may develop as a result of capillary flow of the permeabilization solution 905 outside of the chamber 1350. Accordingly, provided herein are methods and sandwich configurations to reduce capillary flow and associated flow spikes.

Figure 32B:
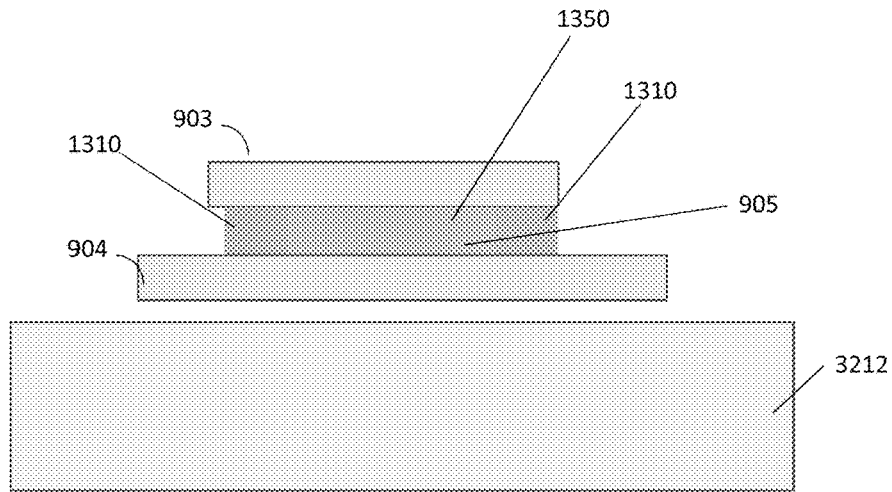
FIG. 32B depicts an example sandwich configuration in accordance with some exemplary implementations.

FIG. 32B depicts one such example sandwich configuration 3250 in accordance with some exemplary implementations. In the example of FIG. 32B, the one or more spacers 1310 include a sealing spacer that may be substantially fluidically sealable or made of substantially fluidically sealable material. For example, the substantially fluidically sealable material may include PTFE (Polytetrafluoroethylene), silicone, PCTFE (polychlorotrifluoroethylene), Polyimide, ETFE (poly(ethene-co-tetrafluoroethene), PEEK (Polyether ether ketone), or the like. The use of the substantially fluidically sealable spacer 1310 may reduce or remove random flow spikes and increase accuracy or acceptability of transcript diffusion.

Figure 33:
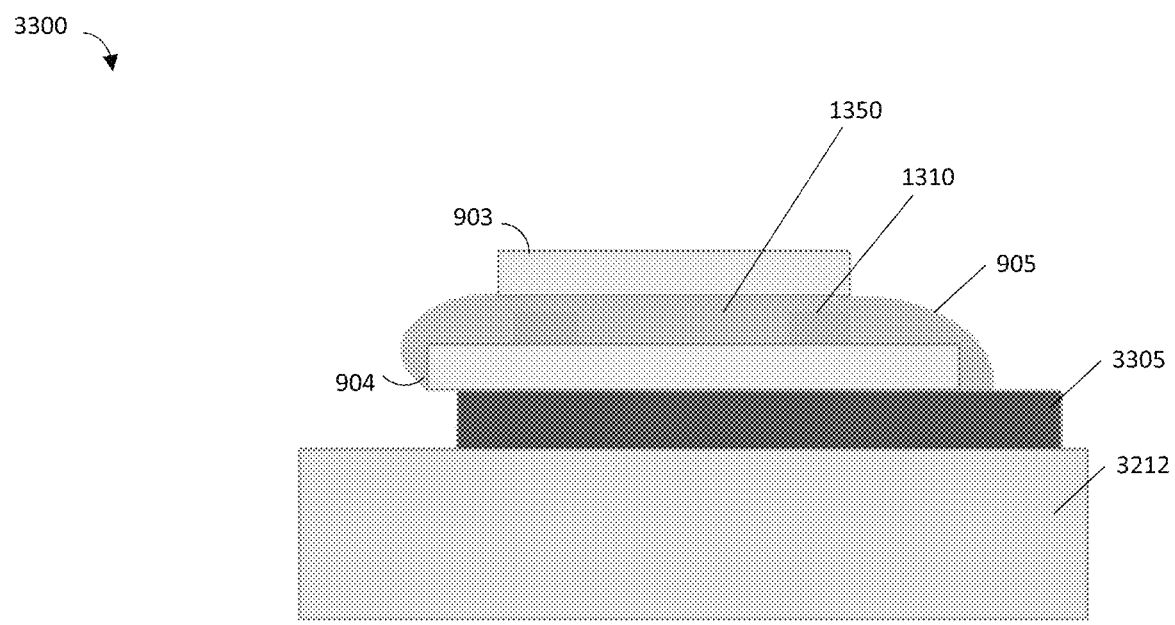
FIG. 33 depicts an example sandwich configuration in accordance with some exemplary implementations.

In some aspects, a material or backing may be added to the slide 903 and/or the slide 904 to reduce or remove the effects of capillary flow from excess fluid (e.g., permeabilization solution 905) within the chamber 1350. FIG. 33 depicts an example sandwich configuration 3300 in accordance with some exemplary implementations. As shown, the sandwich configuration 3300 includes a backing 3305 between the slide 904 and the slide holder 3212. The backing 3305 may be applied to a back surface of the slide 904 or to a superior surface of the slide holder 3212. The backing 3305 may be configured to prevent fluid (e.g., permeabilization solution 905) from traveling beneath the slide 904 and suppress capillary flow. In some aspects, the backing 3305 may include silicone rubber, organic rubber, an elastomer, or other material. The backing 3305, the slide 904, and/or the slide holder 3212 may include an adhesive or adhesive surface to secure the backing 3305 to the slide 904 and/or the slide holder 3212.

Figure 43:
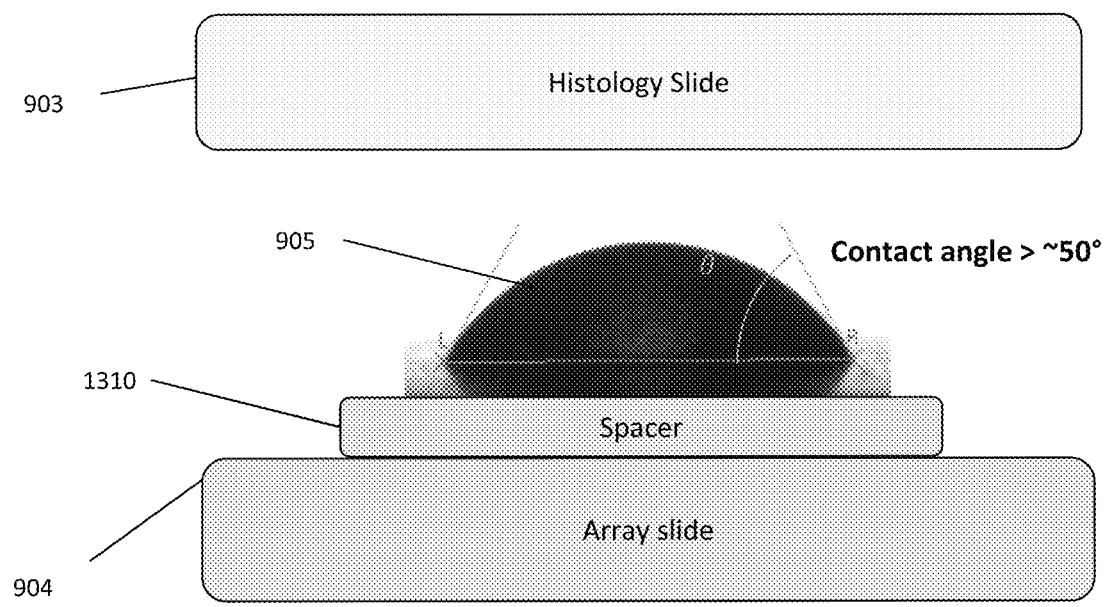
FIG. 43 shows an example contact angle of a drop of reagent medium placed on a spacer prior to sandwich closure.

In some aspects, the spacer material may be selected for promoting a desired contact angle of a drop of reagent medium placed on the spacer prior to sandwich closure. In some embodiments, the desired contact angle of the drop of reagent medium placed on the spacer is 40° or greater. In some embodiments, the desired contact angle of the drop of reagent medium placed on the spacer is 50° or greater. See, e.g., FIG. 43. Advantages of selecting the spacer material to promote a reagent drop contact angle of, e.g., 40° or greater or 50° or greater includes, but are not limited to: ensuring droplet confinement on the spacer prior to sandwich closure such that the reagent medium does not leak into the array area before sandwiching, and reducing the incidence of bubble formation/bubble trapping in a chamber formed from the spacer, the first substrate, and second substrate during sandwiching. Spacer materials that promote a contact angle of 50° or greater include, but are not limited to: silicone elastomer, graphite, and polyester.

In some aspects, the one or more spacers 1310 may be attached to the first substrate and/or the second substrate via an adhesive, a plasma treatment, and ultraviolet (UV) curing process, or the like. For example, the one or more spacers 1310 may include an adhesive or adhesive layer on one or more sides so that the one or more spacers 1310 may be attached to the first substrate and/or the second substrate.

Figure 28:
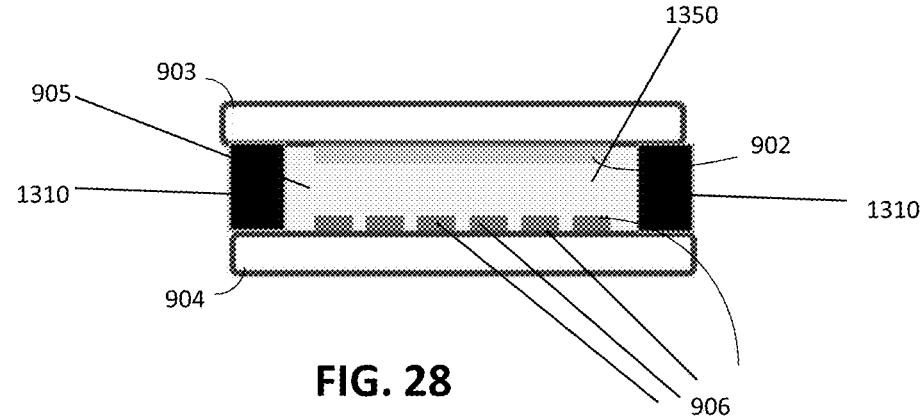
FIG. 28 shows an exemplary sandwich configuration where a first substrate, including a biological sample, and a second substrate are brought into proximity with one another in accordance with some example implementations.

FIG. 28 shows an exemplary sandwich configuration 2800 where a first substrate (e.g., pathology slide 903), including a biological sample 902 (e.g., a tissue section), and a second substrate (e.g., slide 904 including spatially barcoded capture probes 906) are brought into proximity with one another in accordance with some example implementations. As shown in FIG. 28 a liquid reagent drop (e.g., permeabilization solution 905) can be introduced on the second substrate in proximity to the capture probes 906 and in between the biological sample 902 and the second substrate (e.g., slide 904). The permeabilization solution 905 may release analytes that can be captured by the capture probes 906 of the array. As further shown, one or more spacers 1310 may be positioned between the first substrate (e.g., pathology slide 903) and the second substrate (e.g., slide 904). In some embodiments, the one or more spacers 1310 can include one or more spacing members that assist in maintaining the spacing and/or approximately parallel arrangement of the first and second substrates. The spacing members can be connected to either or both of the first and the second substrates. In some aspects, the terms "spacer" and "gasket" are used herein to describe spacing members that may assist in maintaining the spacing and/or approximately parallel arrangement of the first and second substrates and the terms may be used interchangeably.

In some embodiments, the one or more spacers 1310 may create a fully or partially enclosed chamber around the biological sample (e.g., tissue sample 902 or a region of interest) and/or the array 906. The fully enclosed one or more spacers 1310 can be configured to any shape. In some embodiments, the fully enclosed (e.g., encompassed) chamber created by the one or more spacers 1310 is one of a square or a rectangle. In some embodiments, one or more spacers 1310 conform to the shape of the biological sample 902. For example, the one or more spacers 1310 are shown herein to have an example shape, an example height, and maintain an example separation distance (e.g., 12.5 μm), although other values and shapes are possible and may depend on the liquid reagent, the biological sample 902, the capture probes 906, or the like.

Figure 29A:
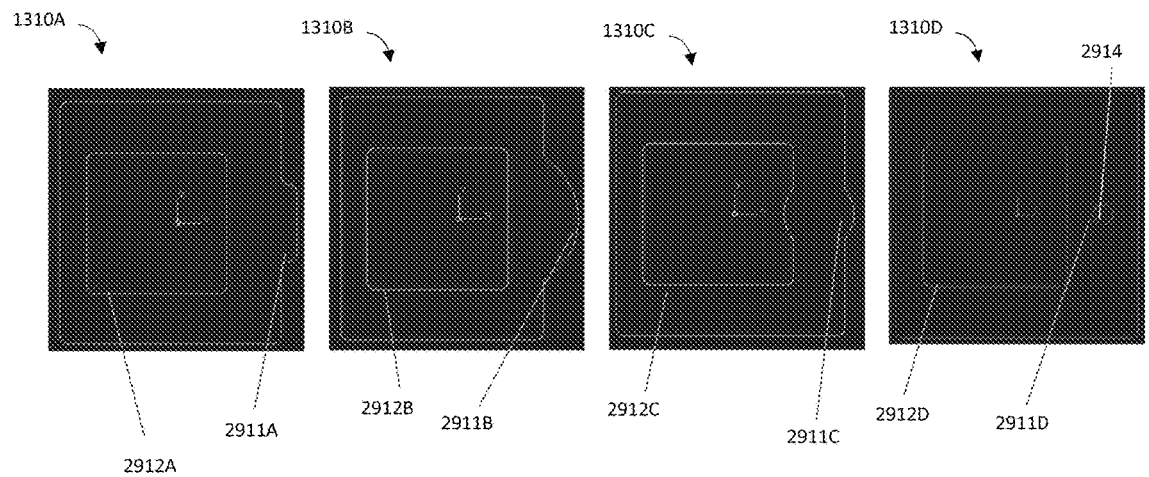
FIG. 29A depicts a top view of example spacer designs.

FIG. 29A depicts a top view of example spacer designs 1310A-D. As shown, the spacer designs 1310A-D include a fluid dispensing guide outlines 2911A-D and a central aperture outlines 2912A-D. As further shown, Spacer designs 1310A-D can have geometrical pattern/shape such as round cut-outs or features for user guidance (e.g., an area defined by the fluid dispensing guide outlines 2911A-D) when dispensing a fluid (e.g., drop of the permeabilization solution 905). For example, the spacer design 1310A shows a rectangular protrusion extending from a side (e.g., a right hand side) of the spacer design 1310A and defined by the fluid dispensing guide outline 2911A. The spacer design 1310B shows a rounded curve protrusion extending from side (e.g., a right hand side) of the spacer design 1310B. The rounded curve protrusion may be defined by the fluid dispensing guide outline 2911B. The spacer design 1310C shows a rounded curve protrusion extending from a side (e.g., a right hand side) of the spacer design 1310C. The rounded curve protrusion may be defined by the fluid dispensing guide outline 2911C. As compared to the spacer design 1310B, the spacer design 1310C may define a smaller area for the protrusion. The spacer design 1310D shows a circular cut-out on a right-hand side of the spacer design 1310D. The circular cut out may be defined by the fluid dispensing guide outline 2911D and may create an aperture 2914 in the spacer of spacer design 1310D. The aperture 2914 in the spacer design 1310D may beneficially keep a dispensed drop of fluid (e.g., permeabilization solution 905) pinned to a hydrophilic surface. While certain example geometries and shapes are shown in FIG. 29A for user guidance, other designs, shapes, geometries, etc. are possible.

Figure 29B:
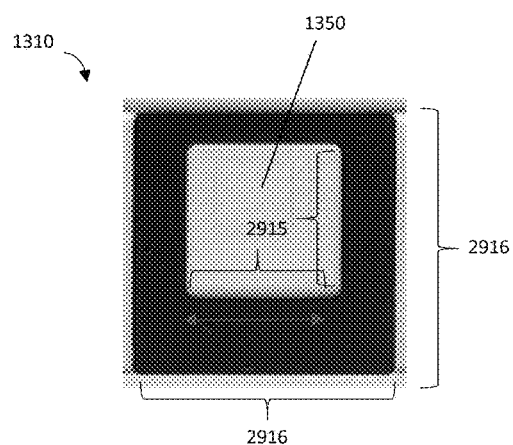
FIG. 29B depicts a top view of an example spacer.

FIG. 29B depicts a top view of an example spacer 1310. As shown, the example spacer 1310 has a square shape with a square central aperture defining the chamber 1350. As further shown, the central aperture is defined by dimension 2915 and the spacer 1310 is defined by dimension 2916. In some aspects, the dimension 2915 may include a size of approximately 13 mm and the dimension 1216 may include a size of approximately 25 mm. Although example values are given for the dimension 2915 and 2916, other values are possible and may be based on a size and/or shape of the first substrate and/or the second substrate. In some embodiments, the dimensions 2915 and 2916 are sized based on the size of an array area of a spatially barcoded array of capture probes on, e.g., the second substate. For example, the dimensions 2915 and 2916 can be sized such that the spacer surrounds the array area and optionally does not overlap the array area.

In some aspects, an instrument (e.g., the sample holder 1000, the sample holder 1200, or the like) may be configured to aid with user fluid dispensing guidance, e.g., by having a light illumination on a fluid dispensing position, marks, prints, machined patterns such as arrows pointing toward the fluid dispensing position on the spacer 1310. For example, a light may be positioned within or beneath an instrument substrate holder and may be configured to illuminate an area on a substrate or spacer as a visual guide indicating the fluid dispensing position.

Figure 29C:
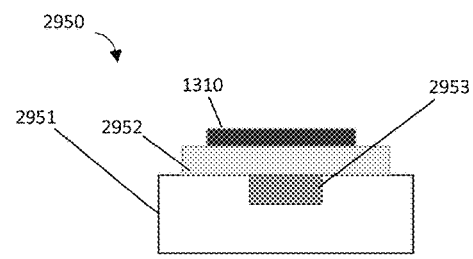
FIG. 29C depicts an example substrate configuration in accordance with some example implementations.

FIG. 29C depicts an example substrate configuration 2950 in accordance with some example implementations. As shown, the substrate configuration 2950 includes a substrate holder 2951 positioned inferior to a substrate 2952 and the spacer 1310 and a light source 2953 is disposed within or on a surface of the substrate holder 2951. The substrate 2952 is disposed between the substrate holder 2951 and the spacer 1310, with the spacer 1310 positioned superior to the substrate 2952 and the light source 2953 positioned inferior to the substrate 2952. The light source 2953 may include a light-emitting diode (LED) or other light source. As shown, the light source 2953 may be configured to emit a light upward (e.g., in a superior direction) toward the substrate 2952 and the spacer 1310. In the example of spacer design 1310D, the light may shine through the aperture 2914 and aid a user by providing a visual guide for dispensing the fluid within the aperture 2914. In some embodiments wherein the spacer does not have an aperture, the light from the light source 2953 (e.g., an LED) may pass through the spacer and provide a visual guide for dispensing the fluid at the illuminated position of the spacer. While the light source 2953 is shown in a particular position in the example substrate configuration 2950, the light source 2953 may be positioned in other locations of the instrument. For example, the light source 2953 may be positioned above or below the substrate 2952. Additionally, any instrument guide may be combined with visual marks on spacer 1310 to guide a user for proper fluid dispensing.

Figure 34:
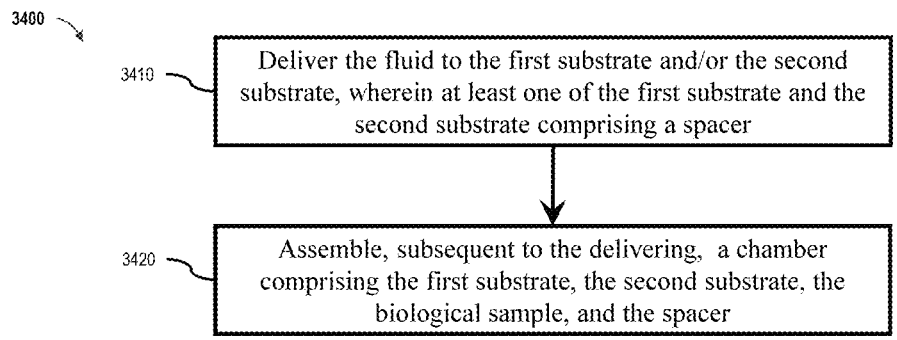
FIG. 34 illustrates a flowchart of a method for delivering a fluid to a biological sample, in accordance with some example implementations.

FIG. 34 illustrates a flowchart of a method 3400 for delivering a fluid to a biological sample, in accordance with some example implementations. In various implementations, the method 3400 (or at least a portion thereof) may be performed by one or more of the sample holder 1000, the sample holder 1200, a controller, a processor, other related apparatuses, and/or some portion thereof.

Method 3400 can start at operational block 3410 where the sample holder, for example, can deliver a fluid to a first substrate and/or a second substrate. At least one of the first substrate and the second substrate may include a spacer.

In some embodiments, the biological sample may be disposed on the first substrate and an array may be disposed on the second substrate. The fluid may include a permeabilization reagent or solution. The first substrate, the second substrate, or both may include a glass surface. The first substrate and the second substrate may be axially aligned or aligned in cross configuration. The spacer may include a virtual gasket. The virtual gasket may include a hydrophobic coating or solution. The spacer may include a polyester or silicon material. The spacer may include one or more apertures or no apertures. The spacer may include an air-permeable spacer portion configured to vent a bubble from the fluid. The spacer may be formed from a uniform thickness material. The spacer may include a beveled edge on one or more sides of the spacer. Delivering the fluid to the first substrate and/or the second substrate may include delivering the fluid to a region of the second substrate, the spacer comprising three sides partially surrounding the fluid. Delivering the fluid to the first substrate and/or the second substrate may include delivering the fluid to a region of the spacer, the region positioned outside an enclosed area of the second substrate, the enclosed area formed by the spacer. Delivering the fluid to the first substrate and/or the second substrate may include delivering the fluid to a region of the second substrate, the spacer comprising three sides partially surrounding the fluid. Delivering the fluid to the first substrate and/or the second substrate may include generating a vacuum to a region proximate to the first substrate and/or the second substrate. Delivering the fluid to the first substrate and/or the second substrate may include adjusting a humidity of the chamber. The second substrate may include a hydrophobic area positioned away from a region of interest, the hydrophobic area may be configured to remove bubbles in the fluid from the chamber, and the region of interest may include an area where the biological sample and the array overlap.

Method 3400 can proceed to operational block 3420 where the sample holder, for example, can assemble the chamber including the first substrate, the second substrate, the biological sample, and the spacer.

In some implementations, the spacer may be disposed between the first substrate and the second substrate. The spacer may be configured to maintain the fluid within the chamber and maintain a separation distance between the first substrate and the second substrate. The separation distance may include a distance of at least 2 µm. The spacer may be positioned to at least partially surround an area on the first substrate on which the biological sample is disposed. The spacer may be positioned to at least partially surround the array disposed on the second substrate. The area of the first substrate, the spacer, and the second substrate may at least partially enclose a volume that includes the biological sample. Assembling the chamber may include positioning, responsive to the delivering, the first substrate at an angle such that a dropped side of the first substrate contacts at least a portion of the fluid when the first substrate and the second substrate are within a threshold distance along an axis orthogonal to the second substrate, the dropped side urging the fluid toward the three sides partially surrounding the fluid. The chamber may include a hydrophobic pattern at least partially surrounding the fluid and positioned to at least partially surround the area on the first substrate and/or the array disposed on the second substrate. The method may further include applying the hydrophilic coating to the first substrate and/or the second substrate. The method may further include generating a vibration to the first substrate and/or the second substrate. The chamber may include a partially or fully sealed chamber.

Figure 14:
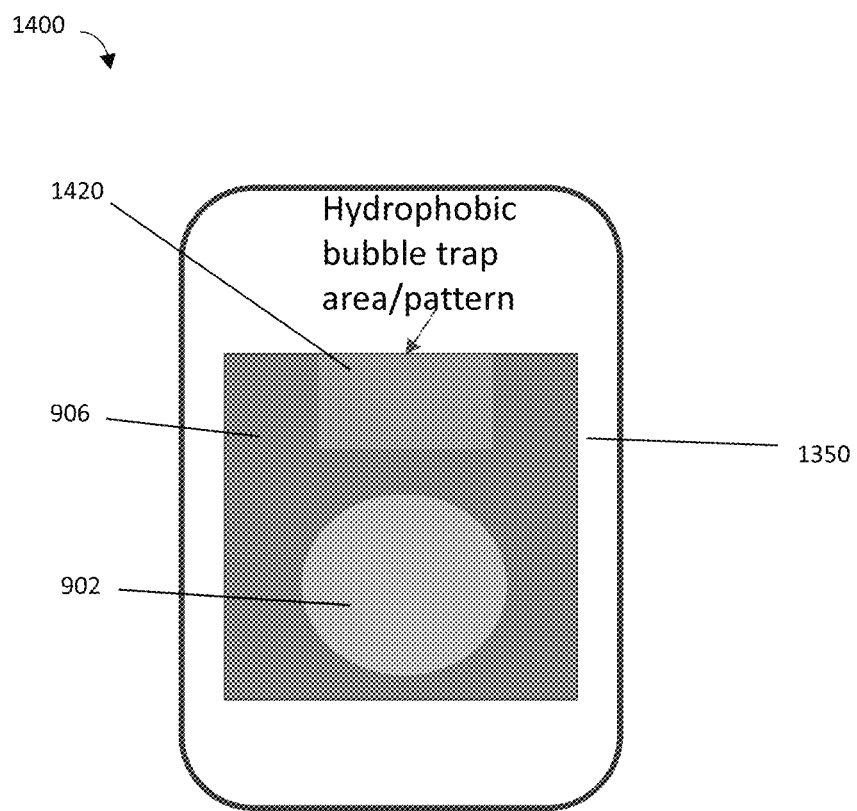
FIG. 14 depicts an example configuration for venting or removing bubbles from the chamber in accordance with some example implementations.

FIG. 14 depicts an example configuration 1400 for venting or removing bubbles from the chamber 1350 in accordance with some example implementations. FIG. 14 depicts a top view of the chamber 1350 where a square portion includes the capture probes 906, a circular portion includes the biological sample 902, and a rectangular portion includes a hydrophobic area 1420. The hydrophobic area 1420 may include a hydrophobic pattern that does not wet and is disposed in a portion of the chamber 1350 that is located away from an area of interest (e.g., an area where the biological sample 902 and the capture probes 906 overlap). The hydrophobic area 1420 may be configured to remove bubbles (e.g., bubbles 2015) from the chamber 1350 during the permeabilization step.

In some aspects, any combination of bubble venting or bubble removing features may be applied to the chamber, the first substrate, and/or the second substrate. For example, air permeable spacers (e.g., spacers 1310) may be configured to vent out trapped bubbles. Further, bubble venting holes disposed on the first substrate, the second substrate, and/or a spacer may be placed at strategic locations to vent bubbles. In some aspects, a sonication or vibration device may be configured to generate vibration on the first substrate and/or the second substrate during closing of the sandwich to reduce the chance of a bubble sticking to a surface of the first substrate or the second substrate. Additionally, it may be possible to increase a humidity of the chamber during sandwich closing to facilitate the filling process of the permeabilization solution or liquid reagent. Further, it may be possible to generate a vacuum in the chamber during closing to reduce or eliminate the chance of bubble trapping.

FIGS. 15A-15C show example configurations for that one or more spacers 1310 disposed on the first substrate (e.g., the pathology slide 903) and/or the second substrate (e.g., the slide 904) in accordance with some example implementations. While the slide 904 (e.g., the second substrate) is shown in FIGS. 15A-15C, the example spacer configurations may apply equally to the first substrate (e.g., the pathology slide 903) in accordance with example embodiments. In some aspects, the example spacer configurations of FIGS. 15A-15C may be combined with an angled closure workflow as described herein (e.g., workflow 1700 of FIGS. 17A-18B).

FIG. 15A is a top view of an example chamber 1350 having a partial enclosure with three sides of the one or more spacers 1310 closed. As shown, a drop of the permeabilization solution 905 is disposed along the open side of the chamber 1350 and on a surface of the slide 904. In some aspects, an angled closure of the first substrate (e.g., the pathology slide 903) contacting the drop 905 may urge the permeabilization solution toward the one or more spacers 1310 partially surrounding the drop 905. In some implementations, the three sides of the one or more spacers 1310 may at least partially surround capture probes 906 of the second substrate (e.g., slide 904) and/or the biological sample 902 of the first substrate (e.g., pathology slide 903). The permeabilization solution 905 may be positioned proximate to the capture probes 906 of the second substrate (e.g., slide 904) or any other region of the second substrate.

FIG. 15B depicts a top view of another example chamber 1350 having a full enclosure. As shown, the one or more spacers 1310 fully surround and enclose the chamber 1350. As further shown, the drop of the permeabilization solution 905 is positioned outside of the chamber 1350 on a surface of the slide 904. As described above, an angled closure workflow (e.g., workflow 1700) of the first substrate (e.g., the pathology slide 903) over the second substrate (e.g., slide 904) may result in a dropped side of the first substrate contacting the drop 905 and urging the permeabilization solution 905 toward and within the chamber 1350. In the example of FIG. 15B, the one or more spacers 1310 may at least partially surround capture probes 906 of the second substrate (e.g., slide 904) and/or the biological sample 902 of the first substrate (e.g., pathology slide 903).

FIG. 15C depicts a top view of another example chamber 1350 having a full enclosure. As shown, the one or more spacers 1310 fully surround and enclose the chamber 1350. As further shown, the drop of the permeabilization solution 905 is positioned outside of the chamber 1350 and on a surface of the one or more spacers 1310. As described herein, an angled closure workflow (e.g., workflow 1700) of the first substrate (e.g., the pathology slide 903) over the second substrate (e.g., slide 904) may result in a dropped side of the first substrate contacting the drop of the permeabilization solution 905 and urging the permeabilization solution 905 toward and within the chamber 1350. In the example of FIG. 15C, the one or more spacers 1310 may at least partially surround capture probes 906 of the second substrate (e.g., slide 904) and/or the biological sample 902 of the first substrate (e.g., pathology slide 903).

FIGS. 16A-16E depict example configurations of the one or more spacers 1310 combined with one or more hydrophobic areas 1420 in accordance with some example implementations. Any or all of the example configurations shown may be combined with an angled closure workflow (e.g., workflow 1700) for sandwiching the first substrate and the second substrate and for forming the chamber 1350.

FIG. 16A depicts a top view of an example chamber 1350. As shown, the chamber 1350 comprises three sides of the one or more spacers 1310 and a fourth side including the hydrophobic area 1420. As further shown, the drop of the permeabilization solution 905 is located on the slide 904 proximate to the hydrophobic area 1420. As described above, an angled closure workflow (e.g., workflow 1700) of the first substrate (e.g., the pathology slide 903) over the second substrate (e.g., slide 904) may result in a dropped side of the first substrate contacting the drop of the permeabilization solution 905 and urging the permeabilization solution 905 toward the opposite side and within the chamber 1350 having the three sides of the one or more spacers 1310.

FIG. 16B depicts a top view of another example chamber 1350. As shown, the chamber 1350 includes four spacers 1310 placed at the four corners of the chamber 1350 and the hydrophobic area 1420 comprising the sides of the chamber 1350. In the example of FIG. 16B, the spacers 1310 placed at the corners of the chamber 1350 may retain a minimum spacing between a first substrate (e.g., the pathology slide 903) and the second substrate (e.g., the slide 904) during sandwiching. The hydrophobic area 1420 of FIG. 16B may retain the permeabilization solution 905 within the chamber 1350 during the permeabilization step. During sandwiching, the permeabilization solution 905 may fill the volume of the chamber 1350.

In some aspects, any combination of the one or more spacers 1310, the hydrophobic area 1420, or the like may be implemented to achieve the chamber 1350 assembly and achieve flow and/or bubble suppression. In some embodiments, the one or more spacers 1310 and/or the hydrophobic area 1420 may be disposed on either the first substrate (e.g., the pathology slide 903) or the second substrate (e.g., the slide 904).

FIG. 16C depicts a top view of an example configuration for the one or more spacers 1310 on the second substrate (e.g., the slide 904). As shown, the one or more spacers 1310 surround the drop of permeabilization solution 905 on three sides of the chamber 1350.

FIG. 16D depicts a top view of the first substrate (e.g., the pathology slide 903) including the biological sample 902 and the hydrophobic area 1420.

FIG. 16E depicts a top view of the first substrate (e.g., the pathology slide 903 of FIG. 16D) sandwiched with the second substrate (e.g., the slide 904 of FIG. 16C). As shown, the combination of the one or more spacers 1310 of FIG. 16C and the hydrophobic area 1420 of FIG. 16D form the fully enclosed chamber 1350 of FIG. 16E.

I. Additional Fluid Delivery Methods and Kits

Provided herein are methods for delivering a fluid to a biological sample disposed on an area of a first substrate and an array disposed on a second substrate, including, assembling a partially sealed chamber comprising the first substrate, the second substrate, the biological sample, and a gasket, where a gasket is disposed between the first substrate and second substrate, and surrounds the area on the first substrate and/or the array disposed on the second substrate, where the area of the first substrate, the gasket, and the second substrate at least partially encloses a volume including the biological sample and delivering the fluid to the partially sealed chamber through one or more apertures of the gasket, thereby delivering the fluid to the array and the biological sample.

Also provided herein are methods for delivering a fluid to a biological sample disposed on an area of a first substrate and an array disposed on a second substrate, including, assembling a partially sealed chamber including the first substrate, the second substrate, the biological sample, and a gasket, where a gasket is disposed between the first substrate and second substrate, and surrounds the area on the first substrate and/or the array disposed on the second substrate, wherein the first substrate, the gasket, and the second substrate at least partially encloses a volume including the biological sample and delivering the fluid to the partially sealed chamber through one or more via-holes in the first substrate or one or more via-holes in the second substrate, thereby delivering the fluid to the array and the biological sample.

Also provided herein are methods for delivering a fluid to a biological sample disposed on an area of a first substrate and an array disposed on a second substrate, including, delivering a fluid to the area on the first substrate, where a virtual gasket surrounds the area on the first substrate and contains the fluid within the area and assembling the second substrate with the first substrate, thereby delivering the fluid to the array and the biological sample.

Also provided herein are methods for delivering a fluid to a biological sample disposed on an area of a first substrate and an array disposed on a second substrate, including, delivering a fluid to the area on the second substrate, where a virtual gasket surrounds the area on the second substrate and contains the fluid on the array and assembling the first substrate with the second substrate, thereby delivering the fluid to the array and the biological sample.

In some embodiments, the biological sample is disposed on a first substrate. In some embodiments an array (e.g., a substrate including capture probes) is on a second substrate. In some embodiments, the first substrate including the biological sample and the second substrate including the array (e.g., a spatial array) are brought in proximity to one another such that the first substrate and the second substrate are disposed proximally to each other.

As used herein, a "partially sealed chamber" is a chamber between a first substrate and a second substrate, where a gasket is disposed between the first substrate and the second substrate. The partially sealed chamber is accessible by one or more apertures in the gasket that allow for delivery of a fluid (e.g., a buffer, a permeabilization solution) to the partially sealed chamber. In some embodiments, a partially sealed chamber includes a gasket that completely surrounds (e.g., encompasses) the biological sample and/or the array, where the first the substrate or second substrate includes one or more via-holes for fluid delivery.

In some embodiments of any of the methods for delivery a fluid described herein, the first substrate, the second substrate, or both, can be any of the substrates described herein. In some embodiments, the first substrate is a glass surface. In some embodiments, the second substrate is a glass surface. In some embodiments, the first substrate and the second substrate are both glass surfaces. In some embodiments, the glass surface is a glass slide. In some embodiments, the first substrate, the second substrate, or both are glass slides.

In some embodiments, the first substrate and the second substrate can be axially aligned. For example, the second substrate can be placed on top of the first substrate, or vice versa, in substantially the same orientation as the first substrate. In some embodiments, the first substrate and the second substrate are aligned in a cross-configuration. For example, the second substrate can be placed on top of the first substrate, or vice versa, at approximately a 90° angle to the first substrate. In some embodiments, the second substrate can be placed on top of the first substrate, or vice versa, at about a 40°, about 45°, about 50°, about 55°, about 60°, about 65°, about 70°, about 75°, about 80°, or about 85° angle relative to the first substrate.

In some embodiments, a gasket is disposed on the first substrate prior to aligning the first substrate and second substrate (e.g., axially, cross-configuration). In some embodiments, the gasket surrounds (e.g., encompasses) the biological sample. In some embodiments, a gasket is disposed on the second substrate prior to aligning the first substrate and the second substrate. In some embodiments, the gasket surrounds (e.g., encompasses) the array on the substrate. In some embodiments, the gasket has no apertures (e.g., an opening). In some embodiments, the gasket has one aperture. In some embodiments, the gasket has two apertures or more. In some embodiments, the gasket includes one or more apertures and a hydrophobic coating is disposed at one or more apertures in the gasket to help prevent overflow after delivery of the fluid (e.g., a permeabilization solution).

In some embodiments, the gasket can be made of rubber, silicone, or a similar material to create a seal with the first substrate. In some embodiments, the gasket can be made of a material that is hydrophobic. Accordingly, different fluids, including a permeabilization solution, can be delivered to the various apertures of the gasket. In some embodiments, the engagement of the bottom of the gasket and top of the gasket in contact with the first substrate and the second substrate creates ample pressure to maintain a partially sealed chamber where fluid (e.g., a buffer, a permeabilization solution) is delivered. In some embodiments, the gasket is a virtual gasket.

As used herein, a "virtual gasket" is a hydrophobic coating that functions similar to a physical gasket such that fluid delivered within the virtual gasket is contained within the perimeter of the virtual gasket. In some embodiments, the hydrophobic coating helps localize the fluid (e.g., permeabilization solution) over the biological sample, including a region of interest. In some embodiments, the hydrophobic coating controls the volume between the first substrate and the second substrate after alignment (e.g., axially, cross-configuration) assembly. In some embodiments, the hydrophobic coating is applied with a stamp. For example, the hydrophobic coating can be applied with a stamp to the first substrate, the second substrate, or both. In some embodiments, the virtual gasket is drawn. In some embodiments, the virtual gasket is drawn with a wax or a paraffin-based crayon. In some embodiments, the virtual gasket is patterned. For example, the hydrophobic coating can be applied in a pattern to the first substrate, the second substrate, or both. In some embodiments, the hydrophobic coating encompasses the biological sample, the array, or both. In some embodiments, the hydrophobic coating is applied in a similar pattern to the physical gaskets described herein. For example, the hydrophobic coating can have no apertures, one aperture, or two or more apertures. In some embodiments, the hydrophobic coating is extended beyond the encompassed biological sample, array, or both to prevent capillary flow between the first substrate and the second substrate. In some embodiments, the hydrophobic coating is applied patterned in a grid. For example, the hydrophobic coating can be applied (e.g., applied by any of the methods described herein) to encompass one or more biological samples, one or more arrays (e.g., spatial array), or both on a substrate. In some embodiments, the hydrophobic coating can be applied to encompass 2, 3, 4, 5, 6, 7, 8, 9, 10, 11, 12, or more biological samples, one or more arrays (e.g., spatial array), or both on a substrate (e.g., a first substrate, a second substrate). In some embodiments, the hydrophobic coating is patterning is controlled dynamically via electro wetting.

In some embodiments, a spacer is used to separate the two substrates (e.g., the first substrate and the second substrate). Spacers can be placed adjacent to the biological sample and in between the first substrate and the second substrate. By doing so, spacers can create a chamber in which solutions (e.g., a buffer, a permeabilization solution) are contained throughout the permeabilization and analyte migration process. In some embodiments, more than one spacer is used. In some embodiments, a spacer has a height of about 10 μm, about 12.5 μm, about 15 μm, about 17.5 μm, about 20 μm, about 22.5 μm, or about 25 μm. In some embodiments, the height of each spacer has a height of about 50 μm, about 100 μm, about 200 μm, about 300 μm, about 400 μm, about 500 μm, about 600 μm, about 700 μm, about 800 μm, about 900 μm, or about 1000 μm. In some embodiments, the spacer creates a fully enclosed chamber around the biological sample (e.g., tissue sample or a region of interest) and/or the array. The fully enclosed spacer can be any shape. In some embodiments, the fully enclosed (e.g., encompassed) spacer is one of a square or a rectangle. In some embodiments, the spacer conforms to the shape of the biological sample.

In some embodiments, the spacer partially encloses the biological sample (e.g., tissue or region of interest) or the array. In some embodiments, the spacer surrounds the biological sample on one, two, or three sides. In some embodiments, the spacer partially encloses the biological sample, enclosing approximately at least about 60%, at least about 70%, at least about 80%, at least about 90%, or at least about 95% of the surrounding biological sample.

In some embodiments, no spacer is used in the system and/or methods disclosed herein. In some embodiments, a spacer functions as a gasket as disclosed herein.

In some embodiments of any of the fluid delivery methods described herein, the gasket (e.g., any of the gaskets described herein, a spacer), including a virtual gasket, can be applied to a region of interest in a biological sample. In some embodiments, two or more gaskets, including two or more virtual gaskets, can be applied to 2, 3, 4, or more regions of interest in the biological sample. In some embodiments, a fluid (e.g., a permeabilization solution) can be delivered to 2, 3, 4, or more regions of interest where a gasket, including a virtual gasket, substantially encompasses a region of interest in the biological sample.

In some embodiments the first substrate, the second substrate, or both can contain a via-hole. As used herein, a "via-hole" is an opening (e.g., an aperture, a through hole, a thru-hole), in the substrate as understood by a person of ordinary skill in the art. In some embodiments, the via-hole is in the first substrate. In some embodiments, the via-hole is in the second substrate. In some embodiments, a substrate (e.g., the first substrate, the second substrate) includes two or more via-holes.

In some embodiments, a fluid is delivered to one or more apertures of the gasket or a via-hole in a substrate. In some embodiments, the fluid is delivered to one or more apertures using capillary flow. In some embodiments, the fluid is delivered to a via-hole by capillary flow. In some embodiments, delivering the fluid (e.g., to an aperture, a via-hole) includes flowing the fluid through the aperture or the via-hole. In some embodiments, the fluid is delivered by a syringe. In some embodiments, the syringe interfaces with the aperture of the gasket (e.g., including a virtual gasket). In some embodiments, the syringe interfaces with a via-hole of the substrate. In some embodiments, a fluid (e.g., a buffer, a permeabilization solution) is delivered through a via-hole by a syringe. In some embodiments, delivering the fluid (e.g., to an aperture, a via-hole) includes injecting the fluid through the aperture (e.g., or a reservoir connected to an aperture) or a via-hole. In some embodiments of any of the delivery methods described herein, the syringe interfacing with a gasket or with a via-hole enables reproducible loading of the permeabilization solution. For example, the syringe can enable reproducible loading of volume and injection velocity of the fluid (e.g., permeabilization solution).

Figures 22A, 22B:
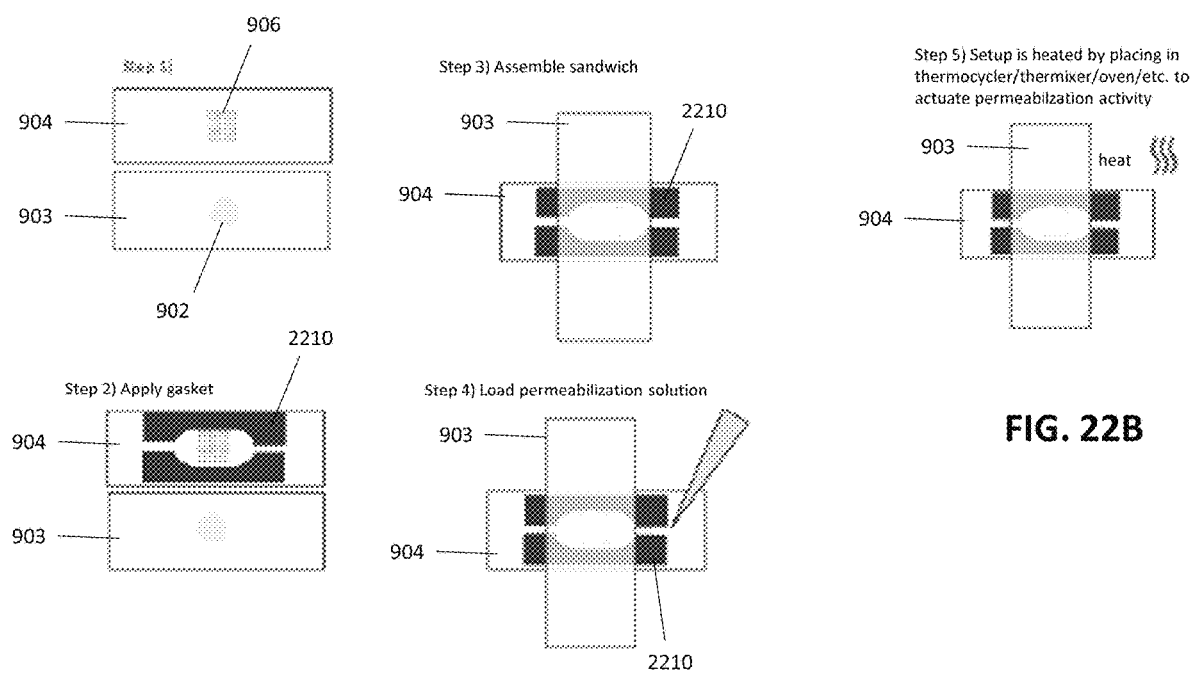
FIGS. 22A-B show an exemplary fluid delivery scheme.

For example, FIG. 22A shows an exemplary fluid delivery scheme. Step 1 shows the first substrate (e.g., slide 903) including a biological sample (e.g., sample 902) and an array 906 (e.g., a spatial array) on a second substrate (e.g., slide 904). Step 2 shows the application of a gasket 2210 that substantially encompasses the array 906 (e.g., partially encloses), however, the gasket 2210 can be applied to substantially encompass the biological sample 902 instead or additionally. The example gasket 2210 shown in FIG. 22A can include two apertures, but the gasket 2210 can also include zero, one, or two or more apertures. Step 3 shows an exemplary assembly to generate a partially sealed or fully sealed chamber. Step 3 also shows the first substrate and second substrate brought into proximity to form a sandwich assembly. In FIG. 22A, step 3 is shown with the first and second substrates (e.g., slides 903 and 904, respectively) aligned in a cross-configuration, however, the first substrate and the second substrate can also be aligned at various angles. For example, the first substrate and the second substrate can also be axially aligned (e.g., in a sandwich assembly as described herein). When the first substrate (e.g., slide 903), the second substrate (e.g., slide 904), and the gasket 2210 are assembled (e.g., in a sandwich assembly, any of the configurations described herein) a partially sealed or a fully sealed chamber may be formed where fluid can be delivered (e.g., through an aperture, through a via-hole, or the like) to the partially enclosed volume of the chamber. Step 4 shows delivery of a fluid (e.g., the permeabilization solution 905) to an aperture of the gasket via capillary flow. Alternatively, at Step 4 the fluid can be delivered at a cold temperature (e.g., about 5° C. to about 25° C.) and heated as shown in FIG. 22B. Step 5 (FIG. 22B) shows that heating of the first substrate (e.g., slide 903) and/or the second substrate (e.g., slide 904) configuration can actuate the rate of permeabilization of the biological sample 902.

Figure 23:
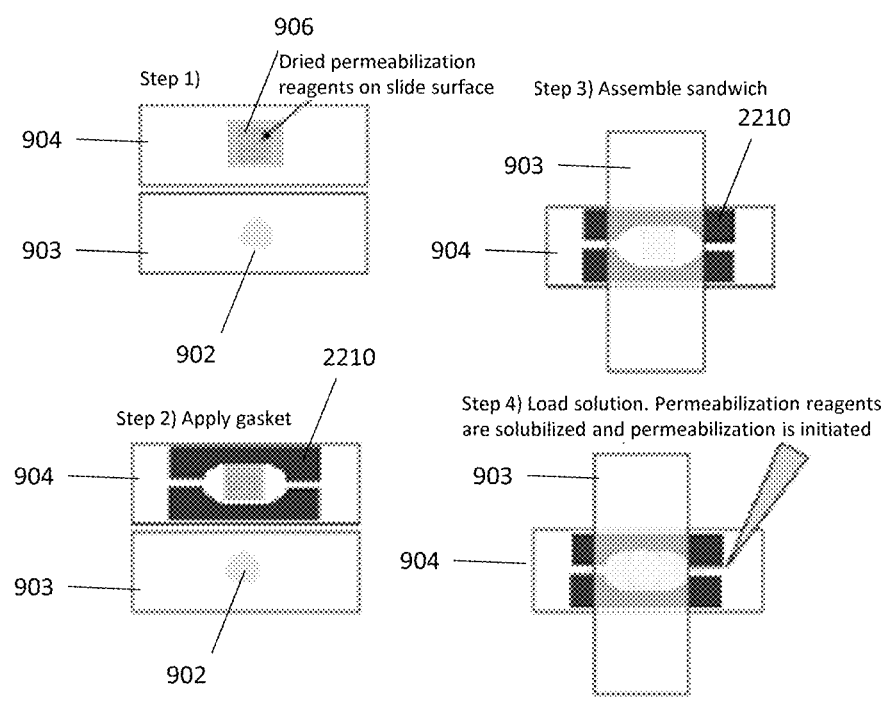
FIG. 23 shows an exemplary fluid delivery scheme.

FIG. 23 shows a similar exemplary fluid delivery scheme as FIGS. 22A-22B, but as shown in Step 1, dried permeabilization reagents can be disposed on the array 906. While not shown, dried permeabilization reagents can also be disposed on the biological sample 902. Similar to FIG. 22A, a gasket 2210 is applied (Step 2) and the first and second substrates (e.g., slides 903 and 904, respectively) are assembled (e.g., a sandwich assembly) (Step 3). As shown in Step 4, a fluid (e.g., a buffer) can be delivered via capillary action to solubilize the dried permeabilization reagents.

Figure 24:
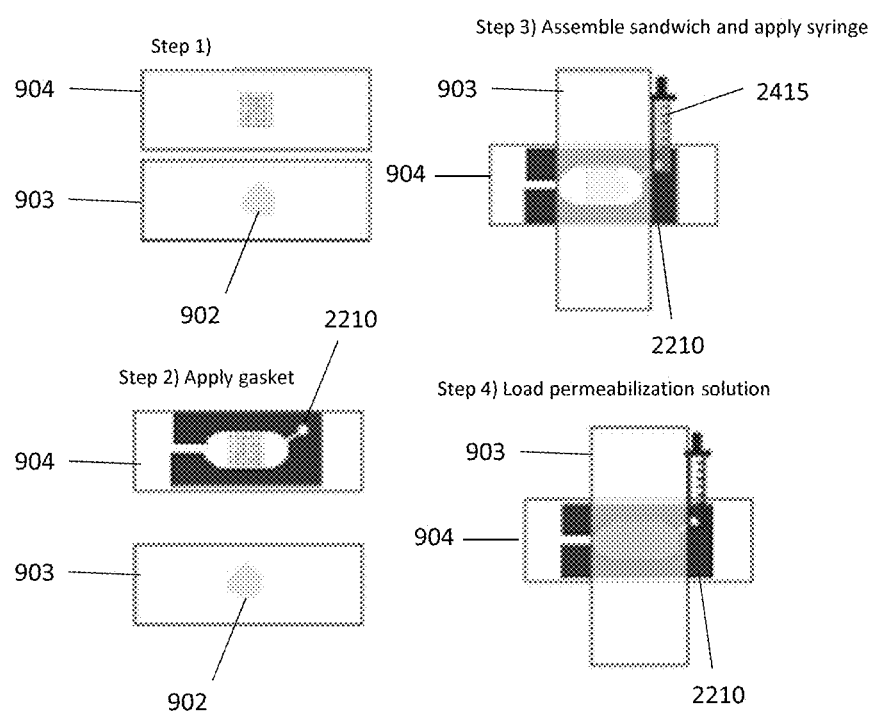
FIG. 24 shows an exemplary fluid delivery scheme.

FIG. 24 shows an exemplary fluid delivery scheme similar to FIGS. 22A-22B, but as shown in in Step 3, the fluid delivery mechanism can be a syringe 2415 that interfaces with the gasket 2210 (e.g., a reservoir in the gasket). At step 4, the fluid may be injected into the aperture by the syringe 2415.

Figures 25A, 25B:
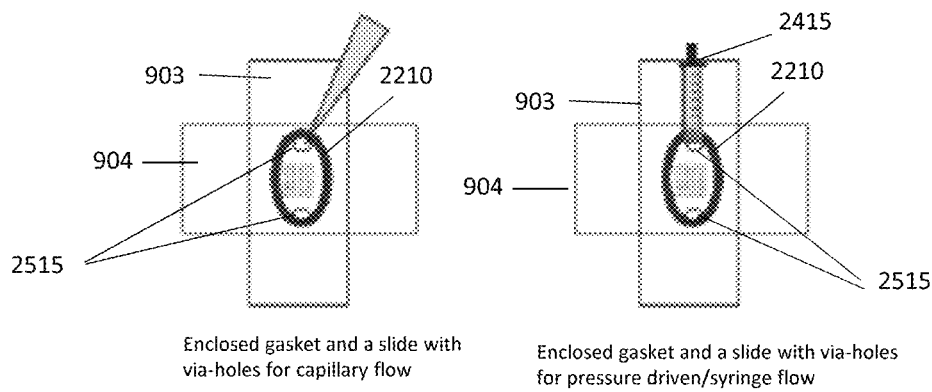
FIGS. 25A-B show an exemplary fluid delivery scheme.

FIG. 25A shows an exemplary fluid delivery scheme where a gasket 2210 includes no apertures and is disposed between the first substrate and the second substrate (e.g., slides 903 and 904, respectively) and where the first substrate and the second substrate are aligned in a cross-configuration. Similar to previous figures, while FIG. 25A shows a cross-configuration, the first substrate and the second substrate can be aligned at any angle, including axially (e.g., a sandwich assembly). As shown, the first substrate including the biological sample, can have one or more via-holes 2515 where a fluid, including a permeabilization solution (e.g., permeabilization solution 905) can be delivered (e.g., flowed through by capillary action, injected by a syringe, etc.) (FIG. 25A) or injected through a syringe 2415 (FIG. 25B). Alternatively or additionally, the second substrate can have one or more via-holes 2515 where a fluid, including a permeabilization solution, can be delivered as described herein.

FIG. 26 shows an exemplary fluid delivery scheme including the use of a virtual gasket, (e.g., a hydrophobic coating 2615 as indicated by the arrow). As shown in Step 1 a hydrophobic coating 2615 can be applied to surround (e.g., encompass) the array 906, however, the hydrophobic coating 2615 can also be applied to surround the biological sample 902, or both. The hydrophobic coating 2615 can be applied via a stamp or drawn, such as for example, with a wax crayon or a paraffin-based crayon. As shown in Step 2 a fluid (e.g., permeabilization solution) can be loaded on to the array 906 via capillary flow. While not shown, the fluid can be loaded via a syringe. Alternatively, dried permeabilization reagents can be disposed on the first substrate and/or the second substrate and can be solubilized by the delivered fluid. When the first substrate, the second substrate, and the virtual gasket (e.g., the hydrophobic coating 2615) are assembled (e.g., in a sandwich assembly, any of the configurations described herein) a partially sealed chamber can be formed where fluid can be delivered (e.g., through an aperture, through a via-hole) to the partially enclosed volume of the chamber.

Figure 27:
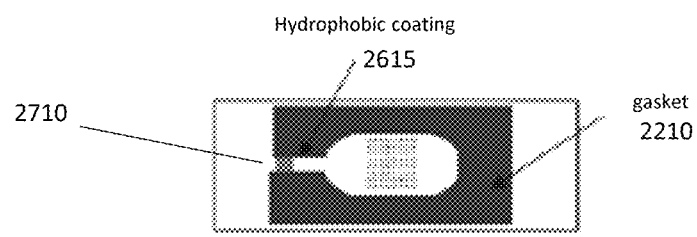
FIG. 27 shows an exemplary fluid delivery scheme.

FIG. 27 shows a configuration combining a hydrophobic coating 2615 and a gasket 2210. As shown in FIG. 27 the gasket can include an aperture 2710. A hydrophobic coating 2615 can be applied to the substrate not covered by the gasket (e.g., in the aperture 2710), to retain the delivered fluid (e.g., a buffer, the permeabilization solution 905). The hydrophobic coating 2615 can be applied to the aperture (e.g., one or more apertures) prior to delivering the fluid.

In some embodiments, the fluid includes permeabilization reagents (e.g., any of the permeabilization reagents described herein). In some embodiments, the rate of permeabilization of the biological sample is modulated by delivering the permeabilization reagents (e.g., a fluid containing permeabilization reagents) at various temperatures. For example, the fluid (e.g., a permeabilization solution, a buffer) can be delivered from about 5° C. to about 80° C., from about 10° C. to about 75° C., from about 15° to about 70° C., from about 20° C. to about 65° C., from about 25° C. to about 60° C., from about 30° C. to about 55° C., from about 35° C. to about 50°, and from about 40° C. to about 45° C. In some embodiments, the permeabilization solution can be about 5° C., about 6° C., about 7°, about 8° C., 9°, about 10° C., about 11° C., about 12° C., about 13° C., about 14° C., about 15° C., about 16° C., about 17° C., about 18° C., about 19° C., about 20° C., about 21° C., about 22° C., about 23°, 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., about 50° C., about 51° C., about 52° C., about 53° C., about 54° C., about 55° C., about 56° C., about 57° C., about 58° C., about 59° C., about 60° C., about 61° C., about 62° C., about 63° C., about 64° C., about 65° C., about 66° C., about 67° C., about 68° C., about 69° C., about 70° C., about 71° C., about 72° C., about 73° C., about 74° C., about 75° C., about 76° C., about 77° C., about 78° C., about 79° C., or about 80° C.

In some embodiments, the permeabilization reagents are dried permeabilization reagents. In some embodiments, the dried permeabilization reagents are disposed on a substrate (e.g., the first substrate, the second substrate). In some embodiments, delivering the fluid (e.g., by any of the fluid delivery methods described herein) solubilizes the dried permeabilization reagents. In some embodiments, solubilizing the permeabilization reagents results in permeabilization of the biological sample. In some embodiments, delivering the fluid to solubilize dried reagents is delivered via an aperture in a gasket. In some embodiments, delivering the fluid to solubilize dried reagents is delivered through a via-hole. In some embodiments, the fluid solubilizing dried reagents includes the use of a syringe. In some embodiments, the fluid solubilizing dried reagents includes the capillary flow.

In some embodiments, controlling the temperate of the first substrate, the second substrate, or both, modulates permeabilization of the biological sample. For example, the first substrate, the second substrate, or both, can be disposed in a substrate holder (e.g., any of the substrate holders described herein). In some embodiments, heating the first substrate, the second substrate, or both includes heating the permeabilization solution (e.g., the fluid comprising permeabilization reagents, solubilized dried permeabilization reagents) and modulating permeabilization of the biological sample. For example, permeabilization can be actuated by heating once the system has equilibrated (e.g., after fluid delivery) and there is no flow present in the system. In some embodiments, cooling the first substrate, the second substrate, or both includes cooling the permeabilization solution (e.g., the fluid including permeabilization reagents, solubilized dried permeabilization reagents) and modulating permeabilization of the biological sample.

In some embodiments, controlling the temperate of the first substrate, the second substrate, or both modulates permeabilization of the biological sample includes heating to about 25° C. to about 55° C., to about 30° C. to about 50° C., to about 35° C. to about 45° C., or to about 40° C. In some embodiments, controlling the temperate of the first substrate, the second substrate, or both modulates permeabilization of the biological sample includes heating to about 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., or 55° C.

In some embodiments, the biological sample is permeabilized for a period of time. For example, the biological sample can be permeabilized from about 1 minute to about 90 minutes or any length of time in between, from about 5 minutes to 85 minutes, from about 10 minutes to about 80 minutes, from about 15 minutes to about 75 minutes, from about 20 minutes to about 70 minutes, from about 25 minutes to about 65 minutes, from about 30 minutes to about 60 minutes, from about 35 minutes to about 55 minutes, from about 40 minutes to about 50 minutes, or about 45 minutes. In some embodiments, the biological sample is permeabilized for about 30 minutes at 40° C.

In some embodiments, delivering the permeabilization reagent includes delivering detergents (SDS, N-lauroylsarcosine, saponin, any other detergent described herein and combinations thereof), enzymes (e.g., Proteinase K, pepsin, collagenase, trypsin, nucleases, and any other enzyme described herein and combinations thereof), and buffers (e.g., TE, TAE, TBE, PBS, any other buffer described herein) sequentially in any order. In some embodiments, delivering the permeabilization reagents includes delivering detergents, enzymes, and buffers as a mixture. In some embodiments, permeabilization reagents are delivered two or more times to the partially sealed chamber. For example, permeabilization reagents can be delivered more than once to sufficiently permeabilize a biological sample. For example, permeabilization reagents can be delivered more than once to permeabilize a region of interest in a biological sample (e.g., at two or more regions of interest).

In some embodiments, adding a dye to the permeabilization reagent may help detect filling quality and visualize any bubbles present in the fluid. For example, the dye may be opaque at a certain wavelength and may be used in conjunction with a brightfield light and imaging at that certain wavelength to detect filling quality and any bubbles during sandwiching.

In some embodiments, the biological sample is imaged. In some embodiments, the biological sample is imaged on the first substrate prior to alignment with the second substrate. In some embodiments, the biological sample is a tissue section. In some embodiments, the biological sample is a fresh frozen biological sample. In some embodiments, the fresh frozen biological sample is a fresh frozen tissue section. In some embodiments, the biological sample is a fixed biological sample. In some embodiments, the fixed biological sample is a formalin-fixed paraffin-embedded biological sample.

In some embodiments, the array includes a plurality of features. In some embodiments, the array includes about 5,000 features. In some embodiments, a feature of the plurality of features is a bead. In some embodiments, a plurality of capture probes are attached to the bead. In some embodiments, the capture probe comprises (i) a capture domain; and (ii) a spatial barcode unique to the feature. In some embodiments, the capture domain of the capture probe includes a poly(T) sequence. In some embodiments, the capture probe includes one or more functional domains, a cleavage domain, a unique molecular identifier, and combinations thereof.

I. Angled Closure

In some instances, the contacting is achieved by arranging the first substrate and the second substrate in an angled sandwich assembly as described herein. For example, during the sandwiching of the two slides (e.g., the pathology slide 903 and the slide 904) it may be possible to provide an angled closure of the slides to suppress or eliminate bubble formation.

FIGS. 17A-17E depict an example workflow 1700 for an angled sandwich assembly in accordance with some example implementations. As shown in FIG. 17A, a slide 1712 (e.g., slide 904, second substrate 1012, second substrate 1212, or the like) may be positioned and placed on a base 1704 with a side of the slide 1712 supported by a spring 1715. The spring 1715 may extend from the base 1704 in a superior direction and may be configured to dispose the slide 1712 along a plane angled differently than the base 1704. The angle of the slide 1712 may be such that a drop (e.g., drop 1705) placed on the surface of the slide 1712 will not fall off the surface (e.g., due to gravity). The angle may be determined based on a gravitational force versus any surface force to move the drop away from and off the slide 1712. The base 1704 may include a holder plate of the second member 1210 of FIG. 12A, or the like.

FIG. 17B depicts a drop 1705 of liquid reagent (e.g., permeabilization solution 905) placed on the slide 1712. As shown, the drop 1705 is located on the side of the slide 1712 contacting the spring 1715 and is located in proximity and above (e.g., superior to) the spring 1715.

As shown in FIG. 17C, a second slide 1706 (e.g., the slide 904, the first substrate 1006, the first substrate 1206, or the like) may be positioned above (superior to) the slide 1712 and at an angle substantially parallel with the base 1704. For example, a first member (e.g., first member 1004, first member 1204, or the like) of a sample handling apparatus (e.g., the sample handling apparatus 1000, the sample handling apparatus 1200, or the like) may be configured to retain the slide 1706 at the angle substantially parallel to the base 1704.

As shown in FIG. 17D, slides 1706 may be brought into contact with slide 1712 slide 1712 such that a dropped side of the slide 1706 contacts the drop 1705 first. In some aspects, the drop side of the slide 1706 may urge the drop 1705 toward the opposite side of the slide 1706. In some aspects, slide 1706 may be lowered toward the slide 1712 to accomplish the contacting of the dropped side of the slide 1706 with the drop 1705. In some aspects, the slide 1712 may be moved upward toward the slide 1706 to accomplish the contacting of the dropped side of the slide 1706 with the drop 1705.

FIG. 17E depicts a full sandwich closure of the slide 1706 and the slide 1712 with the drop 1705 positioned between the two sides. In some aspects and as shown, as the slide 1706 is lowered onto the drop 1705 and toward the slide 1712 (or as the slide 1712 is raised up toward the slide 1706), the spring 1715 may compress and the slide 1712 may lower to the base 1704 and become substantially parallel with the slide 1706.

Figures 18A, 18B:
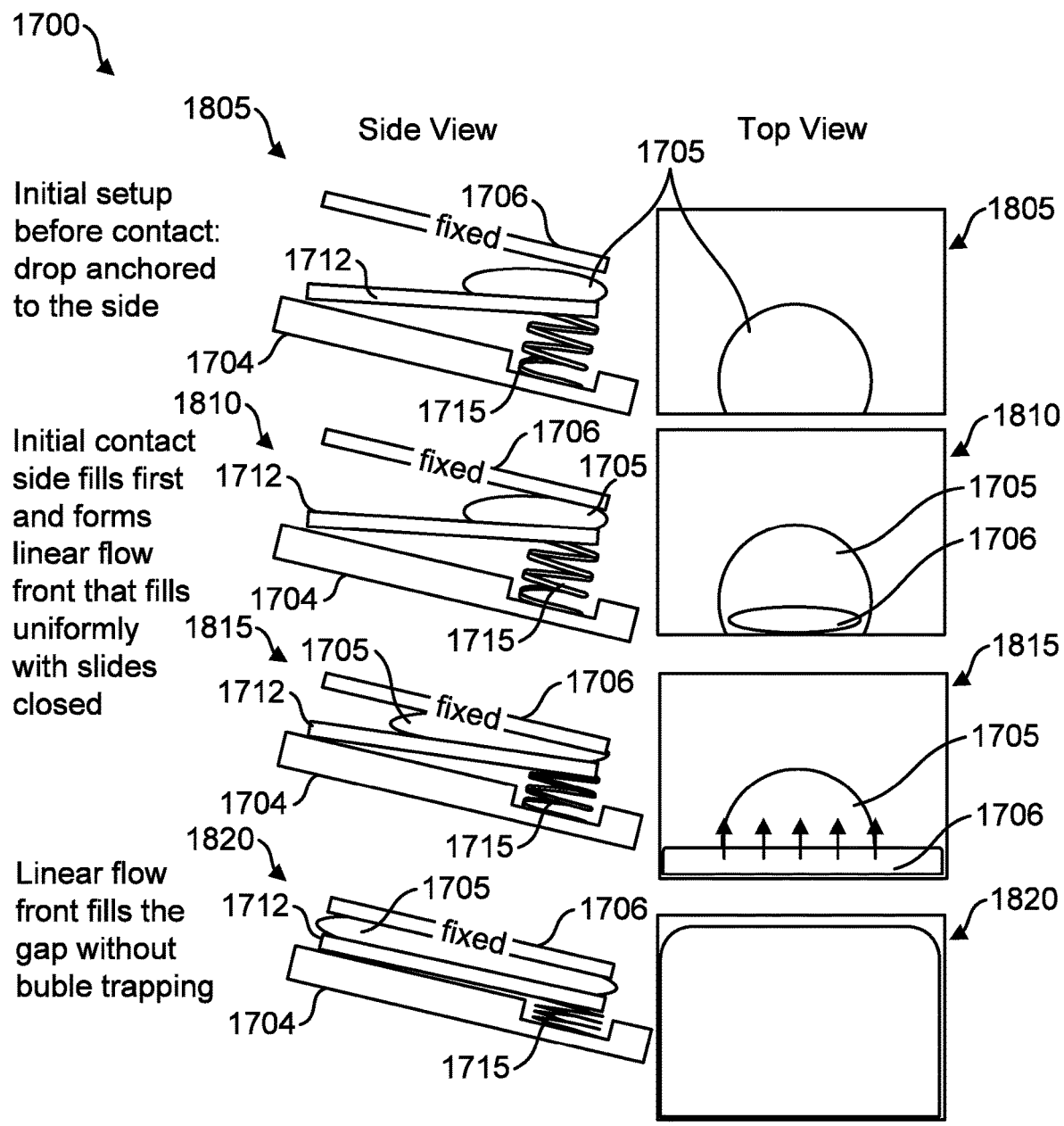
FIG. 18A is a side view of the angled closure workflow in accordance with some example implementations.
FIG. 18B is a top view of the angled closure workflow in accordance with some example implementations.

FIG. 18A is a side view of the angled closure workflow 1700 in accordance with some example implementations. FIG. 18B is a top view of the angled closure workflow 1700 in accordance with some example implementations. As shown at step 1805 and in accordance with FIGS. 17C-D, the drop 1705 is positioned to the side of the slide 1712 contacting the spring 1715.

At step 1810, the drop side of the angled slide 1706 contacts the drop 1705 first. The contact of the slide 1706 with the drop 1705 may form a linear or low curvature flow front that fills uniformly with the slides closed.\

At step 1815, the slide 1706 is further lowered toward the slide 1712 (or the slide 1712 is raised up toward the slide 1706) and the dropped side of the slide 1706 may contact and may urge the liquid reagent toward the side opposite the dropped side and creating a linear or low curvature flow front that may prevent or reduce bubble trapping between the slides. As further shown, the spring 1715 may begin to compress as the slide 1706 is lowered.

At step 1820, the drop 1705 of liquid reagent fills the gap (e.g., the gap 907) between the slide 1706 and the slide 1712. The linear flow front of the liquid reagent may form by squeezing the drop 1705 volume along the contact side of the slide 1712 and/or the slide 1706. Additionally, capillary flow may also contribute to filling the gap area. As further shown in step 1820, the spring 1715 may be fully compressed such that the slide 1706, the slide 1712, and the base 1704 may be substantially parallel to each other.

Figure 19A:
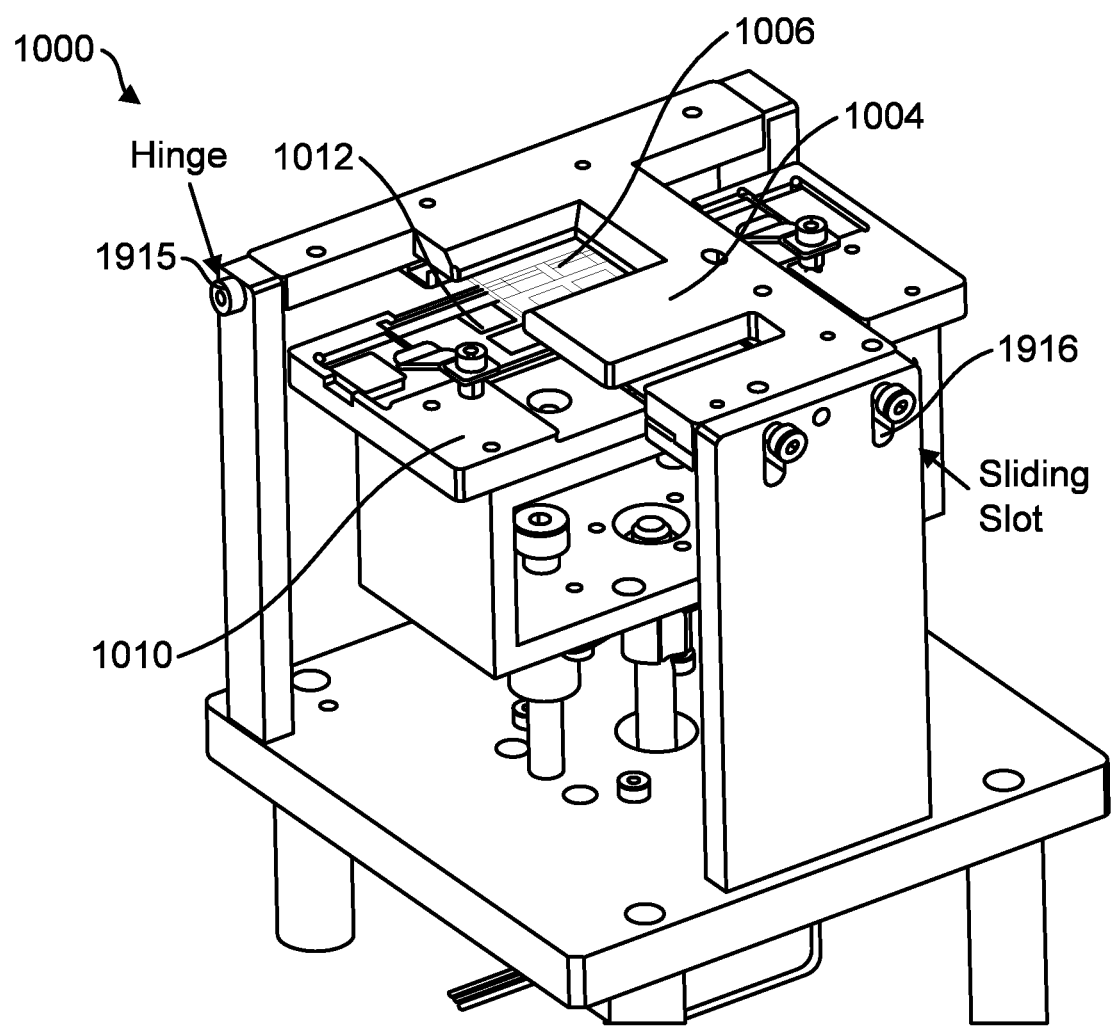
FIG. 19A depicts the sample handling apparatus including a hinge and a sliding slot coupled to the first member in accordance with some example implementations.

In some aspects, the angled closure of FIGS. 17-18 may be accomplished using a variety of hardware components. For example, FIG. 19A depicts the sample handling apparatus 1000 including a hinge 1915 and a sliding slot 1916 coupled to the first member 1004 in accordance with some example implementations. The hinge 1915 and/or the sliding slot 1916 may be configured to position the first member 1004 and/or the first substrate 1006 at an angle relative to the second member 1010 and/or the second substrate 1012. This angle can be as small as 0 degree.

Figure 19B:
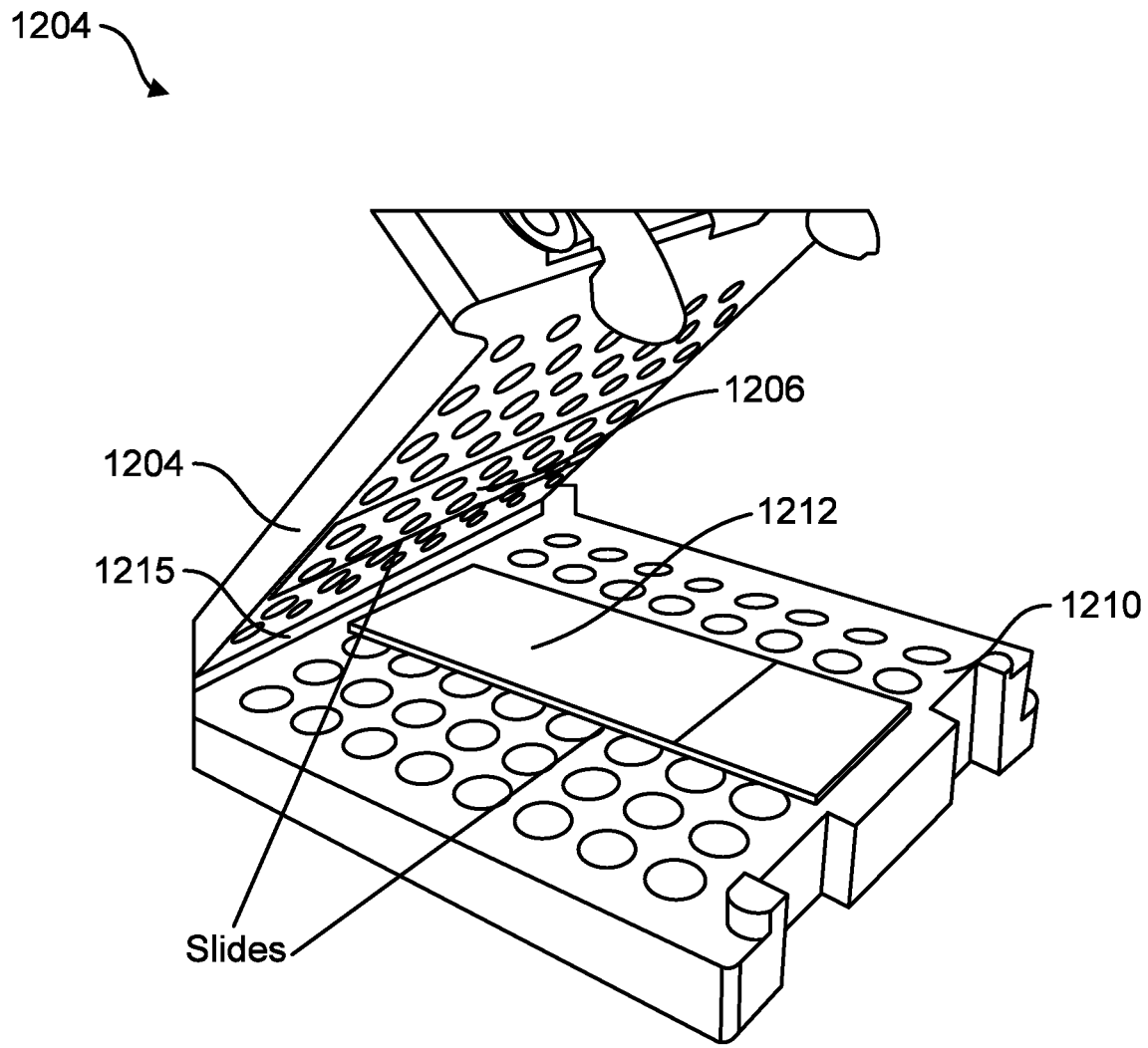
FIG. 19B depicts the sample handling apparatus in an open configuration with a first substrate coupled to the first member and the second member retaining the second substrate in accordance with some example implementations.

FIG. 19B depicts a sample handling apparatus 1200 in an open configuration with a first substrate 1206 coupled to the first member 1204 and the second member 1210 retaining the second substrate 1212 in accordance with some example implementations. In some aspects, closing the first member 1204 over the second member 1210 via the hinge 1915 may provide the angled closure described herein in at least FIGS. 17-18 and the corresponding description.

FIGS. 20A-20E show an example workflow 2000 for an angled sandwich assembly in accordance with some example implementations. As shown in FIG. 20A, the base 1704 may be positioned tilted at an angle. The slide 1712 may be disposed flat on the base 1704 and at the same, or substantially the same, angle. The angle may be determined such that a drop (e.g., drop 1705) placed on the surface of the slide 1712 will not fall off the surface (e.g., due to gravity). The angle may be determined by a gravitational force versus any surface force to move the drop away from and off the slide 1712.

FIG. 20B depicts the slide 1706 and the slide 1712 being sandwich together as the slide 1706 and the slide 1712 move toward each other and the slide 1706 contacts the drop 1705. In some aspects, the slides 1706 and 1712 may be parallel or at an angle relative to each other during the sandwiching. In some embodiments the angle of the slides may be achieved via a sample handling apparatus (e.g., the sample handling apparatus 1000, the sample handling apparatus 1200, or the like).

FIG. 20C depicts one or more air bubbles 2015 trapped within the drop 1705 during the sandwiching of the slides 1706 and 1712.

As shown in FIG. 20D, the one or more air bubbles 2015 may be less dense than the liquid reagent drop 1705 and the one or more air bubbles 2015 may migrate up in a superior direction due to buoyancy. In some aspects, as the one or more air bubbles 2015 may reach the top (e.g., uppermost part of the drop 1705), the bubbles may release or otherwise be removed from the drop 1705.

FIG. 20E depicts the base 1704, the slide 1706, and the slide 1712 being straightened along an axis and the one or more bubbles 2015 removed from the drop 1705 or removed from a region of interest between the slides 1706 and 1712.

In some aspects, the angled closure of FIGS. 17-18 and 20 may occur in response to detecting a bubble (e.g., bubble 2015) within the drop 1705. Additionally or alternatively, the angled closures described herein may occur during each sandwiching of the slides (e.g., the slides 1706 and 1712). A sensor may be configured to detect a bubble in the liquid reagent drop 1705 responsive to a slide (e.g., the slide 1706) or a tissue sample (e.g., tissue sample 902) contacting at least a portion of the drop 1705.

In some embodiments, adding a dye to the permeabilization reagent may help detect filling quality and visualize any bubbles present in the fluid. For example, the dye may be opaque at a certain wavelength and may be used in conjunction with a brightfield light and imaging at that certain wavelength to detect filling quality and any bubbles during sandwiching.

Figures 21A, 21B, 21C:
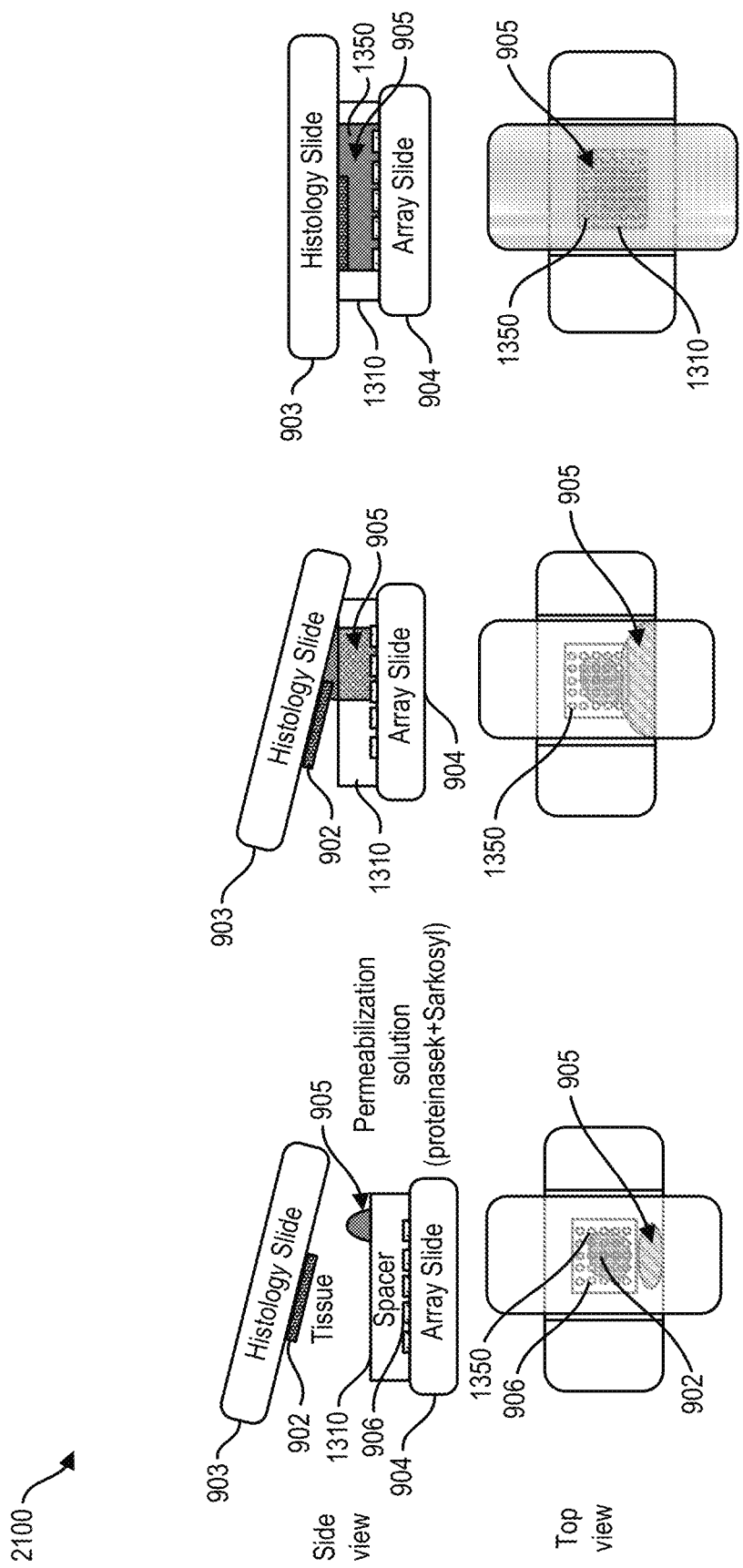
FIGS. 21A-21C depict a side view and a top view of an angled closure workflow for sandwiching a first substrate having a tissue sample and a second substrate in accordance with some example implementations.

FIGS. 21A-21C depict a side view and a top view of an angled closure workflow 2100 for sandwiching a first substrate (e.g., pathology slide 903) having a tissue sample 902 and a second substrate (e.g., slide 904 having capture probes 906) in accordance with some example implementations.

FIG. 21A depicts the first substrate (e.g., the pathology slide 903 including sample 902) angled over (superior to) the second substrate (e.g., slide 904). As shown, a drop of the permeabilization solution 905 is located on top of the spacer 1310 toward the right-hand side of the side view in FIG. 21A.

FIG. 21B shows that as the first substrate lowers, or as the second substrate rises, the dropped side of the first substrate (e.g., a side of the slide 903 angled inferior to the opposite side) may contact the drop of the permeabilization solution 905. The dropped side of the first substrate may urge the permeabilization solution 905 toward the opposite direction. For example, in the side view of FIG. 21B the permeabilization solution 905 may be urged from right to left as the sandwich is formed.

FIG. 21C depicts a full closure of the sandwich between the first substrate and the second substrate with the spacer 1310 contacting both the first substrate and the second substrate and maintaining a separation distance between the two. As shown in the top view of FIGS. 21B-21C, the spacer 1310 fully encloses and surrounds the tissue sample 902 and the capture probes 906, and the spacer 1310 forms the sides of chamber 1350 which holds a volume of the permeabilization solution 905. In some aspects, excess permeabilization solution 905 that exceeds a volume of the chamber 1350, may be dispersed outside of the chamber 1350.

In some aspects, the alignment of the tissue sample 902 with the capture probes 906 shown in FIGS. 21A-21C may be performed by an alignment mechanism of a sample handling apparatus (e.g., sample handling apparatus 1000, sample handling apparatus 1200, or the like).

In some aspects, an angled closure (e.g., the angled closure of FIGS. 17-18 and 20) may be combined with any of the fluid delivery methods described herein.

Kits

Also provided herein are kits including a first substrate including a coating (e.g., any of the coatings described herein) for adhering a biological sample, a second substrate comprising an array, and a spacer. In some kits, the spacer is disposed on the first substrate and/or the second substrate. In some kits, the spacer at least partially surrounds the biological sample and/or the array. In some kits, the spacer may be disposed between the first substrate and second substrate and configured to maintain a fluid within a chamber comprising the first substrate, the second substrate, the biological sample, and the spacer. The spacer may be further configured to maintain a separation distance between the first substrate and the second substrate. In some kits, the kit includes a paraffin-wax crayon. In some kits, the kit includes a hydrophobic coating stamp. In some kits, the kit includes a reverse transcriptase and a nuclease.

In some kits, the kit includes a second substrate including an array. The second substrate further includes a spacer surrounding the array. In some kits, the kit includes a first substrate including a biological sample. The first substrate further includes a spacer surrounding the biological sample. In some kits, the kit includes a spacer configured to be disposed between a first substrate and a second substrate. The kit further includes the first substrate and/or the second substrate.

The kits may also include instructions for assembling a chamber including the first substrate, the second substrate, the spacer, the biological sample, and the array. The kits may also include instructions for aligning the first substrate and/or the second substrate in a sample holder. The kits may also include instructions for performing any of the methods described herein.

I. Additional Sample and Array Alignment Devices and Methods

This disclosure further describes devices for holding or supporting substrates. In particular, the devices described include a first and second members that receive a first and second substrate, respectively. In some embodiments, the devices of the disclosure can be used for sandwiching the first and second substrates together for spatial transcriptomics applications. In some embodiments, the first substrate can support a sample (e.g., a biological substrate) on its surface. In some embodiments, the second substrate can include a plurality of barcoded probes and/or permeabilization reagents.

The devices for holding or supporting substrates described further include an alignment mechanism that is connected to at least one of the members and aligns the first and second members. Thus, the devices of the disclosure can advantageously align (e.g., along an XY axis) the first substrate and the second substrate and any samples, barcoded probes, or permeabilization reagents that may be on the surface of the first and second substrates. That is, the devices of the disclosure can facilitate analysis of a sample (e.g., a biological sample) by bringing the first and second substrates into contact with each other in an aligned manner.

In some instances, a sample holder is provided. In some instances, the sample holder includes a first member that includes a first retaining mechanism that retains a substrate with the sample. In some instances, the sample holder also includes a second member that includes a second retaining mechanism that retains a second substrate with a feature array. An alignment mechanism is connected to at least one of first and second members or to both first and second members. During an alignment and contacting procedure, an alignment mechanism functions to align the first and second members, thereby ensuring that sample and feature array are also aligned and brought into contact to facilitate analysis of sample.

In some embodiments, the alignment mechanism can be implemented as a rotating actuator connected to the first and second members. One example of such a rotating actuator is a hinge. In some instances, once a substrate-mounted sample is positioned in the first member and a substrate-mounted feature array is positioned in the second member, rotation of one of the members about the hinge axis aligns members and, and also aligns sample and feature array. The members can be rotated about the hinge axis until the sample and feature array are aligned and in contact. In some instances, the rotating actuator is implemented as a folding member. The folding member can be formed from a variety of materials, including compliant materials such as rubber and vinyl, metals and metal alloys, and plastics.

In certain embodiments, the rotating actuator can include at least one arm. In some instances, the rotating actuator can include multiple arms (e.g., 2 or more, 3 or more, 4 or more, or even more). In some instances, the sample holder is implemented as a unitary (i.e., one-piece) device. In some instances, the sample holder can also be implemented as a two-piece device, with first and second members being separate but reproducibly connectable via the alignment mechanism. When the first and second members are brought into proximity, connectors engage with receivers, aligning first and second members, and also aligning sample with the feature array. It should be noted that while connectors are positioned on the second member and receivers are positioned on the first member, the reverse could also be true. Moreover, first and second members could each include spacers 1310, have one or more connectors, and have one or more receivers.

The first retaining mechanism can be implemented in various ways. In some embodiments, the first retaining mechanism can correspond to a recess dimensioned to receive the first substrate. Further, a gasket can optionally be positioned within the recess to maintain an interference fit between the edges of the recess and first substrate. In certain embodiments, the first retaining mechanism can correspond to one or more members positioned to apply a force to the first substrate, in particular, to maintain contact between first substrate and first member. Examples of such members include, but are not limited to, clips, screws and other threaded retaining fasteners, and members that snap-fasten or otherwise engage with first member. The members can apply a force to the sample bearing surface of first substrate and/or to one or more lateral surfaces first substrate.

In general, the second retaining mechanism can correspond to any of the different types of retaining mechanisms discussed above in connection with first retaining mechanism. First and second retaining mechanisms can be different or the same.

In some embodiments, the first member includes a first aperture. The first aperture can be positioned, for example, so that when the first substrate is retained in first member, the first aperture is aligned with a sample region (e.g., a region where sample is typically located, or which is designated for placement of sample) on first substrate. Aperture can be positioned so that sample can be viewed from the back surface of first member (i.e., the surface opposite to the surface that supports first substrate) through first aperture, and one or more images of sample can be obtained through first aperture.

As described above, a reagent medium can be positioned on a first or second substrate. More generally, however, the first or second substrate may further comprise a reagent medium placed thereon. In certain embodiments, the reagent medium includes a permeabilization reagent (e.g., a solid, liquid, gel, or dried permeabilization reagent). In some embodiments, the reagent medium includes one or more additional components. For example, the additional components can include a hydrogel compound or layer with an embedded permeabilization reagent.

In some embodiments, the second member includes at least one aperture. More generally, the second member can include one or more (e.g., 2 or more, 3 or more, 4 or more, 5 or more, 6 or more, 8 or more, 10 or more, 15 or more, 20 or more, 30 or more, 40 or more, 50 or more, or even more) second apertures. In certain embodiments, the second aperture is aligned with at least a portion of the sample region on substrate when the first and second members and are aligned. A second aperture can used for various purposes. In some embodiments, for example, the feature array and/or the sample can be viewed or imaged through second aperture. Viewing/imaging can be used to adjust the relative positions of the feature array and the sample to improve alignment, for example.

In certain embodiments, one or more bounding surfaces of the second aperture and a back surface of the second substrate (i.e., a surface of the second substrate that is opposite to the surface of the second substrate that faces the sample and that supports feature array) cooperate to form a reagent well. A reagent solution (e.g., comprising a permeabilization reagent) added to the reagent well is contained by the bounding surfaces of the second aperture. If the second substrate is formed from a permeable or semi-permeable material, the reagent solution can permeate (e.g., by diffusion) through the back surface of the second substrate and contact the sample.

In some embodiments, the sample holder includes a first adjustment mechanism connected to the first member. The first adjustment mechanism translates the first substrate in at least one direction parallel to the surface of the first substrate that supports the sample. In some embodiments, the first adjustment mechanism translates the first substrate in two directions parallel to the surface of the first substrate.

The first adjustment mechanism can be implemented in various ways. In some embodiments, for example, the first adjustment mechanism includes one or more thumbscrews or linear actuators that can be used to translate the first substrate.

In addition to aligning the first and second members, the alignment mechanism is also configured to maintain a separation between the first and second substrates (and the first and second members) when the substrates (and members) are aligned. For example, the separation can be maintained such that at least a portion of the sample contacts the reagent medium (e.g., the feature array of the reagent medium).

In certain embodiments, the alignment mechanism maintains the first and second substrates in an approximately parallel relationship when the substrates (and the first and second members) are aligned. An included angle between the first and second substrates in such circumstances can be 2 degrees or less (e.g., 1 degree or less, 0.5 degrees or less, 0.25 degrees or less).

In some embodiments, the sample holder can include one or more spacing members that assist in maintaining the spacing and/or approximately parallel arrangement of the first and second substrates. Spacing members can be connected to either or both of the first and second members.

In certain embodiments, the sample holder includes a second adjustment mechanism. The second adjustment mechanism adjusts a distance of the separation between the first and second substrates (i.e., in a direction orthogonal to the surface of the first substrate that supports the sample). In certain embodiments, the adjustment mechanism is connected to both members.

The second adjustment mechanism can be implemented in various ways. In some embodiments, the second adjustment mechanism includes one or more thumbscrews or adjustable pins or posts. In certain embodiments, the second adjustment mechanism includes one or more linear actuators. In some embodiments, the second adjustment mechanism includes a swellable or expandable membrane, gasket, or layer positioned between the first and second members.

As a subsequent step in an analytical workflow, after the sample and the feature array have been brought into contact by the sample holder, the sample holder can be introduced into a thermocycler to promote capture of analytes from the sample by the feature array. The sample holder can be inserted directly into a suitable thermocycler for this purpose. Alternatively, in some embodiments, the sample holder can be coupled to a thermocycler adapter and the coupled holder and adapter inserted into a thermocycler. Suitable thermocycler adapters for use with the sample holder are described, for example, in U.S. Provisional Patent Application No. 62/839,575, filed on Apr. 26, 2019, the entire contents of which are incorporated herein by reference.

The sample holder is compatible with a variety of different schemes for contacting the sample with a permeabilization reagent to promote analyte capture. In some embodiments, a permeabilization reagent solution is deposited directly on the second substrate (e.g., forming a reagent medium that includes the permeabilization reagent and the feature array), and/or directly on the first substrate, and then the sample is contacted to the feature array.

In certain embodiments a dried permeabilization reagent is applied or formed as a layer on the first substrate or the second substrate or both prior to contacting the sample and the feature array. For example, a reagent can be deposited in solution on the first substrate or the second substrate or both and then dried. Drying methods include, but are not limited to spin coating a thin solution of the reagent and then evaporating a solvent included in the reagent or the reagent itself. Alternatively, in other embodiments, the reagent can be applied in dried form directly onto the first substrate or the second substrate or both. In some embodiments, the coating process can be done in advance of the analytical workflow and the first substrate and the second substrate can be stored pre-coated. Alternatively, the coating process can be done as part of the analytical workflow. In some embodiments, the reagent is a permeabilization reagent. In some embodiments, the reagent is a permeabilization enzyme, a buffer, a detergent, or any combination thereof. In some embodiments, the permeabilization enzyme is pepsin. In some embodiments, the reagent is a dried reagent (e.g., a reagent free from moisture or liquid).

An exemplary spatial analysis workflow disclosed herein is provided. In some instances, the methods include providing a first substrate that includes a biological sample and a second substrate that includes a plurality of capture probes. In some instances, the plurality of capture probes include oligonucleotide probes. In some instances, the plurality of capture probes includes analyte capture agents that can detect an analyte of interest (e.g., a protein) as described herein. The methods can be performed in an order determined by a person in the art. For example, as an exemplary overview, a first substrate include a biological sample. The biological sample then is stained using any of the methods described herein. In some instances, the biological sample is imaged, capturing the stain pattern created during the stain step. In some instances, the biological sample then is destained. After destaining, in some instances, a second substrate that includes capture probes as described herein is added to the first substrate. In some instances, the biological sample is permeabilized using methods disclosed herein (e.g., a solution that includes proteinase K and SDS). Permeabilization releases the analytes from the biological sample. Analytes then migrate from the first substrate and are captured by the second substrate. In some instances, after capture, the analytes and/or the probe can be amplified and the sequence can be determined using methods disclosed herein.

Current methods of aligning biological samples with barcoded areas in spatial transcriptomics assays involve a user carefully placing the biological sample onto a substrate that includes a plurality of barcoded probes. Thus, in some embodiments, an advantage of the devices described is providing an alignment tool for users to align a sample with a barcoded area. The devices of the disclosure can reduce user error during the assay analysis, thereby also reducing sample analysis costs. In some embodiments, another advantage of the devices of the disclosure is a reduction in the number of aberrations or imaging imperfections that may arise due to user error in aligning a biological sample with a barcoded area of the substrate. In some embodiments, the devices of the disclosure allow for pre-screening of samples for areas of interest. In some embodiments, the devices of the disclosure allow for archived samples to be examined.

In some instances, a biological sample on the first substrate is stained. The sample can be stained using known staining techniques, including Can-Grunwald, Giemsa, hematoxylin and eosin (H&E), hematoxylin, Jenner's, Leishman, Masson's trichrome, Papanicolaou, Romanowsky, silver, Sudan, Wright's, and/or Periodic Acid Schiff (PAS) staining techniques. PAS staining is typically performed after formalin or acetone fixation. In some embodiments, the biological sample can be stained using a detectable label (e.g., radioisotopes, fluorophores, chemiluminescent compounds, bioluminescent compounds, and dyes) as described elsewhere herein. In some embodiments, a biological sample is stained using only one type of stain or one technique. In some embodiments, staining includes biological staining techniques such as H&E staining. In some embodiments, staining includes biological staining using hematoxylin. In some embodiments, staining includes identifying analytes using fluorescently-conjugated antibodies. In some embodiments, a biological sample is stained using two or more different types of stains, or two or more different staining techniques. For example, a biological sample can be prepared by staining and imaging using one technique (e.g., H&E staining and brightfield imaging), followed by staining and imaging using another technique (e.g., IHC/IF staining and fluorescence microscopy) for the same biological sample. In some instances, a biological sample on the first substrate is stained.

In some instances, the methods include imaging the biological sample. In some instances, imaging occurs prior to sandwich assembly. In some instances, imaging occurs while the sandwich configuration is assembled. In some instances, imaging occurs during permeabilization of the biological sample. In some instances, image are captured using high resolution techniques (e.g., having 300 dots per square inch (dpi) or greater). For example, images can be captured using brightfield imaging (e.g., in the setting of hematoxylin or H&E stain), or using fluorescence microscopy to detect adhered labels. In some instances, high resolution images are captured temporally using e.g., confocal microscopy. In some instances, a low resolution image is captured. A low resolution image (e.g., images that are about 72 dpi and normally have an RGB color setting) can be captured at any point of the workflow, including but not limited to staining, destaining, permeabilization, sandwich assembly, and migration of the analytes. In some instances, a low resolution image is taken during permeabilization of the biological sample. In some instances, a low resolution Include an optional step: imaging the biological sample. Include embodiments for imaging prior to the sandwich assembly, and imaging while the sample is in the sandwich assembly (e.g., during perm). Include embodiments for hi-res imaging (in preferred embodiments, this happens prior to assembling the sandwich) and embodiments for low-res imaging (in preferred embodiments, this happens while the sample is in the sandwich assembly).

In some embodiments, the location of the one or more analytes in a biological sample are determined by immunofluorescence. In some embodiments, one or more detectable labels (e.g., fluorophore-labeled antibodies) bind to the one or more analytes that are captured (hybridized to) by a probe on the first slide and the location of the one or more analytes is determined by detecting the labels under suitable conditions. In some embodiments, one or more fluorophore-labeled antibodies are used to conjugate to a moiety that associates with a probe on the first slide or the analyte that is hybridized to the probe on the first slide. In some instances, the location(s) of the one or more analytes is determined by imaging the fluorophore-labeled antibodies when the fluorophores are excited by a light of a suitable wavelength. In some embodiments, the location of the one or more analytes in the biological sample is determined by correlating the immunofluorescence data to an image of the biological sample. In some instances, the tissue is imaged throughout the permeabilization step.

In some instances, biological samples can be destained. In some instances, destaining occurs prior to permeabilization of the biological sample. Methods of destaining or discoloring a biological sample are known in the art, and generally depend on the nature of the stain(s) applied to the sample. For example, H&E staining can be destained by washing the sample in HCl. In some instances, hematoxylin is destained by washing the sample in HCl. In some embodiments, destaining can include 1, 2, 3, or more washes in HCl. In some embodiments, destaining can include adding HCl to a downstream solution (e.g., permeabilization solution).

In some instances, the substrate that includes the sample (e.g., a histological tissue section) is hydrated. The sample can be hydrated by contacting the sample with a buffer that does not include a permeabilization reagent. In some embodiments, the buffer includes hydrochloric acid. In some embodiments, the buffer is a solvent. In some embodiments, buffer is a permeabilization buffer that does not contain any permeabilization reagents.

In some instances, one or both of the substrates can be coated with a dried permeabilization reagent. As mentioned above, the permeabilization reagent can be deposited in solution on the substrate and then dried. Alternatively, in other embodiments, the permeabilization reagent can be applied in dried form directly onto the first substrate. In some embodiments, the dried permeabilization reagent covers at least the surface area of the substrate that includes the feature array. In some embodiments, the dried permeabilization reagent covers a surface area of the substrate that is greater than the surface area which includes the feature array. In some embodiments, the dried permeabilization reagent is dried pepsin. In some embodiments, the dried permeabilization reagent is a dried permeabilization enzyme, a dried buffer, a dried detergent, or any combination thereof. In some embodiments, the dried detergent is dried octyl phenol ethoxylate.

In some instances, the biological sample can be permeabilized by exposing the sample to one or more permeabilizing agents. In some instances, permeabilization occurs after the biological sample is destained. In some instances, permeabilization occurs prior to assembly of the sandwich configuration. In some instances, permeabilization occurs while the sandwich configuration is assembled. Suitable agents for this purpose include, but are not limited to, organic solvents (e.g., acetone, ethanol, and methanol), cross-linking agents (e.g., paraformaldehyde), detergents (e.g., saponin, Triton-X100™, Tween-20™, or sodium dodecyl sulfate (SDS)), and enzymes (e.g., trypsin, proteases (e.g., proteinase K). In some instances, the permeabilizing agent includes proteinase K and SDS.

In some instances, permeabilization occurs for about 1 minute. In some instances, permeabilization occurs for about 5 minutes. In some instances, permeabilization occurs for about 1 minute, about 5 minutes, about 10 minutes, about 12 minutes, about 15 minutes, about 18 minutes, about 20 minutes, about 25 minutes, about 30 minutes, about 36 minutes, about 45 minutes, or about an hour. In some instances, the methods disclosed herein include adding a permeabilizing agent that includes proteinase K and SDS to a biological sample for 1 minute. In some instances, the methods disclosed herein include adding a permeabilizing agent that includes proteinase K and SDS to a biological sample for 5 minutes.

In some embodiments, after permeabilization of the biological sample, migration of the analyte occurs. In some instances, migration of the analyte from the biological sample to the second substrate is passive (e.g., via diffusion). Alternatively, in certain embodiments, migration of the analyte from the biological sample is performed actively (e.g., electrophoretic, by applying an electric field to promote migration). In some instances, first and second substrates can include a conductive epoxy. Electrical wires from a power supply can connect to the conductive epoxy, thereby allowing a user to apply a current and generate an electric field between the first and second substrates. In some embodiments, electrophoretic permeabilization results in higher analyte capture efficiency and better spatial fidelity of captured analytes (e.g., on a feature array) than random diffusion onto matched substrates without the application of an electric field (e.g., via manual alignment of the two substrates).

Between any of the methods disclosed herein, the methods can include a wash step (e.g., with SSC (e.g., 0.1×SSC)). Wash steps can be performed once or multiple times (e.g., 1×, 2×, 3×, between steps disclosed herein). In some instances, wash steps are performed for about 10 seconds, about 15 seconds, about 20 seconds, about 30 seconds, or about a minute. In some instances, three washes occur for 20 seconds each. In some instances, the wash step occurs before staining the sample, after destaining the sample, before permeabilization the sample, after permeabilization the sample, or any combination thereof.

In some embodiments, following initial contact between sample and a permeabilization agent, the permeabilization agent can be removed from contact with sample (e.g., by opening sample holder) a time that is less than a time for complete permeabilization of sample. In effect, only a portion of sample is permeabilized, and only a portion of the analytes in sample may be captured by feature array.

In some instances, the first substrate and the second substrate are arranged in a sandwich assembly, e.g., as described herein. It is noted that the terms first substrate and second substrate do not necessarily connote the particular order or location of the biological sample or capture probes. For example, in one instance, the first substrate includes the biological sample and the second substrate includes capture probes. In another instance, the first substrate includes capture probes and the second substrate includes the biological sample. In some embodiments, the tissue permeabilization process begins when the sample is contacted with the permeabilization buffer. During the permeabilization process, analytes are released from the sample. In some embodiments, analytes that are released from the permeabilized sample diffuse to the surface of the second substrate and are captured on the feature array (e.g., on barcoded probes). In some instances, there is a gap between the first and the second substrate. In some instances, the gap is about 1, 2, 2.5, 3, 4, 5, 6, 7, 8, 9, 10, 11, 12, 12, 5, 13, 14, 15, 16, 17, 18, 19, 20, 21, 22, 23, 24, 25 µm or more. In some embodiments, second substrate is placed in direct contact with the sample on the first substrate ensuring no diffusive spatial resolution losses. In some embodiments, an alignment mechanism is configured to maintain a separation between the first and second substrates when the first and second substrates are aligned. In some embodiments, the alignment mechanism is configured to maintain the separation such that at least a portion of the sample on the first substrate contacts at least a portion of the reagent medium on the second substrate. In some embodiments, the separation between the first and second substrates is between 2 microns and 1 mm, measured in a direction orthogonal to a surface of the first substrate that supports the sample. In some instances, the first substrate and the second substrate are separated (e.g., pulled apart). In some embodiments, the sample analysis (e.g., cDNA synthesis) can be performed on the first substrate after the first substrate and the second substrate are separated. In some embodiments, the substrate comprising the biological sample can be discarded or archived after the first substrate and the second substrate are separated.

In some instances, the reduced amount of analyte captured and available for detection can be offset by the reduction in lateral diffusion that results from incomplete permeabilization of sample. In general, the spatial resolution of the assay is determined by the extent of analyte diffusion in the transverse direction (i.e., orthogonal to the normal direction to the surface of sample). The larger the distance between the sample on the first substrate and the feature array on the second substrate, the greater the extent of diffusion in the transverse direction, and the concomitant loss of resolution. Analytes liberated from a portion of the sample closest to the feature array have a shorter diffusion path, and therefore do not diffuse as far laterally as analytes from portions of the sample farthest from the feature array. As a result, in some instances, incomplete permeabilization of the sample (by reducing the contact interval between the permeabilization agent and the sample) can be used to maintain adequate spatial resolution in the assay.

In some instances, an analytical workflow may be substantially similar in several aspects to the example analytical workflow discussed above, but can include an alternative methods to control a temperature of the first and second substrates throughout the analytical process instead of not controlling temperature. In some embodiments, the temperature of the first and second members is lowered to a first temperature that is below room temperature (e.g., 25 degrees Celsius) (e.g., 20 degrees Celsius or lower, 15 degrees Celsius or lower, 10 degrees Celsius or lower, 5 degrees Celsius or lower, 4 degrees Celsius or lower, 3 degrees Celsius or lower, 2 degrees Celsius or lower, 1 degree Celsius or lower, 0 degrees Celsius or lower, −1 degrees Celsius or lower, −5 degrees Celsius or lower). In some embodiments, the sample holder includes a temperature control system (e.g., heating and cooling conducting coils) that enables a user to control the temperature of the sample holder. Alternatively, in other embodiments, the temperature of the sample holder is controlled externally (e.g., via refrigeration or a hotplate). In a first step, the second member, set to or at the first temperature, contacts the first substrate, and the first member, set to or at the first temperature, contacts the second substrate, thereby lowering the temperature of the first substrate and the second substrate to a second temperature. In some embodiments, the second temperature is equivalent to the first temperature. In some embodiments, the first temperature is lower than room temperature (e.g., 25 degrees Celsius). In some embodiments, the second temperature ranges from about −10 degrees Celsius to about 4 degrees Celsius. In some embodiments, the second temperature is below room temperature (e.g., 25 degrees Celsius) (e.g., 20 degrees Celsius or lower, 15 degrees Celsius or lower, 10 degrees Celsius or lower, 5 degrees Celsius or lower, 4 degrees Celsius or lower, 3 degrees Celsius or lower, 2 degrees Celsius or lower, 1 degree Celsius or lower, 0 degrees Celsius or lower, −1 degrees Celsius or lower, −5 degrees Celsius or lower).

The first substrate, which includes the feature array, is contacted with the dried permeabilization reagent. In some embodiments, the first substrate is contacted with a permeabilization reagent that is a gel or a liquid. Also in first step, the sample is contacted with buffer. Both the first and second substrates are placed at lower temperature to slow down diffusion and permeabilization efficiency. Alternatively, in some embodiments, the sample can be contacted directly with a liquid permeabilization reagent without inducing an unwanted initiation of permeabilization due to the substrates being at the second temperature. In some embodiments, the low temperature slows down or prevents the initiation of permeabilization.

In a second step, keeping the sample holder and substrates at a cold temperature (e.g., at the first or second temperatures) continues to slow down or prevent the permeabilization of the sample. In a third step, the sample holder (and consequently the first and second substrates) is heated up to initiate permeabilization. In some embodiments, the sample holder is heated up to a third temperature. In some embodiments, the third temperature is above room temperature (e.g., 25 degrees Celsius) (e.g., 30 degrees Celsius or higher, 35 degrees Celsius or higher, 40 degrees Celsius or higher, 50 degrees Celsius or higher, 60 degrees Celsius or higher). In some embodiments, analytes that are released from the permeabilized tissue of the sample diffuse to the surface of the first substrate and are captured on the feature array (e.g., barcoded probes) of the second substrate. In a fourth step, the first substrate and the second substrate are separated (e.g., pulled apart) and temperature control is stopped.

In some embodiments, where either the first substrate or substrate second (or both) includes wells, a permeabilization solution can be introduced into some or all of the wells, and then the sample and the feature array can be contacted by closing the sample holder to permeabilize the sample. In certain embodiments, a permeabilization solution can be soaked into a hydrogel film that is applied directly to the sample, and/or soaked into features (e.g., beads) that form the feature array. When the sample and the feature array are contacted by closing the sample holder, the permeabilization solution promotes migration of analytes from the sample to the feature array.

In certain embodiments, different permeabilization agents or different concentrations of permeabilization agents can be infused into array features (e.g., beads) or into a hydrogel layer as described above. By locally varying the nature of the permeabilization reagent(s), the process of analyte capture from the sample can be spatially adjusted.

First and second substrates can include a conductive epoxy. Electrical wires from a power supply can connect to the conductive epoxy, thereby allowing a user to apply a current and generate an electric field between the first and second substrates. In some embodiments, electrophoretic permeabilization results in higher analyte capture efficiency and better spatial fidelity of captured analytes (e.g., on a feature array) than random diffusion onto matched substrates without the application of an electric field (e.g., via manual alignment of the two substrates).

Loss of spatial resolution can occur when analytes migrate from the sample to the feature array and a component of diffusive migration occurs in the transverse (e.g., lateral) direction, approximately parallel to the surface of the first substrate on which the sample is mounted. To address this loss of resolution, in some embodiments, a permeabilization agent deposited on or infused into a material with anisotropic diffusion can be applied to the sample or to the feature array. The first and second substrates are aligned by the sample holder and brought into contact. A permeabilization layer that includes a permeabilization solution infused into an anisotropic material is positioned on the second substrate.

In some embodiments, the feature array can be constructed atop a hydrogel layer infused with a permeabilization agent. The hydrogel layer can be mounted on the second substrate, or alternatively, the hydrogel layer itself may function as the second substrate. When the first and second substrates are aligned, the permeabilization agent diffuses out of the hydrogel layer and through or around the feature array to reach the sample. Analytes from the sample migrate to the feature array. Direct contact between the feature array and the sample helps to reduce lateral diffusion of the analytes, mitigating spatial resolution loss that would occur if the diffusive path of the analytes was longer.

In some embodiments, following initial contact between the sample and a permeabilization agent, the permeabilization agent can be removed from contact with the sample (e.g., by opening the sample holder) after a time that is less than a time for complete permeabilization of the sample. In effect, only a portion of the sample is permeabilized, and only a portion of the analytes in the sample may be captured by the feature array.

However, the reduced amount of analyte captured and available for detection can be offset by the reduction in lateral diffusion that results from incomplete permeabilization of the sample. In general, the spatial resolution of the assay is determined by the extent of analyte diffusion in the transverse direction (i.e., orthogonal to the normal direction to the surface of the sample). The larger the distance between the sample and the feature array, the greater the extent of diffusion in the transverse direction, and the concomitant loss of resolution. Analytes liberated from only the upper portion of the sample closest to the feature array have a shorter diffusion path, and therefore do not diffuse as far laterally as analytes from portions of the sample furthest from the feature array. As a result, incomplete permeabilization of the sample (by reducing the contact interval between the permeabilization agent and the sample) can be used to maintain adequate spatial resolution in the assay.

In some instances, mounting the sample onto the first substrate include sectioning of the tissue sample (e.g., cryostat sectioning) followed by a fixation step. In some instances, the fixation step can include fixation with methanol. In some instances, the fixation step includes formalin (e.g., 2% formalin). In some instances, the methods can further include a blocking step. The blocking step can include the use of blocking probes to decrease unspecific binding of the antibodies to the array. The blocking step can optionally further include contacting the biological sample with a detergent. In some instances, the detergent can include Triton X-100™. The method can further include an antibody incubation step. In some embodiments, the antibody incubation step effects selective binding of the antibody to antigens of interest in the tissue sample. In some embodiments, the antibody is conjugated to an oligonucleotide (e.g., an oligonucleotide-antibody conjugate as described herein). In some embodiments, the antibody is not conjugated to an oligonucleotide. In some embodiments, the method further comprises an antibody staining step. The antibody staining step can include a direct method of immunostaining in which a labelled antibody binds directly to the analyte being stained for. Alternatively, the antibody staining step can include an indirect method of immunostaining in which a first antibody binds to the analyte being stained for, and a second, labelled antibody binds to the first antibody. In some embodiments, the antibody staining step is performed prior to sandwich assembly. In some embodiments wherein an oligonucleotide-antibody conjugate is used in the antibody incubation step, the method does not comprise an antibody staining step.

The method can further include imaging steps using any appropriate method described herein followed by a permeabilization step. In some embodiments, the imaging step comprises immunofluorescence. In some instances, the permeabilization step can include the use of pepsin and hydrochloric acid. In methods using the sandwich array process, the permeabilization step can include the use of proteinase K and sodium dodecyl sulfate (SDS). Following the permeabilization step is standard cDNA synthesis and library preparation as further described herein.

EXAMPLES

Example 1. Exemplary Fluid Delivery Schemes

In the example sandwich maker workflows described herein, a liquid reagent (e.g., the permeabilization solution 305) may fill a gap (e.g., the gap 307) between a tissue slide (e.g., slide 303) and a capture slide (e.g., slide 304 with barcoded capture probes 306) to warrant or enable transfer of target molecules with spatial information. Described herein are examples of filling methods that may suppress bubble formation and suppress undesirable flow of transcripts and/or target molecules or analytes. Robust fluidics in the sandwich making described herein may preserve spatial information by reducing or preventing deflection of molecules as they move from the tissue slide to the capture slide.

With reference to FIG. 9A, an exemplary sandwich configuration where a first substrate (e.g., slide 903), including a biological sample 902 (e.g., tissue section), and a second substrate (e.g., substrate (slide 904) including spatially barcoded capture probes 906) are brought into proximity with one another. Permeabilization buffer (e.g., the permeabilization solution 905) may be introduced in between the biological sample 902 and the array on the second substrate to release analytes that can be captured by the capture probes 906 of the array.

For example, FIG. 22A shows an exemplary fluid delivery scheme. Step 1 shows the first substrate (e.g., slide 903) including a biological sample (e.g., sample 902) and an array 906 (e.g., a spatial array) on a second substrate (e.g., slide 904). Step 2 shows the application of a gasket 2210 that substantially encompasses the array 906 (e.g., partially encloses), however, the gasket 2210 can be applied to substantially encompass the biological sample 902 instead or additionally. The example gasket 2210 shown in FIG. 22A includes two apertures, but the gasket 2210 can also include zero, one, or two or more apertures. Step 3 shows an exemplary assembly to generate a partially sealed or fully sealed chamber. Step 3 also shows the first substrate and second substrate brought into proximity to form a sandwich assembly. In FIG. 22A, step 3 is shown with the first and second substrates (e.g., slides 903 and 904, respectively) aligned in a cross-configuration, however, the first substrate and the second substrate can also be aligned at various angles. For example, the first substrate and the second substrate can also be axially aligned (e.g., in a sandwich assembly as described herein). When the first substrate (e.g., slide 903), the second substrate (e.g., slide 904), and the gasket 2210 are assembled (e.g., in a sandwich assembly, any of the configurations described herein) a partially sealed or a fully sealed chamber may be formed where fluid can be delivered (e.g., through an aperture, through a via-hole, or the like) to the partially enclosed volume of the chamber. Step 4 shows delivery of a fluid (e.g., the permeabilization solution 905) to an aperture of the gasket via capillary flow. Alternatively, at Step 4 the fluid can be delivered at a cold temperature (e.g., about 5° C. to about 25° C.) and heated as shown in FIG. 22B. Step 5 (FIG. 22B) shows that heating of the first substrate (e.g., slide 903) and/or the second substrate (e.g., slide 904) configuration can actuate the rate of permeabilization of the biological sample 902.

FIG. 23 shows a similar exemplary fluid delivery scheme as FIGS. 22A-22B, but as shown in Step 1, dried permeabilization reagents are disposed on the array 906. While not shown, dried permeabilization reagents can also be disposed on the biological sample 902. Similar to FIG. 22A, a gasket 2210 is applied (Step 2) and the first and second substrates (e.g., slides 903 and 904, respectively) are assembled (e.g., a sandwich assembly) (Step 3). As shown in Step 4, a fluid (e.g., a buffer) is delivered via capillary action to solubilize the dried permeabilization reagents.

FIG. 24 shows an exemplary fluid delivery scheme similar to FIGS. 22A-22B, but as shown in in Step 3, the fluid delivery mechanism is a syringe 2415 that interfaces with the gasket 2210 (e.g., a reservoir in the gasket). At step 4, the fluid may be injected into the aperture by the syringe 2415.

FIG. 25A shows an exemplary fluid delivery scheme where a gasket 2210 includes no apertures and is disposed between the first substrate and the second substrate (e.g., slides 903 and 904, respectively) and where the first substrate and the second substrate are aligned in a cross-configuration. Similar to previous figures, while FIG. 25A shows a cross-configuration, the first substrate and the second substrate can be aligned at any angle, including axially (e.g., a sandwich assembly). As shown, the first substrate including the biological sample, can have one or more via-holes 2515 where a fluid, including a permeabilization solution (e.g., permeabilization solution 905) can be delivered (e.g., flowed through by capillary action, injected by a syringe, etc.) (FIG. 25A) or injected through a syringe 2415 (FIG. 25B). Alternatively or additionally, the second substrate can have one or more via-holes 2515 where a fluid, including a permeabilization solution, can be delivered as described herein.

Example 2. Exemplary Fluid Delivery Scheme

FIG. 26 shows an exemplary fluid delivery scheme including the use of a virtual gasket, (e.g., a hydrophobic coating 2615 as indicated by the arrow). As shown in Step 1 a hydrophobic coating 2615 is applied to surround (e.g., encompass) the array 906, however, the hydrophobic coating 2615 can also be applied to surround the biological sample 902, or both. The hydrophobic coating 2615 can be applied via a stamp or drawn, such as for example, with a wax crayon or a paraffin-based crayon. As shown in Step 2 a fluid (e.g., permeabilization solution) is loaded on to the array 906 via capillary flow. While not shown, the fluid can be loaded via a syringe. Alternatively, dried permeabilization reagents can be disposed on the first substrate and/or the second substrate and can be solubilized by the delivered fluid. When the first substrate, the second substrate, and the virtual gasket (e.g., the hydrophobic coating 2615) are assembled (e.g., in a sandwich assembly, any of the configurations described herein) a partially sealed chamber is formed where fluid can be delivered (e.g., through an aperture, through a via-hole) to the partially enclosed volume of the chamber.

FIG. 27 shows a configuration combining a hydrophobic coating 2615 and a gasket 2210. As shown in FIG. 27 the gasket includes an aperture 2710. A hydrophobic coating 2615 can be applied to the substrate not covered by the gasket (e.g., in the aperture 2710), to retain the delivered fluid (e.g., a buffer, the permeabilization solution 905). The hydrophobic coating 2615 can be applied to the aperture (e.g., one or more apertures) prior to delivering the fluid.

Example 3. Capture of an Analyte Using an Analyte Capture Agents in a Sandwich Array This example provides an exemplary method for analyzing an analyte in a biological sample. In a non-limiting example, a biological sample is sectioned and placed on a first slide. After fixing (e.g., with 2% formalin) and blocking (e.g., with Triton-X), the biological sample is incubated with one or more analyte capture agents. The one or more analyte capture agents are associated with an oligonucleotide. Exemplary analyte capture agents comprise an antibody-oligonucleotide conjugate as described herein. The sample is then stained (e.g., with H&E) and imaged according to any of the methods described herein. A second slide comprising a feature array is placed in proximity to the first slide, creating a sandwich configuration. Permeabilization occurs while the slides are in the sandwich configuration. Exemplary permeabilization conditions are described herein, and can include permeabilization with pepsin, or permeabilization with proteinase K and SDS. In some embodiments, the sample is at least partially permeabilized with proteinase K and SDS. The second slide includes a plurality of probes that include a spatial domain and a capture domain that detects both the oligonucleotides and analytes in the biological sample. In some embodiments, wherein a feature array is configured for capture of multiple analyte types, the feature array includes one or more multiplexed spatially-barcoded features. Exemplary multiplexed spatially barcoded features are described herein. The analyte migrates and is captured by probes on the second slide, and the capture probe is extended to capture the complementary sequence of the captured oligonucleotides and analytes. Following permeabilization, the sandwich is disassembled and the extended capture probe is then amplified and sequenced according to any one of the methods described herein. Subsequent sequence analysis is then used to determine spatial information regarding the analyte captured from the tissue sample.

Example 4. Immunostaining in Conjunction with a Sandwich Assembly Workflow

This example provides an exemplary method for integrating immunostaining into a sandwich assembly workflow as described herein. In a non-limiting example, a biological sample is sectioned and placed on a first slide. After fixing (e.g., with 2% formalin or with methanol) and blocking (e.g., with Triton-X), the biological sample is subjected to an antibody incubation step. Following the antibody incubation step, the method further comprises an antibody staining step. The antibody staining step can include a direct method of immunostaining in which a labelled antibody binds directly to the analyte being stained for. Alternatively, the antibody staining step can include an indirect method of immunostaining in which a first antibody binds to the analyte being stained for, and a second, labelled antibody binds to the first antibody. Following the antibody staining step, the sample is imaged, e.g., by immunohistochemistry or immunofluorescence. Following imaging, a second slide comprising a feature array is placed in proximity to the first slide, creating a sandwich configuration. Permeabilization occurs while the slides are in the sandwich configuration. Exemplary permeabilization conditions can include permeabilization with pepsin, or permeabilization with proteinase K and SDS. Analytes migrate to and are captured by probes on the second slide, then extended to capture the complementary sequence of the captured oligonucleotides and analytes. Following permeabilization, the sandwich is disassembled and the extended capture probe is then amplified and sequenced according to any one of the methods described herein. Subsequent sequence analysis is then used to determine spatial information regarding the analytes captured from the tissue sample.

Example 5: Filling Methods for Robust Fluidics During Sandwiching

In the example sandwich maker workflows described herein, a liquid reagent (e.g., the permeabilization solution 905) may fill a gap (e.g., the gap 907) between a tissue slide (e.g., slide 903) and a capture slide (e.g., slide 904 with barcoded capture probes 906) to warrant or enable transfer of target molecules with spatial information. Described herein are examples of filling methods that may suppress bubble formation and suppress undesirable flow of transcripts and/or target molecules or analytes. Robust fluidics in the sandwich making described herein may preserve spatial information by reducing or preventing deflection of molecules as they move from the tissue slide to the capture slide.

FIG. 28 shows an exemplary sandwich configuration 2800 where a first substrate (e.g., pathology slide 903), including a biological sample 902 (e.g., a tissue section), and a second substrate (e.g., slide 904 including spatially barcoded capture probes 906) are brought into proximity with one another in accordance with some example implementations. As shown in FIG. 28 a liquid reagent drop (e.g., permeabilization solution 905) is introduced on the second substrate in proximity to the capture probes 906 and in between the biological sample 902 and the second substrate (e.g., slide 904). The permeabilization solution 905 releases analytes that can be captured by the capture probes 906 of the array. As further shown, one or more spacers 1310 are positioned between the first substrate (e.g., pathology slide 903) and the second substrate (e.g., slide 904). The one or more spacers 1310 include one or more spacing members that assist in maintaining the spacing and/or approximately parallel arrangement of the first and second substrates.

The one or more spacers 1310 are configured to maintain a separation distance between the first substrate and the second substrate. The one or more spacers 1310 can be placed on the first substrate adjacent to the biological sample 902 and in between the first substrate and the second substrate. The one or more spacers 1310 can be placed on the second substrate adjacent to the array 906 and in between the first substrate and the second substrate. By doing so, the one or more spacers 1310 create a chamber (e.g., chamber 1350) in which solutions (e.g., a buffer, a permeabilization solution 905) are contained throughout the permeabilization and analyte migration process. In some embodiments, more than one spacer is used. In some embodiments, the one or more spacers 1310 have a height of about 2 µm, about 12.5 µm, about 15 µm, about 17.5 µm, about 20 µm, about 22.5 µm, or about 25 µm. In some embodiments, the height of each spacer has a height of about 50 µm, about 100 µm, about 200 µm, about 300 µm, about 400 µm, about 500 µm, about 600 µm, about 700 µm, about 800 µm, about 900 µm, or about 1000 µm. In some aspects, the one or more spacers 1310 have a height ranging from 1 to 100 µm. The height or thickness of the one or more spacers 1310 are selected based on the diffusive broadening of the fluid as described herein. The one or more spacers 1310 may be formed of a material having uniform thickness or of a material having a variable (e.g., beveled) thickness.

The one or more spacers 1310 create a fully or partially enclosed chamber around the biological sample (e.g., tissue sample 902 or a region of interest) and/or the array 906. The fully enclosed one or more spacers 1310 can be configured to any shape. In some embodiments, the fully enclosed (e.g., encompassed) chamber created by the one or more spacers 1310 is one of a square or a rectangle. In some embodiments, one or more spacers 1310 conform to the shape of the biological sample 902. For example, the one or more spacers 1310 are shown herein to have an example shape, an example height, and maintain an example separation distance (e.g., 12.5 µm), although other values and shapes are possible and may depend on the liquid reagent, the biological sample 902, the capture probes 906, or the like.

FIG. 28 shows an example of a fully formed sandwich creating a chamber 1350 formed from the one or more spacers 1310, the first substrate (e.g., the pathology slide 903), and the second substrate (e.g., the slide 904) in accordance with some example implementations. In the example of FIG. 28, the liquid reagent (e.g., the permeabilization solution 905) fills the volume of the chamber 1350 and creates a permeabilization buffer that allows mRNA transcripts and/or molecules to diffuse from the biological sample 902 toward the capture probes 906 of the slide 904. In some aspects, any flow of the permeabilization buffer may deflect transcripts and/or molecules from the biological sample 902 and may affect diffusive transfer of analytes for spatial analysis. A partially or fully sealed chamber 1350 resulting from the one or more spacers 1310, the first substrate, and the second substrate reduces or prevents flow from undesirable convective movement of transcripts and/or molecules over the diffusive transfer from the biological sample 902 to the capture probes 906.

FIG. 14 depicts an example configuration 1400 for venting or removing bubbles from the chamber 1350 in accordance with some example implementations. FIG. 14 depicts a top view of the chamber 1350 where a square portion includes the capture probes 906, a circular portion includes the biological sample 902, and a rectangular portion includes a hydrophobic area 1420. The hydrophobic area 1420 includes a hydrophobic pattern that does not wet and is disposed in a portion of the chamber 1350 that is located away from an area of interest (e.g., an area where the biological sample 902 and the capture probes 906 overlap). The hydrophobic area 1420 is configured to remove bubbles (e.g., bubbles 2015) from the chamber 1350 during the permeabilization step.

In some aspects, any combination of bubble venting or bubble removing features may be applied to the chamber, the first substrate, and/or the second substrate. For example, air permeable spacers (e.g., spacers 1310) may be configured to vent out trapped bubbles. Further, bubble venting holes disposed on the first substrate, the second substrate, and/or a spacer may be placed at strategic locations to vent bubbles. In some aspects, a sonication or vibration device may be configured to generate vibration on the first substrate and/or the second substrate during closing of the sandwich to reduce the chance of a bubble sticking to a surface of the first substrate or the second substrate. Additionally, it may be possible to increase a humidity of the chamber during sandwich closing to facilitate the filling process of the permeabilization solution or liquid reagent. Further, it may be possible to generate a vacuum in the chamber during closing to reduce or eliminate the chance of bubble trapping.

FIGS. 15A-15C show example configurations for that one or more spacers 1310 disposed on the first substrate (e.g., the pathology slide 903) and/or the second substrate (e.g., the slide 904) in accordance with some example implementations. While the slide 904 (e.g., the second substrate) is shown in FIGS. 15A-15C, the example spacer configurations may apply equally to the first substrate (e.g., the pathology slide 903) in accordance with example embodiments. In some aspects, the example spacer configurations of FIGS. 15A-15C may be combined with an angled closure workflow as described herein (e.g., workflow 1700 of FIGS. 17A-18B).

FIG. 15A is a top view of an example chamber 1350 having a partial enclosure with three sides of the one or more spacers 1310 closed. As shown, a drop of the permeabilization solution 905 is disposed along the open side of the chamber 1350 and on a surface of the slide 904. In some aspects, an angled closure of the first substrate (e.g., the pathology slide 903) contacting the drop 905 urges the permeabilization solution toward the one or more spacers 1310 partially surrounding the drop 905. In some implementations, the three sides of the one or more spacers 1310 at least partially surround capture probes 906 of the second substrate (e.g., slide 904) and/or the biological sample 902 of the first substrate (e.g., pathology slide 903).

FIG. 15B depicts a top view of another example chamber 1350 having a full enclosure. As shown, the one or more spacers 1310 fully surround and enclose the chamber 1350. As further shown, the drop of the permeabilization solution 905 is positioned outside of the chamber 1350 on a surface of the slide 904. As described above, an angled closure workflow (e.g., workflow 1700) of the first substrate (e.g., the pathology slide 903) over the second substrate (e.g., slide 904) results in a dropped side of the first substrate contacting the drop 905 and urging the permeabilization solution 905 toward and within the chamber 1350. In the example of FIG. 15B, the one or more spacers 1310 at least partially surround capture probes 906 of the second substrate (e.g., slide 904) and/or the biological sample 902 of the first substrate (e.g., pathology slide 903).

FIG. 15C depicts a top view of another example chamber 1350 having a full enclosure. As shown, the one or more spacers 1310 fully surround and enclose the chamber 1350. As further shown, the drop of the permeabilization solution 905 is positioned outside of the chamber 1350 and on a surface of the one or more spacers 1310. As described herein, an angled closure workflow (e.g., workflow 1700) of the first substrate (e.g., the pathology slide 903) over the second substrate (e.g., slide 904) results in a dropped side of the first substrate contacting the drop of the permeabilization solution 905 and urging the permeabilization solution 905 toward and within the chamber 1350. In the example of FIG. 15C, the one or more spacers 1310 at least partially surround capture probes 906 of the second substrate (e.g., slide 904) and/or the biological sample 902 of the first substrate (e.g., pathology slide 903).

FIGS. 16A-16E depict example configurations of the one or more spacers 1310 combined with one or more hydrophobic areas 1420 in accordance with some example implementations. Any or all of the example configurations shown may be combined with an angled closure workflow (e.g., workflow 1700) for sandwiching the first substrate and the second substrate and for forming the chamber 1350.

FIG. 16A depicts a top view of an example chamber 1350. As shown, the chamber 1350 comprises three sides of the one or more spacers 1310 and a fourth side including the hydrophobic area 1420. As further shown, the drop of the permeabilization solution 905 is located on the slide 904 proximate to the hydrophobic area 1420. As described above, an angled closure workflow (e.g., workflow 1700) of the first substrate (e.g., the pathology slide 903) over the second substrate (e.g., slide 904) results in a dropped side of the first substrate contacting the drop of the permeabilization solution 905 and urging the permeabilization solution 905 toward the opposite side and within the chamber 1350 having the three sides of the one or more spacers 1310.

FIG. 16B depicts a top view of another example chamber 1350. As shown, the chamber 1350 includes four spacers 1310 placed at the four corners of the chamber 1350 and the hydrophobic area 1420 comprising the sides of the chamber 1350. In the example of FIG. 16B, the spacers 1310 placed at the corners of the chamber 1350 retain a minimum spacing between a first substrate (e.g., the pathology slide 903) and the second substrate (e.g., the slide 904) during sandwiching. The hydrophobic area 1420 of FIG. 16B retains the permeabilization solution 905 within the chamber 1350 during the permeabilization step. During sandwiching, the permeabilization solution 905 fills the volume of the chamber 1350.

In some aspects, any combination of the one or more spacers 1310, the hydrophobic area 1420, or the like may be implemented to achieve the chamber 1350 assembly and achieve flow and/or bubble suppression. In some embodiments, the one or more spacers 1310 and/or the hydrophobic area 1420 may be disposed on either the first substrate (e.g., the pathology slide 903) or the second substrate (e.g., the slide 904).

FIG. 16C depicts a top view of an example configuration for the one or more spacers 1310 on the second substrate (e.g., the slide 904). As shown, the one or more spacers 1310 surround the drop of permeabilization solution 905 on three sides of the chamber 1350.

FIG. 16D depicts a top view of the first substrate (e.g., the pathology slide 903) including the biological sample 902 and the hydrophobic area 1420.

FIG. 16E depicts a top view of the first substrate (e.g., the pathology slide 903 of FIG. 16D) sandwiched with the second substrate (e.g., the slide 904 of FIG. 16C). As shown, the combination of the one or more spacers 1310 of FIG. 16C and the hydrophobic area 1420 of FIG. 16D form the fully enclosed chamber 1350 of FIG. 16E.

FIGS. 21A-21C depict a side view and a top view of an angled closure workflow 2100 for sandwiching a first substrate (e.g., pathology slide 903) having a tissue sample 902 and a second substrate (e.g., slide 904 having capture probes 906) in accordance with some example implementations.

FIG. 21A depicts the first substrate (e.g., the pathology slide 903 including sample 902) angled over (superior to) the second substrate (e.g., slide 904). As shown, a drop of the permeabilization solution 905 is located on top of the spacer 1310 toward the right-hand side of the side view in FIG. 21A.

FIG. 21B shows that as the first substrate lowers, or as the second substrate rises, the dropped side of the first substrate (e.g., a side of the slide 903 angled inferior to the opposite side) contacts the drop of the permeabilization solution 905. The dropped side of the first substrate urges the permeabilization solution 905 toward the opposite direction. For example, in the side view of FIG. 21B the permeabilization solution 905 may be urged from right to left as the sandwich is formed.

FIG. 21C depicts a full closure of the sandwich between the first substrate and the second substrate with the spacer 1310 contacting both the first substrate and the second substrate and maintaining a separation distance between the two. As shown in the top view of FIGS. 21B-21C, the spacer 1310 fully encloses and surrounds the tissue sample 902 and the capture probes 906, and the spacer 1310 forms the sides of chamber 1350 which holds a volume of the permeabilization solution 905.

Example 6: Efficient Analyte Capture from Slide-Mounted Fresh Frozen Mouse Brain Sections onto Spatial Array Slides Analyte capture onto spatially barcoded arrays and subsequent sequencing was demonstrated under sandwich and non-sandwich conditions. For the test (sandwiching) condition, archived tissue-mounted standard glass slides containing hematoxylin/eosin stained fresh frozen mouse brain sections were used. For control (non-sandwich) condition, array substrate slides with hematoxylin/eosin stained fresh frozen mouse brain sections mounted directly onto the array area were used. Under both conditions, tissue sections were subjected to a hematoxylin destaining step. Slides processed according to the "sandwiching" condition were briefly dried at 37° C., then mounted in the sample handling apparatus described herein along with an array substrate described herein and a permeabilization buffer comprising sarkosyl and proteinase K. Upon sandwich closure in the instrument, the tissue sections were permeabilized for 1 minute. For the tissue-mounted array substrates processed according to the non-sandwich condition, sections were permeabilized for 5 minutes using the same permeabilization buffer without sandwiching. For both conditions, following permeabilization, captured polyA-containing mRNA transcripts on the array substrates were reverse transcribed into cDNA, followed by standard sequencing library preparation and sequencing.

Figures 35, 36:
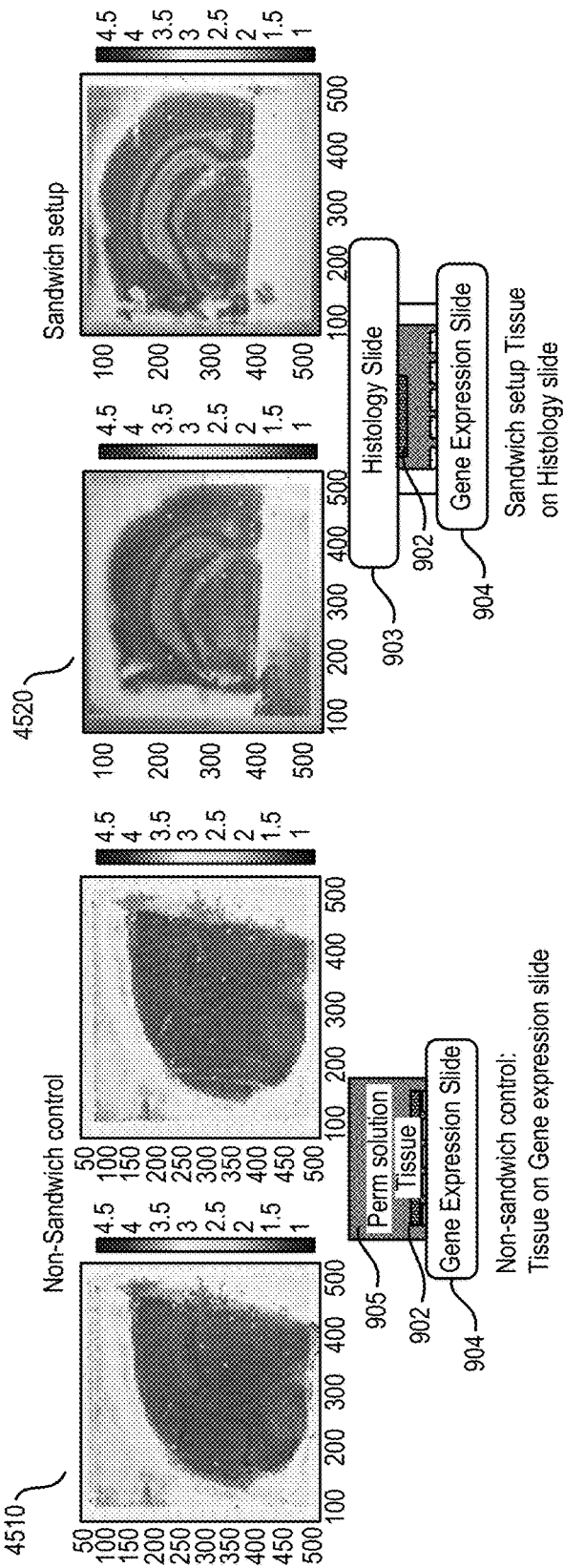
FIG. 35 depicts a table of example parameters of the workflow for performing sample analysis in accordance with example implementations.
FIG. 36 depicts a comparison between a non-sandwich control permeabilization step and a sandwich configuration permeabilization step in accordance with example implementations.

Results depicting median genes per spot and median UMI counts per spot are shown in FIG. 35.

Visual heat map results showing Log 10 UMIs are shown in FIG. 36. Spatial patterns of the Log 10 UMI counts were similar across the sandwich and non-sandwich conditions.

Figure 37:
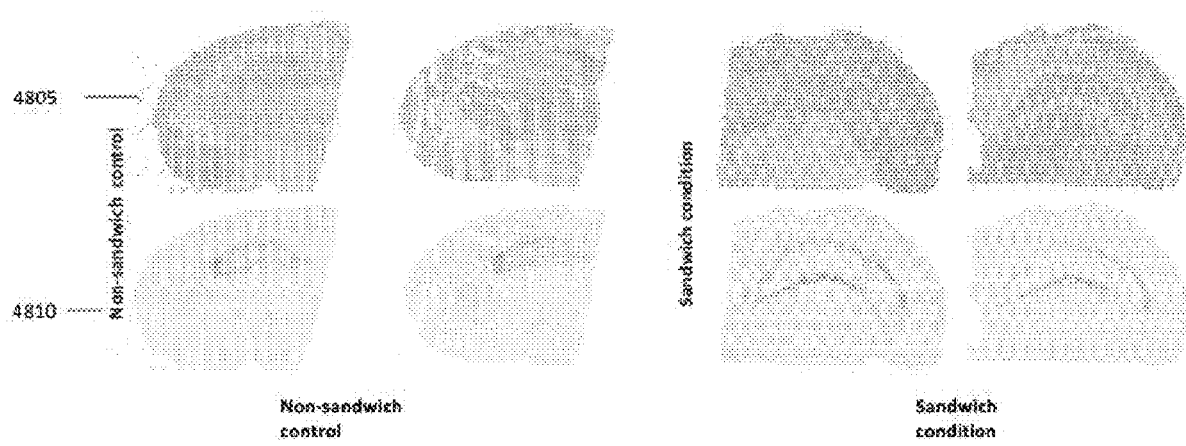
FIG. 37 depicts an example of spatial clustering analysis and analysis of hippocampal transcript Hpca in accordance with some example implementations.

Spatial clustering analysis (top row 4805) and analysis of hippocampal transcript Hpca (bottom row 4810) are depicted in FIG. 37. Spatial patterns were comparable across the sandwich and non-sandwich conditions.

In some embodiments, instead of sandwiching the substrate including a sample of tissue with the substrate including the array of spatial barcodes described herein, the substrate including a sample of tissue can be sandwiched with a tissue optimization assay substrate which has a distributed area containing a plurality of PolyT capture probes. mRNA transcripts can be reverse transcribed in the presence of fluorescently labeled nucleotides, which can result in fluorescent cDNA linked to the capture probes. The linked cDNA can then be imaged. Image brightness and image sharpness can provide indications of the degree to which permeabilization and transcript capture was accomplished.

Figures 40A, 40B, 40C:
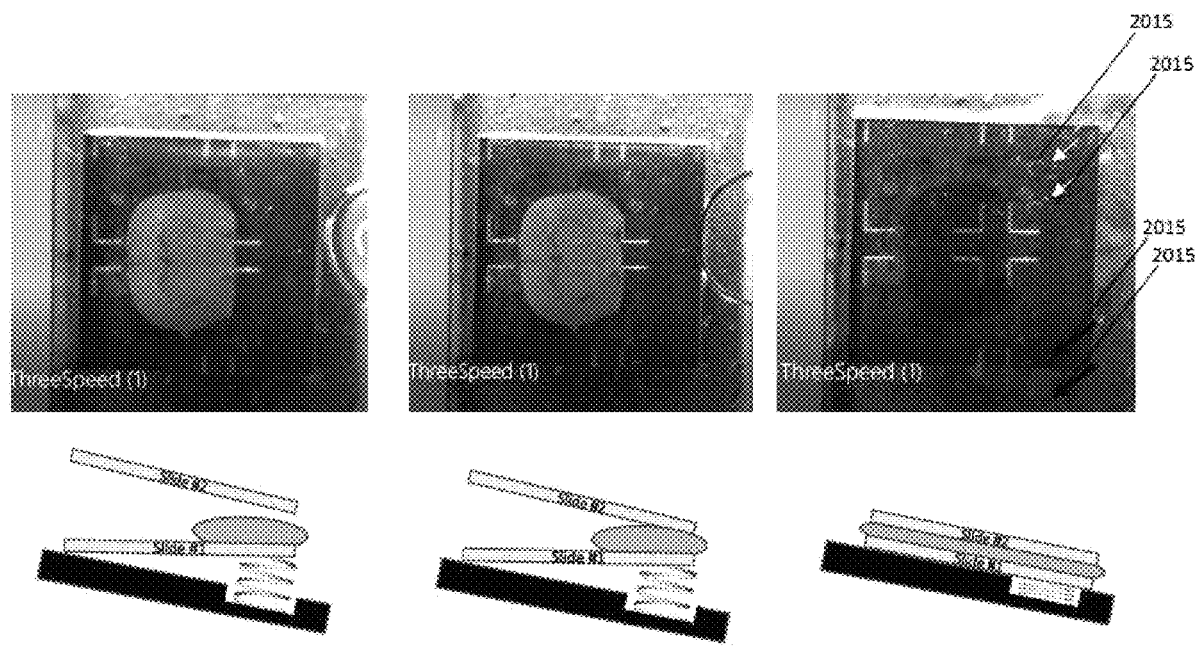
FIGS. 40A-C depict an example slow closing speed condition for a sandwich assembly using angled closure in accordance with some example implementations.

Example 7: Sandwich Assembly Using Angled Closure and Closing Speed for Minimal Bubble Generation/Trapping During Permeabilization In one example aspect, an angled closure (e.g., see workflow 1700 and FIGS. 17A-18B) for the sandwich configuration was tested at three different closing speeds resulting in closing times of approximately 370 ms (fast), approximately 550 ms (medium), and approximately 1100 ms (slow), respectively. For each of the closing speed conditions, slide 1706 was a glass slide with a coronal mouse brain tissue section mounted thereon and slide 1712 was an array substrate described herein comprising an array of spatially encoded capture probes. For the fast closing speed condition (e.g., closing occurring within approximately 370 ms), it was observed that a liquid reagent drop (e.g., drop 1705) filled the gap (e.g., gap 907, FIG. 9) between the two substrates without any bubbles trapped within the reagent medium and between the substrates. See FIGS. 38A-C. For the medium closing speed condition (e.g., closing occurring within approximately 550 ms), it was observed that a liquid reagent drop filled the gap between the two substrates without any bubbles trapped within the reagent medium in between the substrates. See FIGS. 39A-C. For the slow closing speed condition (e.g., closing occurring within approximately 1100 ms), it was observed that a liquid reagent drop filled the gap between the two substrates with a few bubbles 2015 trapped within the reagent medium and between the substrates. See FIGS. 40A-C. However, even with the slow closing speed, there were no bubbles observed between the tissue section on slide 1706 and array area on slide 1112. Accordingly, efficient analyte capture is enabled at all three closing speeds, with fast and medium speeds reducing the incidence of bubble trapping anywhere in the sandwich area. The observation that fast and medium closing speeds minimized bubble generation/trapping were consistent across multiple rounds.

While example closing speed values are described above, other closing speeds are possible.

Example 8: Assessment of Current Flow Velocity Using Dye Streak Method

To assess lateral flow in a reagent medium during sandwiching of a tissue slide and spatially barcoded array slide, a gene expression (GEx) slide with a fully enclosed spacer attached thereon was sandwiched with a standard glass slide using an angled closure method disclosed herein (e.g., see workflow 1700 and FIGS. 17A-18B). For the angled closure method, the GEx slide was placed on the bottom and the glass slide was positioned superior to the GEx slide. A reagent medium drop was positioned on the spacer of the GEx slide, such that a dropped slide of the glass slide would make initial contact the reagent drop during sandwich closure. Additionally, a dye spot was placed within the area of the GEx slide enclosed by the spacer. After closure, the slides were held in the sandwich configuration for a period of time (e.g., 30 minutes to 2 hours), during which video images were captured at 1 frame per second to visualize dye front migration through the reagent medium. The intensity profile of the video images were subjected to Gaussian fitting and peak tracking analysis to assess lateral flow velocity of the dye streak within the enclosed sandwich chamber.

Figure 41A:
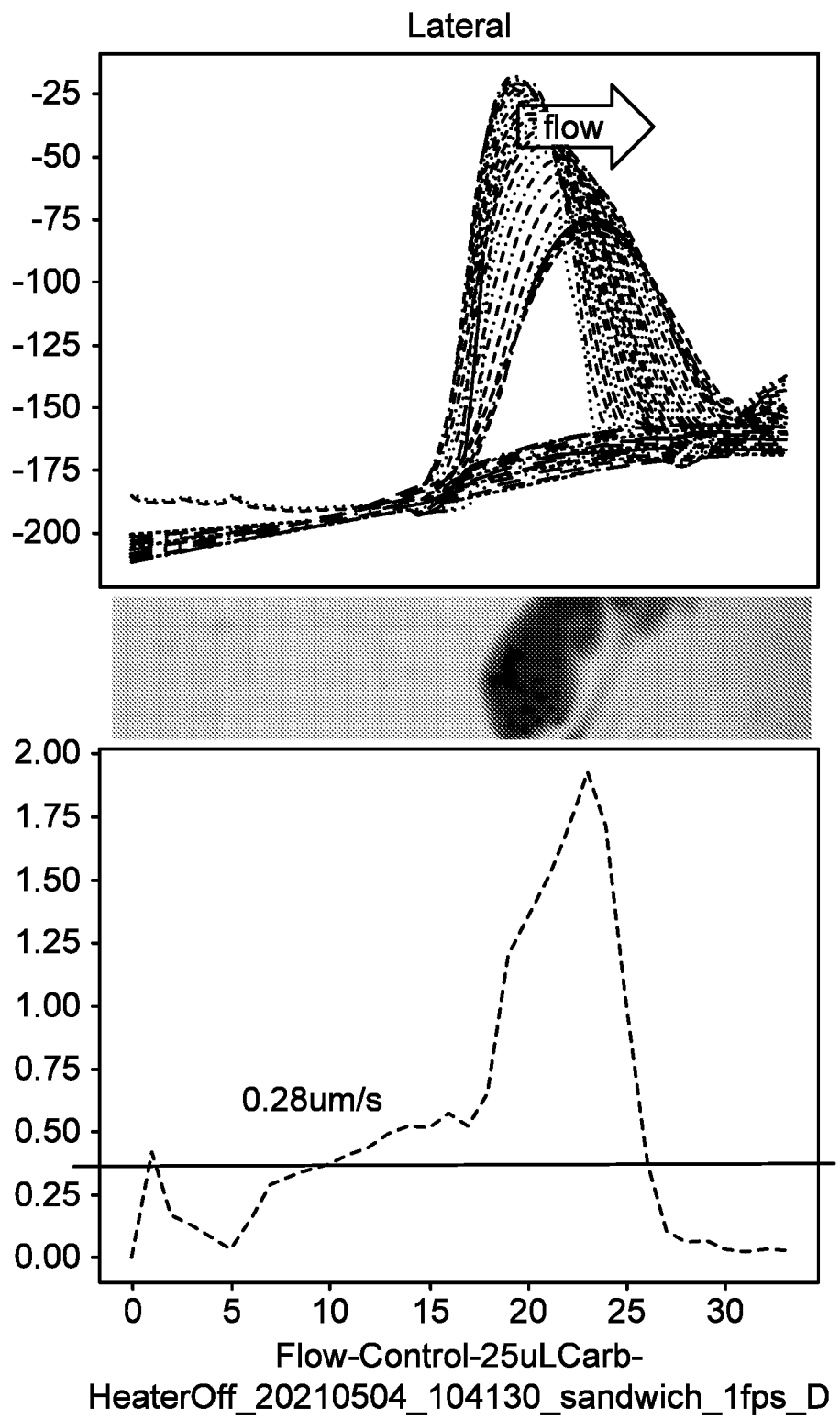
FIGS. 41A-41C show graphs of example flow velocities using a dye streak method and a sandwich configuration.
Figure 41B:
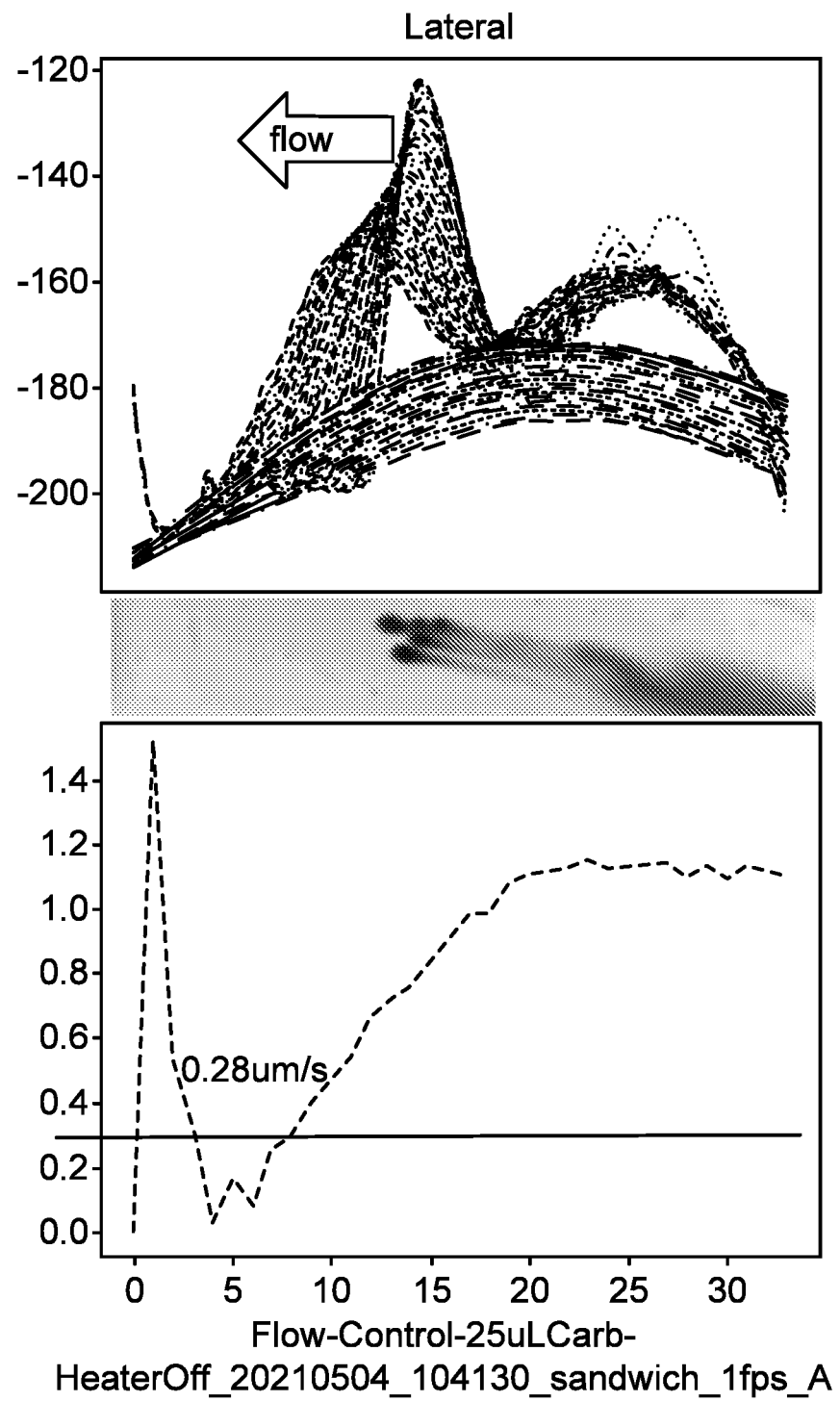
Figure 41C:
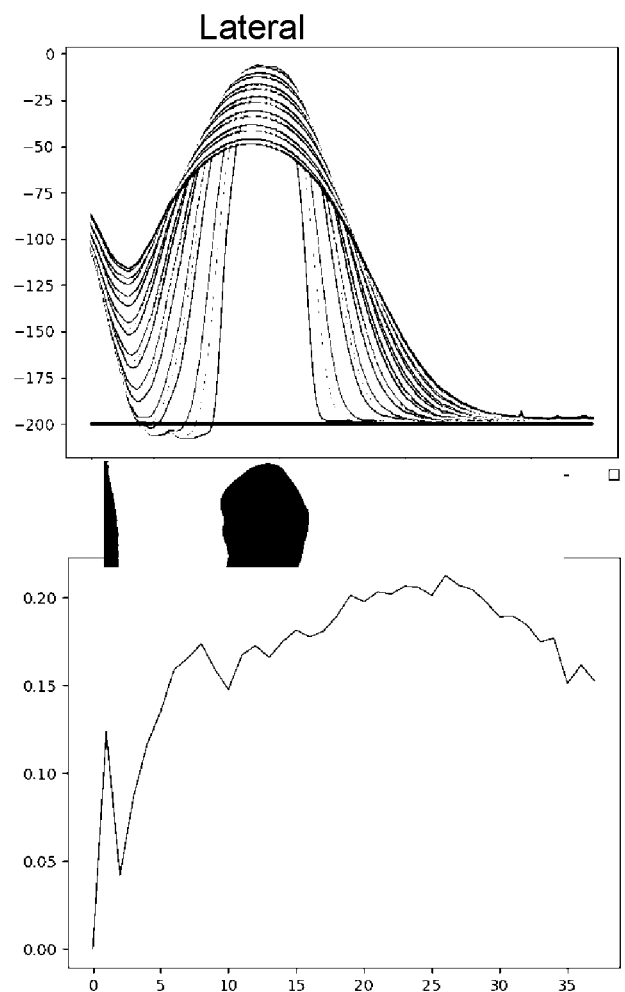
Figures 42A, 42B, 42C, 42D:
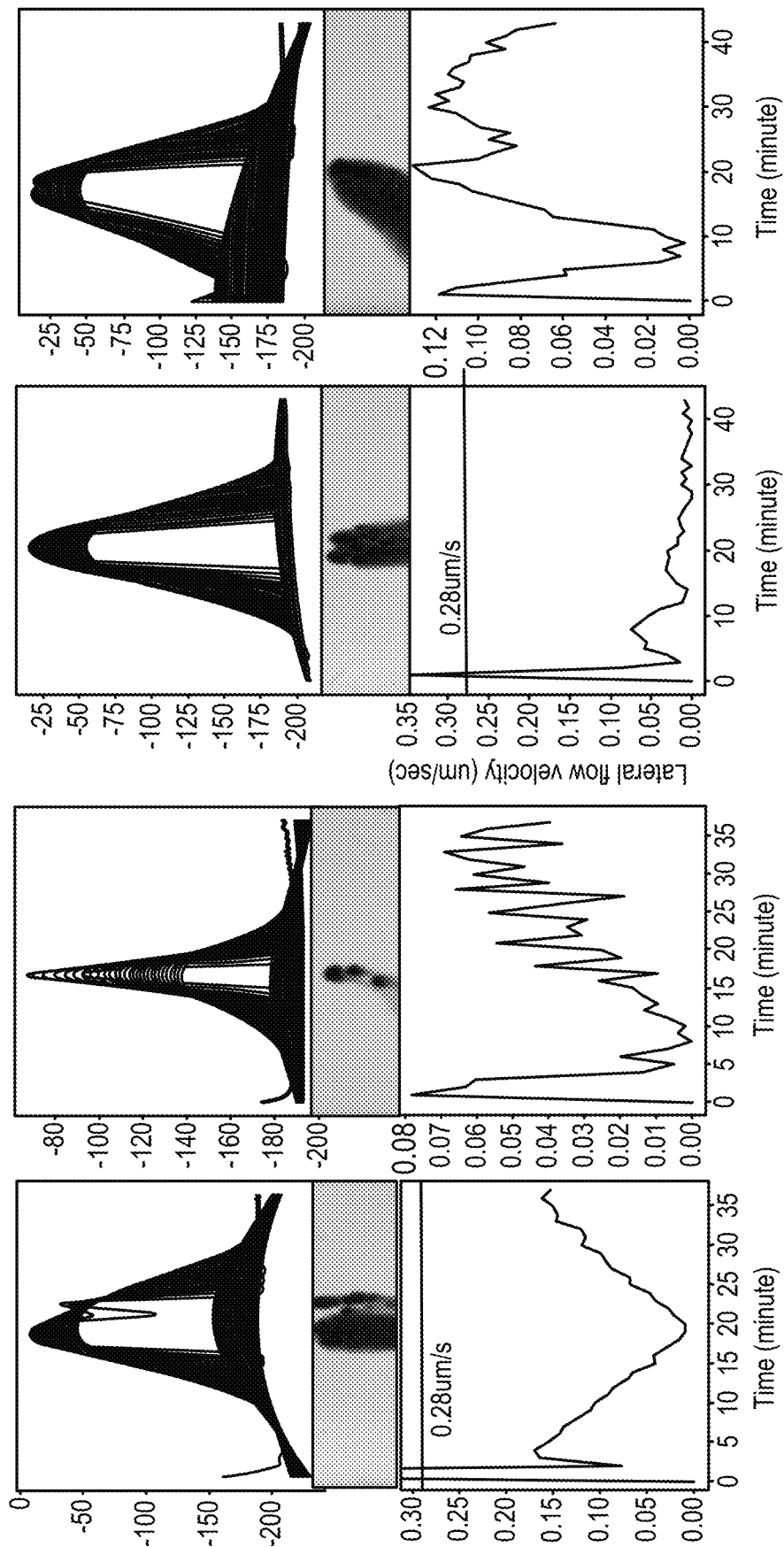
FIGS. 42A-42D show graphs of example flow velocities using a dye streak method and a sandwich configuration.

Results are depicted in FIGS. 41A-41C. As shown, FIGS. 41A and 41B depict a lateral flow velocity spike over time. FIG. 41C depicts an example where a lateral flow velocity spike did not occur. As shown in the examples of FIGS. 41A-41C, occasional lateral flow spikes can occur under certain sandwiching conditions.

It was further observed that after sandwiching, the retaining mechanism (e.g., slide holder) for the array slide exhibited occasional wet streaks. Without wishing to be bound by theory, it is possible that capillary flow developed between the slide and slide holder due to a leaky seal created by the spacer, allowing a portion of the reagent medium to leak outside the chamber and seep under the slide (e.g., as depicted in FIG. 32A).

The dye front experiment above was repeated, using either a silicone spacer with improved fluidic seal or a silicone backing attached to the bottom of the tissue slide and array slide comprising the spacer. In both cases, no wet streaks were observed on the bottom of the tissue or array slides (data not shown). In both cases, flow spikes (e.g., spikes in lateral flow velocity U) were essentially eliminated. See, e.g., FIGS. 42A-42D show graphs of example flow velocities using a dye streak method and the sandwich configuration 3300 of FIG. 33 (using the silicone backing). Similar results were observed for the experiment using the silicone spacer with improved fluidic seal (data not shown).

The subject matter described herein may be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations may be provided in addition to those set forth herein. For example, the implementations described above may be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

The invention claimed is:

1. A method for delivering a fluid to a tissue section, the method comprising:
   delivering the fluid to a second substrate comprising a spatial array disposed thereon, the spatial array comprising a plurality of discrete features each comprising a plurality of capture probes attached to the second substrate, wherein a capture probe of the plurality of capture probes comprises (i) a capture domain and (ii) a spatial barcode unique to the feature, wherein the second substrate comprises a spacer disposed thereon, wherein the spacer is positioned to surround the spatial array; and
   assembling, subsequent to the delivering, a first substrate comprising the tissue section and the second substrate, to form a chamber, wherein the spacer is disposed between the first substrate and the second substrate and is configured to maintain the fluid within the chamber and maintain a separation distance of less than 25 µm between the first substrate and the second substrate, the spacer further comprising a reservoir positioned within a wall of the spacer surrounding the chamber, the reservoir having an opening, wherein the fluid is delivered into the opening of the reservoir,
   wherein assembling the chamber comprises positioning the first substrate at an angle relative to the second substrate such that a dropped side of the first substrate contacts at least a portion of the fluid when the first substrate and the second substrate are within a threshold distance along an axis orthogonal to the second substrate, the dropped side of the first substrate urging the fluid from the reservoir toward a side of the first substrate that is opposite the dropped side and into the chamber,
   wherein the spacer comprises a material selected to promote a contact angle of at least 50 degrees,
   and wherein the first substrate, the spacer, and the second substrate at least partially enclose a volume comprising the tissue section.

2. The method of claim 1, wherein the first substrate, the spacer, and the second substrate fully enclose the volume comprising the tissue section.

3. The method of claim 1, wherein the chamber comprises a partially or fully sealed chamber.

4. The method of claim 1, wherein the separation distance comprises a distance of at least 2 µm.

5. The method of claim 1, wherein the separation distance comprises a distance between about 5 µm to 25 µm.

6. The method of claim 1, wherein the fluid comprises one or more permeabilization reagent(s).

7. The method of claim 1, wherein the opening of the reservoir is positioned on a side of the spacer opposite of a side of the first substrate comprising the tissue section when the chamber is formed.

8. The method of claim 1, wherein the spacer is formed from a uniform thickness material.

9. The method of claim 1, wherein the spacer is printed on the second substrate or is attached to the second substrate via an adhesive.

10. The method of claim 1, wherein the spacer comprises a photoresist.

11. The method of claim 1, wherein the spacer comprises a beveled edge on one or more sides of the spacer.

12. The method of claim 1, wherein the capture probe further comprises a functional domain, a cleavage domain, a unique molecular identifier, or any combination thereof.

13. The method of claim 1, further comprising:
    migrating one or more molecules from the tissue section toward the plurality of capture probes via the fluid; and
    binding the one or more molecules from the tissue section to one or more capture probes of the plurality of capture probes.

14. The method of claim 13, wherein the migrating comprises active migration via electrophoresis.

15. The method of claim 13, wherein the migrating comprises passive migration via diffusion.

16. The method of claim 13, wherein the binding occurs via hybridization.

17. The method of claim 13, wherein the one or more molecules comprise nucleic acids.

18. The method of claim 1, wherein a feature of the plurality of features is a spot.

19. The method of claim 1, wherein the capture domain of the capture probe comprises a poly(T) sequence.

20. The method of claim 1, wherein the spacer comprises a material selected from graphite, polyester, Polytetrafluoroethylene (PTFE), polyamide, polychlorotrifluoroethylene (PCTFE), poly(ethene-co-tetrafluoroethene) (ETFE), and PEEK (Polyether ether ketone).

* * * * *